US010415045B2

(12) United States Patent
Punt et al.

(10) Patent No.: US 10,415,045 B2
(45) Date of Patent: *Sep. 17, 2019

(54) FUNGAL PRODUCTION SYSTEM

(71) Applicant: Danisco US, Inc., Palo Alto, CA (US)

(72) Inventors: Peter J. Punt, Houten (NL); Richard Paul Burlingame, Nicholasville, KY (US); Christine M. Pynnonen, Appleton, WI (US); Phillip T. Olson, Two Rivers, WI (US); Jan Wery, Gorssel (NL); Johannes Heinrich Visser, Wijchen (NL); Mark A. Emalfarb, Jupiter, FL (US); Jacob Visser, Wageningen (NL); Jan Cornelis Verdoes, Wageningen (NL)

(73) Assignee: DANISCO US INC CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/848,754

(22) Filed: Sep. 9, 2015

(65) Prior Publication Data

US 2015/0376629 A1 Dec. 31, 2015

Related U.S. Application Data

(62) Division of application No. 13/138,661, filed as application No. PCT/NL2010/000045 on Mar. 16, 2010, now Pat. No. 9,175,296.

(30) Foreign Application Priority Data

Mar. 16, 2009 (EP) ..................................... 09003750

(51) Int. Cl.
| | |
|---|---|
| *C12N 15/80* | (2006.01) |
| *C12N 1/14* | (2006.01) |
| *C12N 9/12* | (2006.01) |
| *C12N 9/34* | (2006.01) |
| *C12N 15/01* | (2006.01) |
| *C12P 21/02* | (2006.01) |
| *C12N 9/42* | (2006.01) |
| *C12N 9/24* | (2006.01) |
| *C12R 1/645* | (2006.01) |
| *C12Q 1/40* | (2006.01) |

(52) U.S. Cl.
CPC .............. *C12N 15/80* (2013.01); *C12N 1/14* (2013.01); *C12N 9/1205* (2013.01); *C12N 9/2402* (2013.01); *C12N 9/248* (2013.01); *C12N 9/2428* (2013.01); *C12N 9/2437* (2013.01); *C12N 9/2442* (2013.01); *C12N 15/01* (2013.01); *C12P 21/02* (2013.01); *C12Q 1/40* (2013.01); *C12R 1/645* (2013.01); *C12Y 302/01003* (2013.01); *C12Y 302/01004* (2013.01); *C12Y 302/01006* (2013.01); *C12Y 302/01008* (2013.01); *C12Y 302/01014* (2013.01); *C12Y 302/01015* (2013.01); *C12Y 302/01091* (2013.01); *C12Y 304/21062* (2013.01); *C12Y 304/23025* (2013.01); *G01N 2333/93* (2013.01)

(58) Field of Classification Search
None
See application file for complete search history.

(56) References Cited

U.S. PATENT DOCUMENTS

| 6,573,086 B1 | 6/2003 | Emalfrab et al. |
| 2007/0173431 A1 | 7/2007 | Day et al. |
| 2008/0194005 A1 | 8/2008 | Emalfarb et al. |

FOREIGN PATENT DOCUMENTS

| CN | 1237207 A | 12/1999 |
| CN | 1330717 A | 1/2002 |
| CN | 1380905 A | 11/2002 |
| WO | 9815633 A1 | 4/1998 |
| WO | 0020555 A2 | 4/2000 |
| WO | 0179507 A2 | 10/2001 |
| WO | 2005001036 A2 | 1/2005 |
| WO | 2008073914 A2 | 6/2008 |
| WO | 2009018537 A2 | 2/2009 |
| WO | 2009033071 A2 | 3/2009 |

OTHER PUBLICATIONS

International Search Report for PCT/NL2010/000045, dated Oct. 26, 2010.

(Continued)

*Primary Examiner* — Paul J Holland

(57) ABSTRACT

The present invention provides a new fungal production system comprising a fungal host strain of *Chrysosporium lucknowense* wherein the endogenous cellulase secretion is less than 20% of the endogenous cellulase secretion of *Chrysosporium lucknowense* strain UV 18-25. Preferably, also the secretion of endogenous protease, endogenous β-glucanase and endogenous cellobiohydrolase is less than 20% of the secretion of *Chrysosporium lucknowense* strain UV 18-25. Furthermore, fungal host strains are provided wherein several genes have been disrupted. According to another aspect of the invention a method for homologous and/or heterologous production of a pure protein with a purity of higher than 75%, comprising expressing a gene encoding said protein in the strains according to the invention have been described. Furthermore, a method for production of artificial protein mixes comprising expressing a gene encoding each of said proteins in a strain according to the invention have been disclosed. Finally a method for simplified screening of strains functionally expressing a desired enzyme by application of said strains have been provided.

9 Claims, 15 Drawing Sheets

Figure 1:
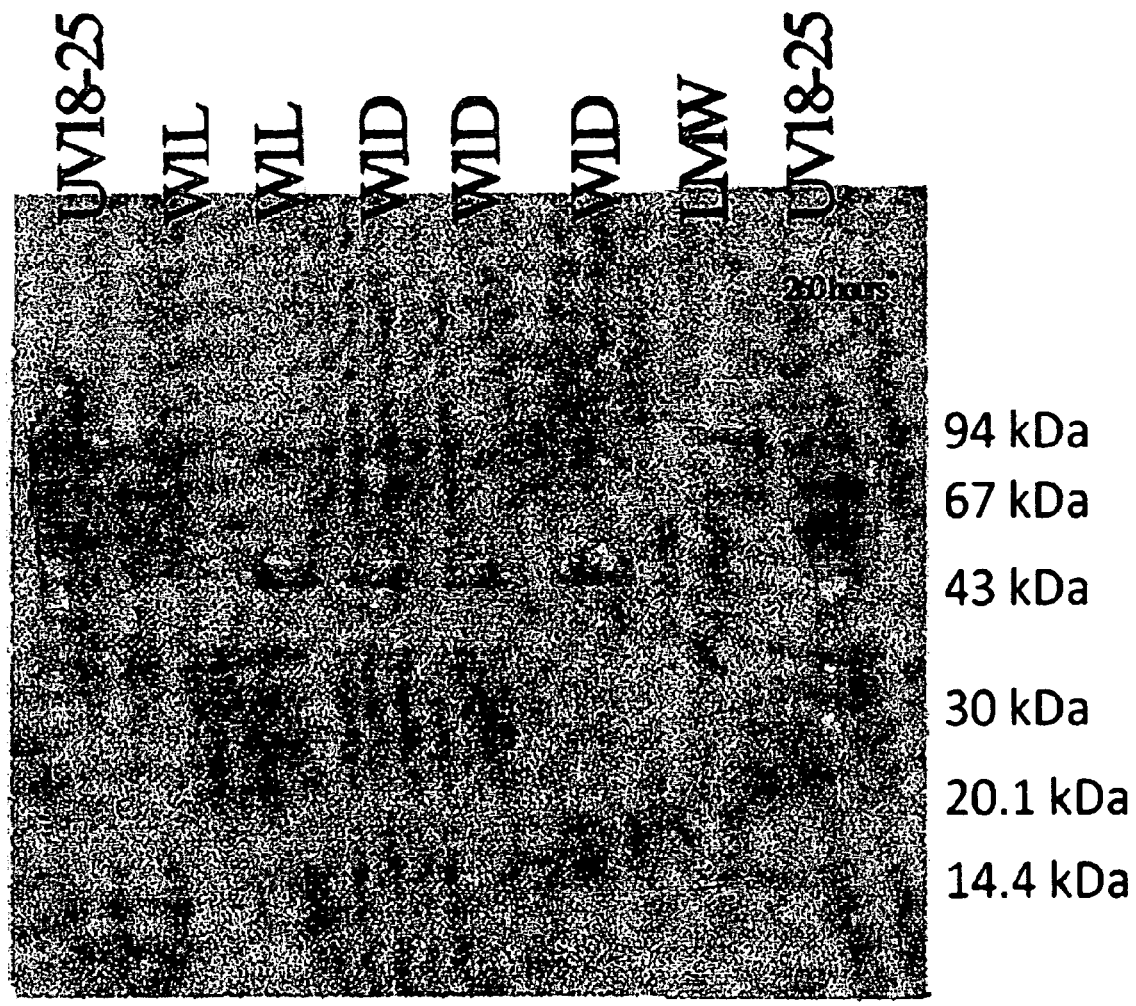

Specification includes a Sequence Listing.

(56) References Cited

OTHER PUBLICATIONS

Hinz, Sandra W.. et al., "Hemicellulase Production in Chrysosporium Lucknowense C1", Journal of Cereal Science, 50 (3):318-323 (Nov. 2009).

Hallemeersch, I. et al., "Regulation of Cellulase and Hemicellulase Synthesis in the Fungus *Chrysosporium* SP", Communications in Agricultural and Applied Biological Sciences, 68 (2):301-304 (Jan. 1, 2003).

Iverdoes, Jan C. et al., "Original Research: A Dedicated Vector for Efficient Library Construction and High Throughput Screening in the Hypha! Fungus *Chrysosporium lucknowense*", Industrial Biotechnology 3 (1):48-57 Jan. 2007).

Lever, "A New Reaction for Calorimetric Determination of Carbohydrates", Analytical Biochemistry 47:273-279 (1972).

P. Punt et al, "Fungal Protein Production: Design and Production of Chimeric Proteins", Annu. Rev. Microbiol. 65:57-69 (2011).

Search Report issued in connection with Application No. 201080020447. 5, dated Aug. 31, 2012 (in Chinese).

English translation of Office Action issued in Application No. 2010/80020447.5, dated Aug. 31, 2012.

Braaksma et al., "Aspergillus as a Cell Factory for Protein Production: Controlling Protease Activity in Fungal Production", The Aspergilli: Genomics, Medical Aspects, Biotechnology, and Research Methods CRC Press, Boca Raton, pp. 441-455 (2008).

Verdoes et al., "A dedicated vector for efficient library construction and high throughput screening in the hyphal fungus *Chrysosporium lucknowense*", Industrial Biotechnology 3:48-57 (2007).

Visser et al., "Chrysosporium lucknowense is a versatile fungal host for gene discovery and protein production", Journal of Biotechnology, Abstracts, 8211-8241 (2007 ).

FUNGAL PRODUCTION SYSTEM

This application is a divisional of application Ser. No. 13/138,661, filed Dec. 5, 2011 (now U.S. Pat. No. 9,175,296), which is the U.S. national phase of International Application No. PCT/NL2010/000045, filed Mar. 16, 2010, which claims the benefit of priority to EP Application No. 09003750, filed Mar. 16, 2009. All of these prior applications are incorporated herein by reference in their entirety.

The present invention relates to a fungal host strain of *Chrysosporium lucknowense*. The invention relates furthermore to a method for homologous and/or heterologous production of a pure protein with a purity of higher than 75%, to a method for production of artificial protein mixes and to a method for simplified screening of strains functionally expressing a desired enzyme. The invention relates furthermore to an isolated promoter sequence suitable for the transcriptional control of gene expression in *Chrysosporium lucknowense* and to a method for isolating a fungal host strain of *Chrysosporium lucknowense* wherein the protease secretion is less than 20% of the protease secretion of *Chrysosporium lucknowense* strain UV 18-25.

Fungi have been proven to be excellent hosts for the production of a variety of enzymes. Strains like *Aspergillus, Trichoderma, Penicillium* and recently the fungus *Chrysosporium lucknowense* C1, have been applied in the industrial production of a wide range of enzymes. Super-producing strains have been developed that secrete up to 100 g/L or more protein in the fermentation broth (see, for instance, in Hans Visser et al., Abstracts, *J. Biotechnol, S*211-241 (2007). The large protein-secreting capacity of these fungi make it preferred hosts for the targeted production of specific enzymes or enzyme mixes. However, typically, these hosts secrete a mix of many different enzymes, making the crude protein product undefined and yielding, besides the desired enzyme activity, a range of non-relevant or even contra-productive activities. This also holds true for the use of such fungal hosts for production of specific enzyme activities by over-expression of selected genes via genetic modification approaches. Also in these cases the target enzyme will only constitute a minor part of the total secreted protein.

A microbial production system able to secrete high amounts of a specific enzyme without the presence of high levels of other proteins would be highly desirable. It would enable simplified screening of hosts functionally expressing a desired enzyme. It would enable production of relatively pure enzyme. It would also enable simplified large scale purification of the desired enzyme. These advantages would greatly contribute to e.g., easy generation of artificial enzyme mixes tailored for different applications, e.g., plant biomass hydrolysis (biofuels and chemicals), textile finishing, applications in paper and pulp industry.

The relatively clean production of specific extracellular enzymes to high levels by micro-organisms that do not intrinsically secrete high levels of protein would be a non-preferred approach. The limited enzyme secreting capacity of such organisms would prevent high level production of the enzyme of interest.

The object of the present invention comprises the isolation of mutants of a fungal strain with high secretion capacity that unexpectedly no longer produce high levels of many non-desired proteins, while maintaining good growth characteristics, and amenability to genetic modification. These mutant strains were should be able to function as a host for high level production of specific enzymes.

In order to achieve the intended object of the invention the invention provides a fungal host strain of *Chrysosporium lucknowense* wherein the endogenous cellulase secretion is less than 20% of the endogenous cellulase secretion of *Chrysosporium lucknowense* strain UV 18-25, preferably less than 15%, more preferably less than 10%, specifically less than 5%, more specially less than 2%, more specifically less than 1%, most specifically less than 0.5%, or less than 0.1%. The strain *Chrysosporium lucknowense* strain UV 18-25 has been described in the international patent application WO 0020555. Preferably, the secretion of one or more of the group consisting of endogenous protease, endogenous β-glucanase and endogenous cellobiohydrolase of the fungal host strain according to the invention is less than 20%, more preferably less than 15%, most preferably less than 10%, especially less than 5%, more especially less than 1% most especially less than 0.5% or 0.1% of the secretion of endogenous protease, endogenous β-glucanase and endogenous cellobiohydrolase respectively of the *Chrysosporium lucknowense* strain UV 18-25. All percentages mentioned apply to the secretion of protease, β-glucanase and cellobiohydrolase independently.

Preferably the strains according to the present invention are further characterized in that secretion of endogenous cellobiohydrolase 1 (Cbh1) is absent. Most preferably the strain according to the present invention is strain W1L, deposited at the Centraal Bureau Schimmelcultures (CBS) under accession nr 122189 or W1L #100.1 deposited at the CBS under accession number 122190.

More preferably from the strains according to the present invention the gene encoding endochitinase 1 (chi1) has been disrupted. Most preferably, one or more genes selected from the group consisting of those encoding alkaline protease 1 (alp1), alkaline protease 2 (alp2), proteinase A (pepA), glucoamylase (Gla1), exo-chitinase (Chi2) and laminarinase (Lam1) have been disrupted. Especially, the strains according to the invention are W1L #100.1□alp1□pyr5 or W1L #100.1□alp1□chi1□pyr5.

The invention also relates to a method for homologous and/or heterologous production of a pure protein with a purity of higher than 75%, preferably of higher than 80%, more preferably of higher than 85, 90 or 95%, comprising expressing a gene encoding said protein in a strain according to the invention. Especially the invention provides a method for production of artificial protein mixes comprising expressing genes encoding each of said proteins of the mix in a strain according to the invention. In this way protein mixes may be prepared for different applications, e.g., plant biomass hydrolysis (bio fuels and chemicals), textile finishing, applications in paper and pulp industry). Furthermore the invention provides a method for simplified screening of strains functionally expressing a desired enzyme by application of strains according to the present invention.

According to another aspect of the invention an isolated promoter sequence is provided suitable for the transcriptional control of gene expression in *Chrysosporium lucknowense*, selected from the group consisting of (a) the chi1 (0.8) promoter comprising the nucleotide sequence of SEQ ID NO 25,
(b) the chi1 (1.8) promoter comprising the nucleotide sequence of SEQ ID NO 26,
(c) the hex1 promoter comprising the nucleotide sequence of SEQ ID NO 27,
(d) the xyl6 promoter comprising the nucleotide sequence of SEQ ID NO 28, and
(e) the gla promoter comprising the nucleotide sequence of SEQ ID NO 29 or a transcriptionally active part thereof.

Also a chimeric gene comprising said promoter sequence and a host comprising said promoter and chimeric gene are provided by the present invention.

Finally a method for isolating a fungal host strain of *Chrysosporium lucknowense* wherein the cellulase and protease secretion is less than 20% of the cellulase respectively protease secretion of *Chrysosporium lucknowense* strain UV 18-25, comprising the steps of (i) plating *Chrysosporium lucknowense* on acid swollen cellulose (ASC) plates, (ii) selecting at least one colony showing a reduced cellulose clearing zone, (iii) plating the strain selected in step (ii) on skim milk plates, and (iv) selecting at least one colony showing a reduced protein degradation halo, has been provided.

Preferably this method further comprises the steps of mutagenesis prior to steps (i) and/or (iii).

If in this patent application patent hosts are defined by comparing the level of production of various enzymes with the *Chrysosporium lucknowense* strain UV 18-25 then of course the production of one and the same enzyme in the host has to be compared with that in the *Chrysosporium lucknowense* strain UV 18-25.

The proteins mentioned in this patent application as for instance protease, β-glucanase, cellobiohydrolase, proteinase A, β-glucanase, exo-chitinase and laminarinase have been defined as described in WO 2009/0918537 in the name of Dyadic International INC.

To emphasize the advantages provided by the present invention: it relates to the isolation of novel fungal hosts that have lost their intrinsic capability to secrete high levels variety of background proteins, while retaining the ability to secrete high levels of only few enzyme activities. The invention also relates to the use of these hosts to produce specific enzymes at high levels without co-production of high levels of non-specific proteins. In addition the invention relates to the generation of defined artificial enzyme mixes tailored for different applications.

The invention will now be elucidated by the following non-limiting examples.

BRIEF DESCRIPTION OF THE FIGURES

FIG. 1: Medium samples of UVI8-25, W1L wildtype, W1D wildtype and the protease mutants W1L #100.1, W1D #50.g and W1D #100.b on SDS-PAGE. These strains were cultivated in medium #1 (low density medium with cellulose) for 282 hours except for lane 8 which is a sample in medium #2 (high density). The medium sample in lane 1 was 2 times diluted and the medium sample in lane 8 was 4 times diluted.

FIG. 2: Shake flask culture medium samples of C1 strain W1L #100.1 and derivatives. Lane 1, W1L #100.1; lane 2, W1L #100.1Δchi1; lane 3, W1L #100.1Δalp1; lane 4, W1L #100.1Δalp1Δchi1.

FIG. 3: Cosmid cloning vector pAopyrGcosarp1.

FIG. 4: Plasmid pCHI4.8. The plasmid, which was isolated from *E. coli* clone #5 is shown. This plasmid was used in the construction of the white strain gene expression vectors.

FIG. 5: Over-expression of chi1 via the introduction of extra chi1 gene copies in W1L #100.1. Lane 1, W1L #100.1 wild type strain (control); lane 3, W1L #100.1[chi+/pyr5]#3; lane 4, W1L #100.1[chi+/pyr5]#9; lane 5, W1L #100.1[chi+/pyr5]#17.

FIG. 6: Plasmid Pcbh1-glaA(II)-Tcbh1. This plasmid was used in the construction of the white strain gene expression vectors.

FIG. 7: The pPchi1(1.8)-Tcbh1 NotI gene expression vector.

FIG. 8: A schematic map of the pCRS-pPchi1(1.8)-Tcbh1 gene expression vector.

FIG. 9: SDS-PAGE analysis of culture supernatant samples of W1L #100.L Δalp1Δpyr5 (B2), and CL10518-expressing transformant strains of W1L #100.L Δalp1Δpyr5 (B3, B4). The arrow indicates the CL10518 position.

FIG. 10: SDS-PAGE analysis of culture supernatant samples of W1L #100.L Δalp1Δpyr5 (D1), and of cbh2-expressing transformant strains of W1L #100.L Δalp1Δpyr5 (D3-D5). The arrow indicates the CBH2 position.

FIG. 11: SDS-PAGE analysis of culture supernatant samples of W1L #100.L Δalp1Δchi1Δpyr5 transformed with pyr5 only (C), and of pgx-expressing transformant strains of W1L #100.L Δalp1Δchi1Δpyr5 (1, 2).

FIG. 12: SDS-PAGE analysis of culture supernatant samples of W1L #100.L Δalp1Δchi1Δpyr5 transformed with xyl1 (31, 34) and with xyl1Δcbd. The arrows indicate the protein bands representing the respective xylanase variants.

FIG. 13: SDS-PAGE analysis of culture supernatant samples of W1L #100.L Δalp1Δchi1Δpyr5 transformed with med with selection marker only (71) and with abn2 (68-70), M, marker.

FIG. 14: Analysis of chi1 transformants. #1, control strain (transformed with selection marker pyr5 only). M, marker. #65, chi1 transformant. The arrow marks the Chi1 protein band.

FIG. 15: Protein gel of purified heterologous *Aspergillus* niger PGII produced by C1. M, Marker proteins. The molecular weights of 3 marker proteins are indicated to the left of the gel. Lane 1, purified PGII.

EXAMPLES

Example 1

Isolation of C1 Mutants with Greatly Reduced Cellulase Activity (White Strains)

C1 strain UV18-25 (described in WO/2000/020555) was mutated using UV light to produce the strain UV26-2 (Appendix 1 to the Examples). UV26-2 exhibited large clearing zones on ASC (acid swollen cellulose) plates, indicating overproduction of cellulase.

UV26-2 was not a stable mutant and successive streaking of UV26-2 resulted in generation of cellulase negative mutants as shown by the absence of clearing zones on ASC plates. These colonies exhibited enhanced sporulation and white color, while normal, cellulase-producing, colonies were cream colored and showed no sporulation on ASC plates.

Two white colonies (UV26-2W1 and UV26-2W2) were picked from ASC plates along with two normal colonies and cellulase production was evaluated using a shake flask screening procedure. The white colonies produced 6 and 4 U/ml of AzoCMC cellulase activity, while the two normal colonies produced 278 and 294 U/ml of cellulase activity. This confirmed the white colonies to be cellulase-negative mutants.

Example 2

Isolation and Analysis of Protease Deficient Strains of UV26-2W1L and UV26-2W1D

The purification of strain UV26-2W1 on RM-ASP medium plates (Appendix 2 to the Examples) resulted in the identification of 2 types of colonies: colonies with light colored spores like UV 18-25 (UV26-2W1L further indicated as strain W1L), and colonies with dark (pink) colored spores (UV26-2W1D further indicated as strain W1D).

In additional experiments batches of spores of both W1L and W1D were irradiated with UV (Appendix 1 to the Examples) and used in a direct selection procedure for protease-deficient mutants (Braaksma et al., 2008). Positive clones were analyzed on skim milk plates for their protease activity.

After several rounds of purification and selection on skim milk plates, two mutants of W1L (W1L #50.c and W1L #100.1) and three mutants of W1D (W1D #50.g, W1D #50.n and W1D #100.b) with a reduced halo on skim milk plates were selected for cultivation for in vitro degradation assays. In a first cultivation experiment these mutants and their parent strains were cultivated in medium #2 Appendix 1 to the Examples) for 240 hours at 35° C. Apparently, the low cellulase activity in these strains did not allow for growth in high density cellulose based medium. In following cultivation experiments W1L #50.c, W1L #100.1, W1D #50.g and W1D #100.b and their parents were grown in low (#1) and high (#2) density cellulose medium for 240 hours at 35° C. Also UV18-25 was taken as a control. The parent strains 2W1D, 2W1L and UV 18-25 were also cultivated in medium #2. None of the W1L or W1D strains grew in high density cellulose medium #2. In medium #1 good growth could be observed for the 'white' strains and their protease-deficient mutants, although the cellulose in the medium was hardly used by the 'white' strains. Unexpectedly, it was noted that the UV26-2W1D parent strain, which showed an unstable growth phenotype on agar plates, did use the cellulose in the medium.

The medium samples of the W1L parent strain showed less protease activity on skim milk plates compared to medium samples of W1D parent strain and UV 18-25 (Table 1). This is contrary to what was observed when the strains were grown directly on skim milk plates. In that case a large halo could be detected around the colony of UV18-25 and of W1L after 72 hours growth at 30° C., while a small halo could only be detected after 144 hours for W1D. The medium samples of protease mutant W1D #50.g showed a smaller halo on milk plates until 162 hours of cultivation. After 186 hours cultivation, halos were similar as observed for its parent strain.

TABLE 1

Medium Analysis of W1L and W1D Parent Strains and their Selected Protease Mutants

| Strain | RELATIVE HALO SIZE (hrs of cultivation) | | | | | | | PROTEASE ACTIVITY U/ml |
|---|---|---|---|---|---|---|---|---|
| | 114 | 138 | 162 | 186 | 210 | 240 | 282 | |
| W1L parent | ++ | ++ | ++ | ++ | ++ | ++ | ++ | 943 |
| W1L#100.1 | + | +++ | +++ | +++ | +++ | +++ | +++ | 119 |
| W1L#100.1 Δalp1 | nd | nd | nd | nd | nd | nd | nd | 46 |
| W1D parent | +++ | +++ | +++ | +++ | +++ | +++ | +++ | nd |
| W1D#50.g | − | − | − | ++ | ++ | ++ | ++ | nd |
| W1D#100.b | ++ | ++ | ++ | ++ | ++ | ++ | ++ | nd |
| UV18-25 | +++ | +++ | +++ | +++ | +++ | +++ | +++ | nd |

W1L#100.1, W1D#50.g and W1D#100.b. UV18-25 was taken as control. Protease activities of medium samples of W1L, W1L#100.1 and W1L#100.1Δalp1 were also determined. These strains were cultivated in medium #1 (low cellulose/lactose/pharmamedia). The pH was measured and medium was spotted on skim milk plates to determine their protease activity. The relative size of the halo is a measure for the protease activity in the medium.
nd, not determined.

Analysis of 282 hours medium samples of these strains on SDS-PAGE gels showed that the 'white strains' produced much less protein than UV 18-25 (FIG. 1). In particular the two major 50/70 kDa proteins (Cbh1) were absent in these culture supernatants. In the white strains the 'major' proteins are 75 and 45 kDa. These proteins are present in medium of UV18-25 as minor proteins.

From this first screening for protease-less mutants in a UV26-2W1 background the strains W1D #50.g and W1L #100.1 were selected for further analysis.

Example 3

Comparison of Extracellular Enzyme Activities Between UV18-25 and W1L #100.1

Different enzyme activities in the extracellular protein content of UV 18-25 and W1L #100.1 samples were determined (Table 2). Based on these data it was concluded that W1L #100.1 secretes very little specific cellulase activity (less than 1% of UV 18-25) and has very little or no detectable protease activity when compared to UV 18-25.

TABLE 2

Specific activities of samples (U/mg of protein).

| Activities | UV18-25 | W1L#100.1 |
|---|---|---|
| CMCase (cellulase) | 6.20 | 0.04 |
| Beta-glucanase | 10.2 | 0.53 |
| Cellobiohydrolase | 0.72 | 0.09 |
| Protease* (pH 5) | 0.06 | 0.03 |
| Protease (pH 7) | 0.05 | 0.00 |
| Protease (pH 9) | 0.04 | 0.00 |

*Protease activities were measured at 3 different pH values.

In addition, the levels of hydrolases bearing other substrate specificities (e.g., hemi-cellulose) were reduced as well.

Example 4

Further Reduction of Protein Level: Identification of Major Proteins

As described above, the white strain is missing the extracellular cellulolytic enzyme spectrum when compared to its parental strain. Hence, the extracellular protein content in white strain cultures, as analyzed by SDS-PAGE, is low.

This strain characteristic is beneficial with regard to protein production and purification, since the relative amount of any target protein expressed in such strain will be high. Furthermore, the (nearly) absence of cellulase activity makes the white strain an ideal host strain for testing new or modified cellulases. The same is valid for xylanases as no major xylanase activity was detectable.

To further reduce the protein background level, several major protein bands present in an SDS-PAGE gel from a W1L #100.1 and derivative strain cultures were excised and identified by N-terminal sequencing and/or MS-MS analysis. The most abundant protein was the endochitinase Chi1 (gene identifier: CL06081, peptides MVYDYAG (SEQ ID NO:9), MPIYGRS (SEQ ID NO:11), and MFXEASA (SEQ ID NO:14). Other major proteins were identified as a glucoamylase (Gla1, CL09507, peptides TGGWSVVWPVLK (SEQ ID NO:1) and VVGSSSEL(I)GNWDTGR (SEQ ID NO:2)), exo-chitinase (Chi2, CL00367, peptides TIDAMAWSK (SEQ ID NO:3), NFLPVADILR (SEQ ID NO:4), GAYHPSQTYSPEDVEK (SEQ ID NO:5), and SWQLVYQHDPTAGLTAEEAK (SEQ ID NO:6) and a laminarinase (Lam1, CL08253, peptides PQYESAGSV-VPSSFLSVR (SEQ ID NO:7) and VSGQVELTD-FLVSTQGR (SEQ ID NO:8). Also an alkaline protease Alp1 (CL04253) has been identified in W1L #100.1 culture broth. Alp1 degrades extracellular proteins, and may degrade proteins of interest.

Example 5

Further Reduction of Protein Level: Disruption of the Chi1, Chi2, Gla1 and Lam1 Genes The vector pChi3-4 (see Example 9, Isolation of the endochitinase 1 encoding gene) was used for the construction of the gene disruption vector. A 1.1-kb MscI/StuI fragment was replaced with the amdS-rep selection marker or the pyr5-rep selection marker, resulting in the vectors pΔchi1-amdS and pΔchi1-pyr5, respectively. The disruption fragment Δchi1-amdS was isolated from pΔchi1-amdS by digestion with EcoRI. The disruption fragment Δchi1-pyr5 was isolated from pΔchi1-pyr5 by digestion with SmaI. Transformation of strain W1L #100.1Δpyr5#172-12 using the disruption fragments resulted in 215Δchi1-pyr5 transformants and 32Δchi1-amdS transformants. All the obtained transformants were purified and analyzed with colony hybridization. Southern analysis of these transformants confirmed the isolation of one W1L #100.1 transformant with a disrupted chi gene (W1L #100.1Δpyr5Δchi1-pyr5#46 (pyr5+)).

Figure 2:
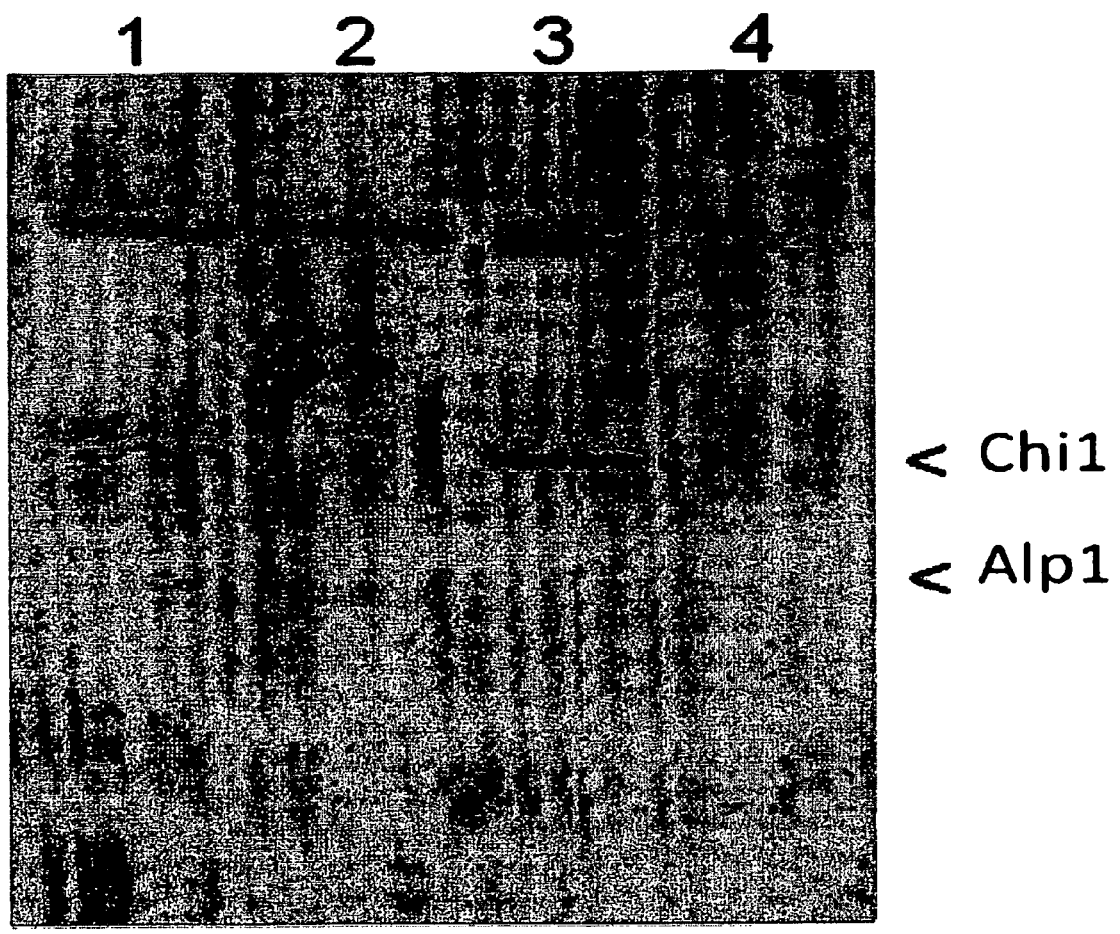

Shake flask cultures on C1 low density medium were performed from a selection of W1L #100.1Δpyr5Δchi1 mutant strains. The samples were analyzed on SDS-PAGE to evaluate the protein profiles for absence of Chi1 protein (FIG. 2, lane 2 versus lane 1). As shown no 45 kDa Chi1 protein is observed in the Δchi1 mutant strain.

The remaining most prominent extracellular proteins in white strain W1L #100.1Δalp1Δchi1 and derivative strains correspond to glucoamylase (Gla1), exo-chitinase (Chi2) and laminarinase (Lam1). These enzymes were purified from the culture medium. The enzymatic activities of these proteins were verified using (among others) starch, chitosan and laminarin, respectively, as substrates. Furthermore, mass spectrometry analyses data (see Example 4) combined with C1 genome sequence data revealed the corresponding genes. In order to further reduce the extracellular protein background, the Gla1, Chi2, and Lam1 encoding genes were disrupted and thereby inactivated. Disruption was based on the exchange of the gene promoter and part of the 5' coding sequence by an amdS selection marker via homologous recombination using approximately 1.5 kbp upstream and downstream sequences that flank these gene promoter and part of the 5' coding sequence. The gene disruption vectors therefore contained the amdS expression cassette plus these flanking 1.5 kb homologous gene sequences. White strains W1L #100.1Δalp1Δchi1 and derivative strains were transformed with the gla1, Chi2 and lam1 gene disruption vectors and transformants were screened for the correct genotype using PCR. As such, white strains with a further reduced extracellular protein composition/content were obtained. Target proteins produced by these strains were more than 80% pure in the crude cell-free culture liquid.

Example 6

Further Reduction of Protease Activity: Targeted Disruption of Genes Encoding Proteases In general, protease encoding genes were disrupted using disruption DNA fragments that contained selection markers (amdS, pyr4 or pyr5) flanked by approximately 1.5 kb large DNA fragments homologous to regions up- and downstream of the gene to be disrupted. Upon introduction of these disruption DNA fragments into the white host, an homologous recombination exchanged the gene to be disrupted for the selection marker fragment. Corresponding transformants were selected as such. Genes that were disrupted this way either encoded disadvantageous (with regard to target protein stability) protease activities e.g., alp1, alp2, pep4) or significant background protein (chi1) or were to be used as selection marker (pyr4, pyr5). Via this approach numerous white C1-strains have been constructed that can be used as hosts for target protein expression (Table 3).

TABLE 3

| Strain W1L and derivatives. |
| --- |
| W1L |
| W1L SUI$^R$ #S2 6.14 |
| W1L SUI$^R$ #S2 6S |
| W1L#100.1 |
| W1L#100.1 Δpyr5 |
| W1L#100.1 Δalp1 |
| W1L#100.1 Δalp1 Δpyr5 |
| W1L#100.1 Δpep4 Δpyr5 |
| W1L#100.1 Δalp1 Δpep4 |
| W1L#100.1 Δalp1 Δpep4 Δpyr5 |
| W1L#100.1 Δalp1 Δalp2 Δpyr5 |
| W1L#100.1 Δchi1 |
| W1L#100.1 Δalp1 Δchi1 |
| W1L#100.1 Δalp1 Δchi1 Δpyr5 |
| W1L#100.1 Δalp1 Δchi1 Δalp2 |
| W1L#100.1 Δalp1 Δchi1 Δalp2 Δpyr5 |
| W1L#100.1 Δalp1 Δchi1 Δpep4 |
| W1L#100.1 Δalp1 Δchi1 Δgla1Δlam1Δchi2Δpyr5 |

Example 7

Identification of Strong Promoters for Gene Expression: Chitinase Encoding Gene (chi1)

Several major protein bands were isolated from fermentation samples of W1L #100.1 grown in low density cellulose medium in order to identify and isolate strong promoters that can be used for gene expression in the W1L strain and its derivatives. N-terminal sequencing of a mixture of peptides obtained after CNBr treatment of the major 45 kDa protein of W1L #100.1 resulted in the identification of four different peptides. Three of these peptides (MVYAG MVYDYAG (SEQ ID NO:9), MPIYGRS (SEQ ID NO:11) and MFXEASA (SEQ ID NO;14) showed homology with an endochitinase of Aphanocladium album/*Trichoderma harzianum* (CHI_APHAL P32470).

Based on 3 of these peptide sequences, primers were designed in order to obtain PCR fragments containing a part of the endochitinase encoding gene (Table 4). The PCR primers were designed based on the preferred codon usage of C1.

TABLE 4

The designed primers of putative endochitinase based on codon usage of C1.

| Primer | Region | Position | Deduced sequence |
|---|---|---|---|
| Endochitpep 1C | MVYDYAG (SEQ ID NO: 9) | 240 aa | ATGGTSTACGACTA CGCBGG (SEQ ID NO: 10) |
| Endochitpep 2C | MPIYGRS (SEQ ID NO: 11) | 290 aa | ATGCCSATCTACGGYCG (SEQ ID NO: 12) |
| Endochitpep2 revC | | | CGRCCGTAGATSGG CAT (SEQ ID NO: 13) |
| Endochitpep3 revC | MFXEASA (SEQ ID NO: 14) | 380 aa | GCSSWVGCCTCCCAGAACAT (SEQ ID NO: 15) |

Primer based on a conserved homologous region of endochitinase:

| | | | |
|---|---|---|---|
| Endochit3c | DGIDIDWEV (SEQ ID NO: 16) | 160 aa | GAYGGYATCGAYRTSG AYTGGG (SEQ ID NO: 17) |

PCR reactions with these primers were carried out using chromosomal DNA of UV 18-25 as template DNA. PCR fragments were cloned and sequence analysis showed that one of the cloned PCR fragments obtained with Endochitpep1c and Endochitpep2revc (173 bp) contained a part of an endochitinase-encoding gene (chi1). Hybridization analysis of chromosomal DNA of UV18-25 digested BamHI and HindIII with this chi1 fragment as probe showed a clear hybridization signal confirming that the PCR fragment originated from C1 DNA. This fragment was used to clone the complete gene from the ordered C1-cosmid gene library. The fragment sequence (SEQ ID NO:18) was as follows:

```
ATGGGCTACGACTACGCCGGCTCGTGGAGCACCGCGGCGGGACACCAG

GCCAACCTGTACCCGACCGCCGACGCGGGCAGGACGCCCTTCTCGACC

GACAAGGCCCTGTCCGACTACGTCGCCGCCGGCGTCGACCCGGCCAAG

ATCGTGCTCGGCATGCCCATCTACGGCCG
```

Example 8

Construction of an Ordered Cosmid Library of *Chrysosporium Lucknowense* UV18-25 in *E. coli*

Figure 3:
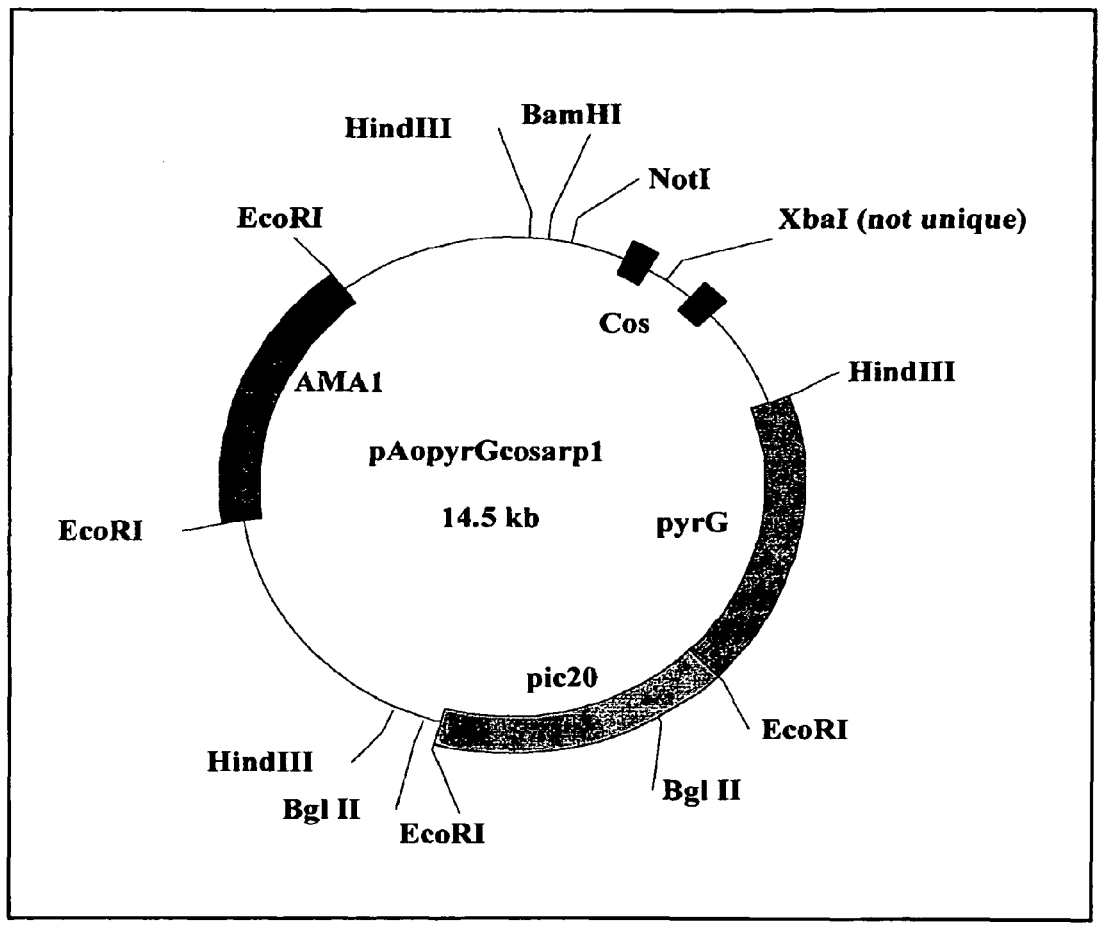
Figure 4:
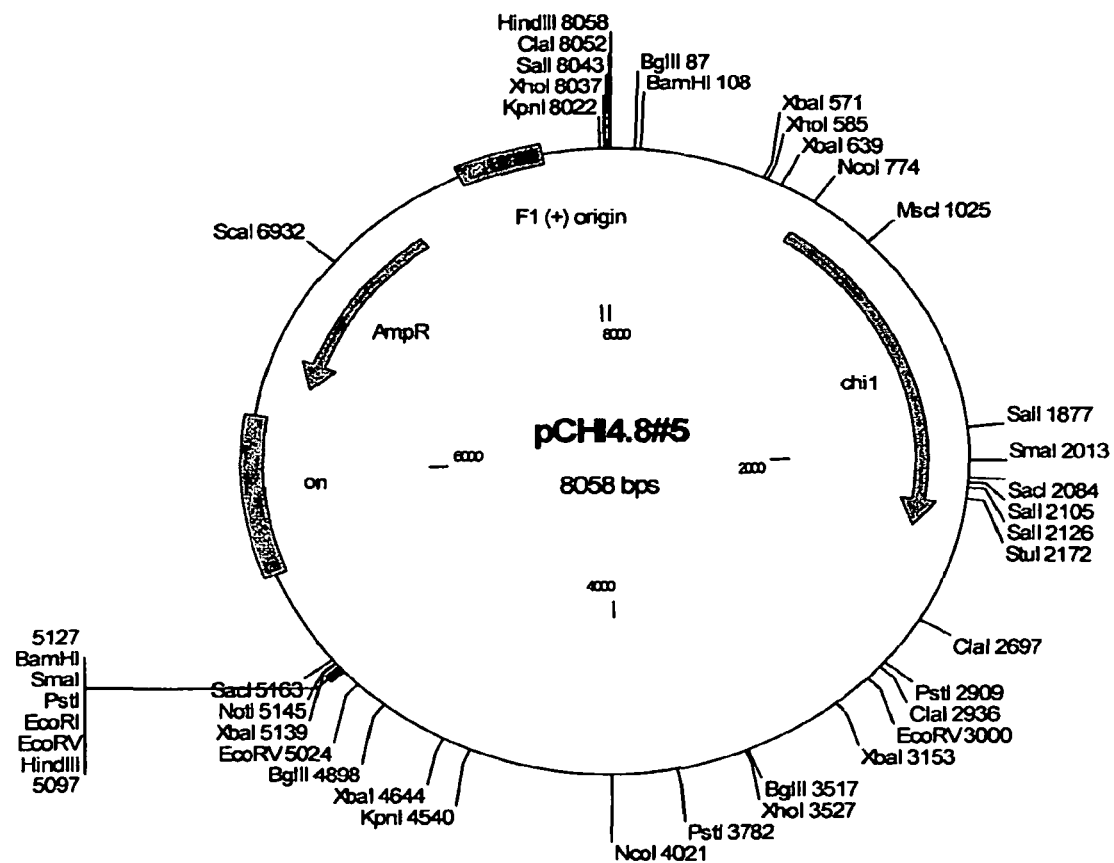
Figure 5:
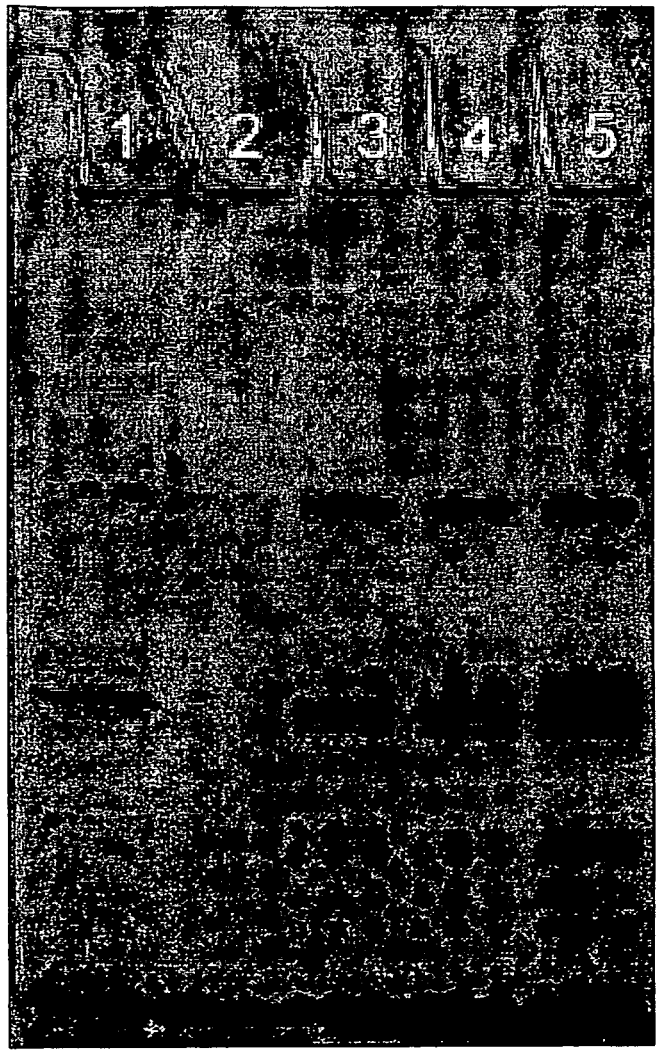

For the construction of the C1 cosmid library the non commercial cosmid cloning vector, pAOpyrGcosarp1 (FIG. 3) was used. This vector carries the *Aspergillus oryzae* pyrG selection marker allowing transformation of a wide range of fungal strains. Moreover, for highly efficient transformation of various *Aspergillus* species (for which a large collection of mutant strains is available for complementation cloning of the corresponding C1 gene) the AMA 1-replicator is present in this vector. A unique BamHI cloning site allows cloning of partially Sau3A digested genomic DNA from *Chrysosporium* strain UV 18-25.

A cosmid library of UV 18-25 was constructed in *E. coli* and stored as glycerol stocks in the −80° C. The average insert size was 20-35 kb. In total, 6800 clones were obtained, which represents a genome coverage of about 5 fold. To order these clones in 384-wells plates, dilutions of the glycerol stocks were plated on LB-agar plates, containing ampicillin. 7680 individual colonies were manually picked and inoculated in twenty 384-wells plates. These twenty 384-wells plates represent the ordered cosmid library of UV 18-25 in *E. coli.*

The individual colonies in the twenty 384-wells plates were spotted on nylon filters (Hybond), using a Staccato 384-pintool (Zymarks). The ordered cosmid library was spotted in octuplicate (in total 160 filters). These filters were placed on LB-ampicillin medium plates and incubated at 37° C. to allow colonies to grow on the filters. Subsequently, the colonies were lysed and the cosmid DNA was bound to the filters using standard procedures.

Example 9

Isolation of the Endochitinase 1 Encoding Gene (chi1)

The 173-bp chi1 PCR fragment was used as a radio-active labeled probe for hybridization of duplicate filters of the cosmid library. Hybridization of the cosmid gene library using this chi1 fragment resulted in 3 positive clones. DNA was isolated from these clones and restriction analysis followed by Southern analysis was carried out. A 4.8 kb HindIII fragment and a 3.4 kb BglII fragment showed hybridization using the chi1 probe. The 4.8 kb HindIII and 3.4 kb BglII fragments containing the chi1 gene were isolated and subcloned in pMTL24, resulting in the vectors pCHI4.8 (FIG. 4) and pChi3-4, respectively. Subsequently, a BglII sub-clone was used for sequence analysis to obtain more sequence data. The sequence of the complete chi1 gene of UV 18-25 was obtained. The size of the chi1 gene is 1529 bp in which 2 introns of 111 bp and 138 bp are present.

Example 10

Overexpression of the Endochitinase in W1L #100.1

For overexpression of endochitinase the 3.4 kb BglII fragment containing the chi1 gene was isolated from pChi3-4. Putative chi1 multi-copy strains in W1L #100.1Δpyr5 were generated by co-transformation of the 3.4 kb BglII chi1 fragment and a pyr5 selection fragment and correct transformants were confirmed by colony hybridization. Shake-flask cultures on C1 low density medium were performed from a selection of W1L #100.1 chi1-multicopy strains. The samples were analyzed on SDS-PAGE to evaluate the protein profiles for the overproduction of Chi1 (FIG. 5). Three of the multi-copy chi1 strains (lanes 3, 4, 5) show a stronger 45 kDa band compared to the parent strain (lane 1) indicating chitinase overexpression and the usefulness of the chi1 promoter for high gene expression.

Figure 6:
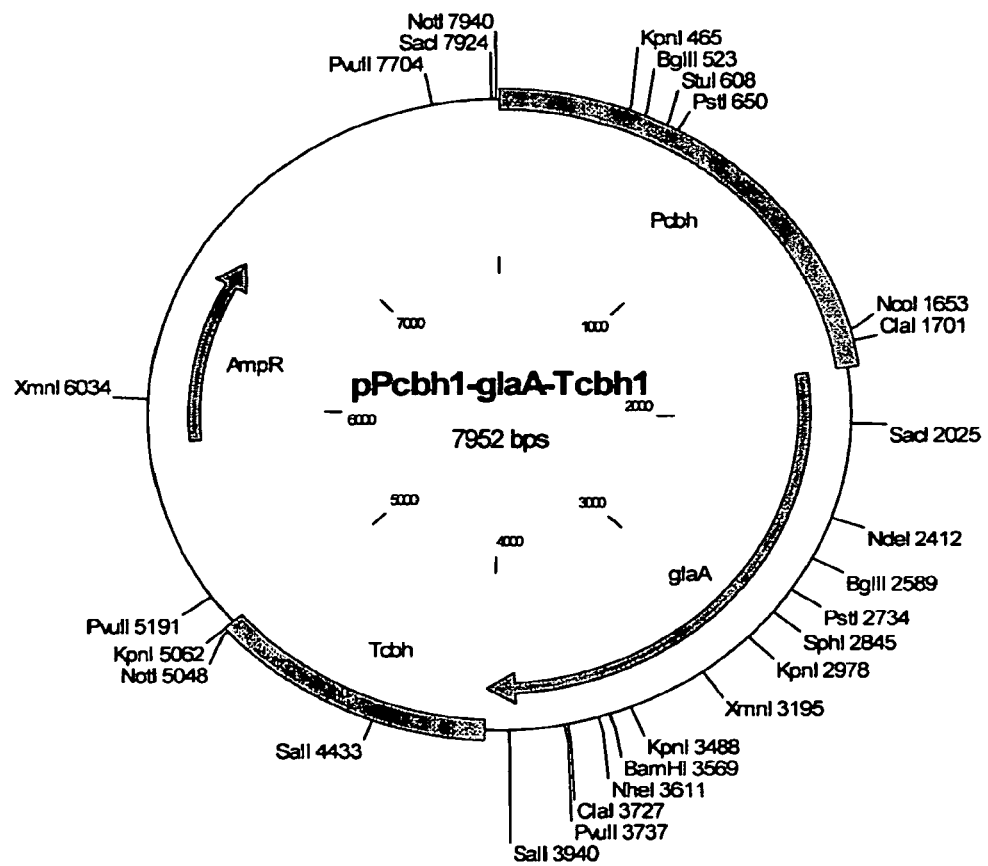

Therefore, a general C1 expression cloning vector (pPchi1(0.8)-Tcbh1 NotI) was constructed containing the chi-promoter (Pchi) to direct the overexpression of cloned genes. Initially, the EcoRI site upstream op Pchi1 in pCHI #4.8 was removed by a partial EcoRI digestion and treatment of the linear fragment with Klenow yielding pCHI1#4.8ΔEcoRI. From this vector the 1.9-kb SacI-SphI fragment was cloned in the corresponding site of pPcbh1-glaA(II)-Tcbh1 (FIG. 6). In the resulting vector, pPchi-Tcbh1 NotI #7.1, the target genes can be inserted into the NcoI-EcoRI sites. Expression cassettes for transformation into C1 strains can be isolated from these constructs as NotI fragments.

Figure 7:
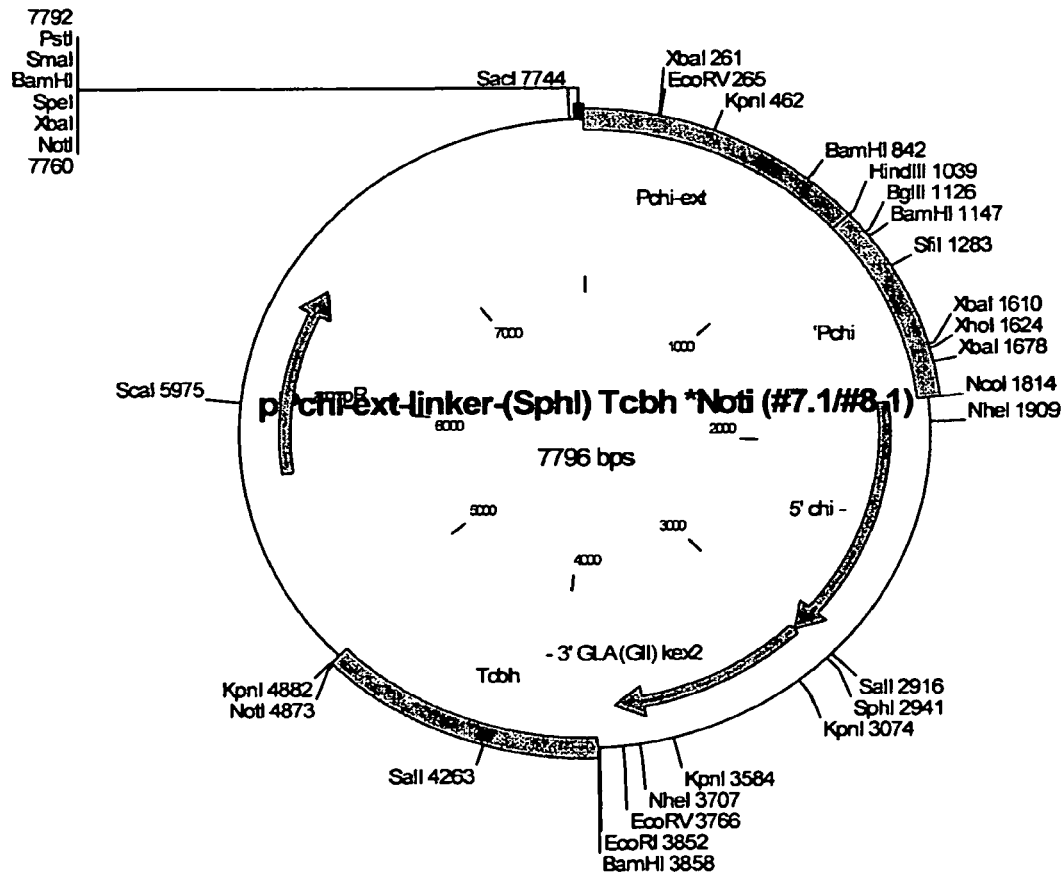

The 0.8 kb chi1 promoter sequence in pCHI #4.8 could be more than sufficient to drive chi1 expression. However, a longer chi1 promoter was also generated by amplifying the a PstI-HindIII fragment (upstream of the HindIII site at position −775 relative to the ATG start codon), using one of the previously identified positive cosmid clone as template DNA. The resulting fragment was cloned in pGEM-T-Easy and sequenced. From this plasmid the PstI-HindIII fragment was isolated and cloned in the corresponding sites of pPchi1-xyl1-Tcbh1 yielding pPchi1(1.8)-xyl1-Tcbh1, in which the promoter size is 1.8 kb. The fragment was also cloned in the corresponding site of pPchi1-Tcbh1 NotI #7.1, yielding the general expression vector pPchi1(1.8)-Tcbh1 NotI (FIG. 7).

The levels of gene expression directed by the extended chitinase promoter (Pchi1(1.8)) and by the initially used chitinase promoter (Pchi1 (0.8)) were compared by the expression of two reporter genes, xyl1 and apl1. White strain transformants were generated that either expressed xyl1 (encoding a xylanase) or apl1 (encoding an alkaline protease) (Table 5).

TABLE 5

Comparison of the short and extended Pchi1promoters in terms of reporter protein expression level.

| Reporter | 0.8 kb Pchi1 Reporter activity | 1.8 kb Pchi1 Reporter activity |
|---|---|---|
| Alp1 (R19) | 0.7 (A)* | 1.9 (B)* |
| Xyl1 (R14) | 122 (C)* | 1175 (D)* |

Reporter activity: xylanase activity is expressed as U/ml and alkaline protease activity as U/mg of protein.
*A = W1L#100.1[Pchi1(0.8)-alp1/pyr5]#9,
*B = W1L#100.1[Pchi1(1.8)-alp1/pyr5]#22,
*C = W1L#100.1Δalp1[Pchi1-xyl1]#95,
*D = W1L#100.1Δalp1[Pchi1(1.8)-xyl1]#A7.

Surprisingly, the reporter gene expression was higher in case of the extended chi1 promoter (1.8 kb), which indicates the necessity of the further upstream regions. In conclusion, a Pchi1 based expression system was developed for high level expression of genes in White C1 strains.

Example 11

Identification of Other Strong Promoters for Gene Expression

A different approach for searching strong promoters was performed using the quantitative detection of messenger RNA levels from W1L or WI L #100.1 RNA. The RNA samples were isolated from mycelium which was sampled at different time points during a fed-batch fermentation process. A number of genes were identified as being strongly or stronger expressed. To verify the expression level of these genes, the RNA samples were also separated on gel, blotted and hybridized to probes specific for these genes (Table 6).

TABLE 6

Quantification of the expression signals of the different genes in controlled fed-batch fermentations.

| Strain/feed | chi1 | pep4 | his2a | hex1 | bgl1 | xyl6 | cbh1 |
|---|---|---|---|---|---|---|---|
| W1L/glucose Batch | 0 | 4 | 2 | 21 | 0 | 0.3 | 0 |
| Day 1 feed | 47 | 5 | 3 | 15 | 8 | 1 | 0 |
| Day 2 feed | 52 | 3 | 3 | 17 | 8 | 1 | 0 |
| W1L#100.1/xylose Batch | 0 | 0.2 | 2 | 12 | 0 | 0 | 0 |
| Day 1 feed | 40 | 3 | 2 | 12 | 3 | 19 | 0 |
| Day 2 feed | 36 | 4 | 6 | 17 | 5 | 21 | 0 |
| W1L#100.1/glucose Batch | 0 | 0.1 | 3 | 23 | 0 | 0.1 | 0 |
| Day 1 feed | 61 | 0.5 | 2 | 17 | 7 | 0.2 | 0 |
| Day 2 feed | 59 | 0.2 | 2 | 14 | 6 | 1 | 0 |

Probe hybridisation signals were quantified using a densitometer. The signal of the probe on the Northern blot was correlated with the signal of this probe on a C1 genomic DNA Southern blot. Therefore, the values in the table represent the northern hybridization signal level relative to the hybridization signal level from the Southern blot (which was set at 1). Gene sequences are given below.

The cbh1 promoter, which is a strong promoter in UV 18.25 strains, is not active in the white strains. The chi1 promoter was the strongest both under glucose and xylose feed conditions. The hex1 promoter is a strong constitutive promoter during all phases of fermentation and under both sugar feed conditions. The xyl6 promoter is highly active under the xylose feed condition only. The pep4, his2a and bgl1 promoters are moderately active. For high level gene expression in the white strains the chi1, hex1 and xyl6 promoters are very useful. Alternative promoters that also give high expression are those of the pep4, his2a and bgl1 genes. Additional northern experiments also indicated that the promoters of the xyl4 and xyl8 genes can be used for high level gene expression in the white strains when grown on xylose. Glucoamylase (Gla1, gene identifier: CL09507) has been shown to be a major protein in white C1 strains. The gla1 promoter is therefore also a good candidate to be used for the high level expression of genes of interest in white strains. It was shown that glucoamylase was highly abundant in a white strain grown in the presence of starch. This indicated that the gla1 promoter is strong and inducible by starch and its degradation products, like maltose.

The nucleotide sequences of Pchi1(0.8), Pchi1(1.8), Phex1, Pxy16 and Pgla1 are given below. Note that the ATG start codons of the corresponding coding regions are given in bold italics.

Example 12

White Strain Gene Expression System

Figure 8:
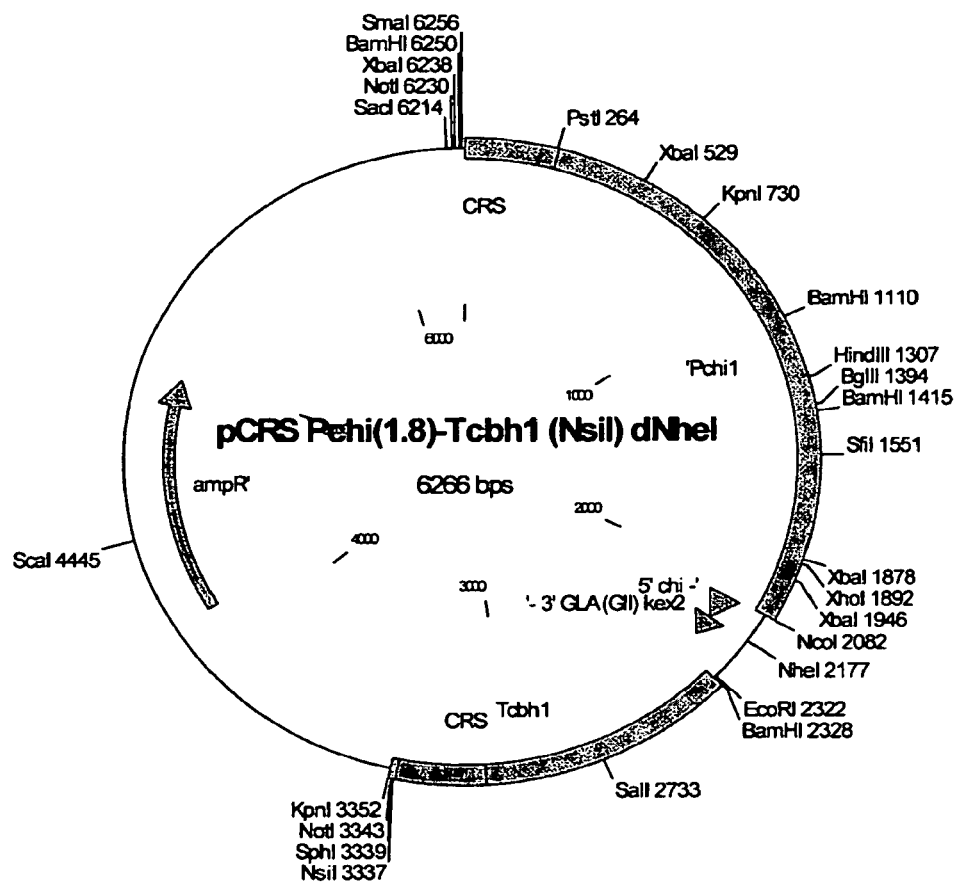

Two expression vectors were designed for expression of genes in W1L and derivatives: pPchi1(1.8)-Tcbh1 Not1 was as described above. Additionally, pCRS Pchi1-Tcbh1 (FIG. 8) was constructed by placing the C1 repeat sequence in front of the Pchi1 promoter in pPchi1(1.8)-Tcbh1 NotI. These vectors have been designed in such a way that they also can be combined resulting in a single vector that contains multiple expression cassettes. The multiple cassettes can be excised from the vector as a single linear DNA fragment.

Many genes have been cloned and expressed in W1L or derivatives. The general procedure was as follows: Genes were identified by purification and characterization of the gene products (reverse genetics) and/or by genome mining. The genes were amplified by PCR or synthesized chemically. Amplification of genes by PCR was performed by using proof-reading PCR DNA polymerases (Phusion or Supertaq plus). The amplified genes were cloned into PCR cloning vectors i.e. pGEM-T-Easy (Promega) or pJet1 (Fermentas) and sequenced to verify the correctness of the sequence. Subsequently, the genes were released from the PCR cloning vector and ligated into the NcoI and EcoRI sites of the expression vector(s).

Special care was taken when designing the PCR primers. The ATG-start codon of the gene to be expressed was part of the NcoI restriction site in the white strain expression vectors. Therefore, the 5' (ATG) PCR primers contained restriction sites, which are compatible to the restricted NcoI site of the vector. These sites were i.e., NcoI itself (C ICATGG), or compatible sites that are cut within the recognition site (BspHI, T↓CATGA; PciI, A. ↓CATGT), or compatible sites that are cut outside the recognition site (BsaI, GGTCTC(1/5); BspMI, ACCTGC(4/8); Esp3I, CGTCTC(1/5)).

In some cases, restriction sites additional to those that were going to be used for cloning of the genes were encountered in the genes. In these cases, the genes were amplified by fusion PCR, where the fusion of the two PCR fragments was selected to take place at the undesired additional restriction site. The undesired restriction site was removed by using fusion primers containing single substitution mutations in the undesired restriction site sequence. In case the undesired restriction site was present within a protein coding region, the substituted nucleotide was selected in such a manner that the mutant codon encoded the same amino acid as the original codon.

The expression cassettes were released from the E. coli DNA vector backbone by NotI restriction. The expression cassette was subsequently transformed in to W1L derivatives simultaneously with a selection marker i.e. pyr5 or amdS in co-transformation experiments.

Positive and high producing transformants were selected by SDS-PAGE or enzyme assay analysis of the growth medium. Best producers were applied in fermentations to produce high amount of the desired gene product.

The following proteins have been produced using the white strain gene expression system and corresponding genes In the international patent application WO 2009/018537 has been described:

Abf1, Abf2, Abn1, Axe1, Bgl1 (=Bgl3A), Cbh1, Cbh2, Cbh4, Chi1, Eg2, Eg5, FaeA1, FaeA2, FaeB2, Gal1 (=Gal53A), Gla1 (=Gla15A), Pme1, Xyl1, Xyl1(cd), Xyl2, Xyl3, Xyl3-cbd (=xyl3(cd)), Xyl4, Xyl5, Xyl6.

In the international patent application WO 2009/033071 has been described:

Abf3, Abn2, Abn3, Abn4, Abn5, Abn7, Abn9, Agu1, Axe2, Axe3, Bga2, Bxl1, Bxl2, Abf5 (formerly known as Bxl3), GH61 genes (gene identifiers: CL09768, CL10518, CL05022, CL04725, CL04750, CL06230, CL05366), Gln, Pgx1, Rga1, Rgx1, Xgl1, Xyl7, Xyl8, Xyl9, Xyl10, Xyl11.

Alp1: The Alp1 DNA sequence is given by SEQ ID NO 30. The Alp1 amino acid sequence is given in SEQ ID NO 31.

The apl1 gene was expressed and Alp1 showed protease activity (Table 5). The "Protease colorimetric detection kit" (Sigma, product number PC0100) was used to determine Alp1 protease activity.

Example 13

Expression of C1 GH61-Family-Encoding Proteins Genes

Figure 9:
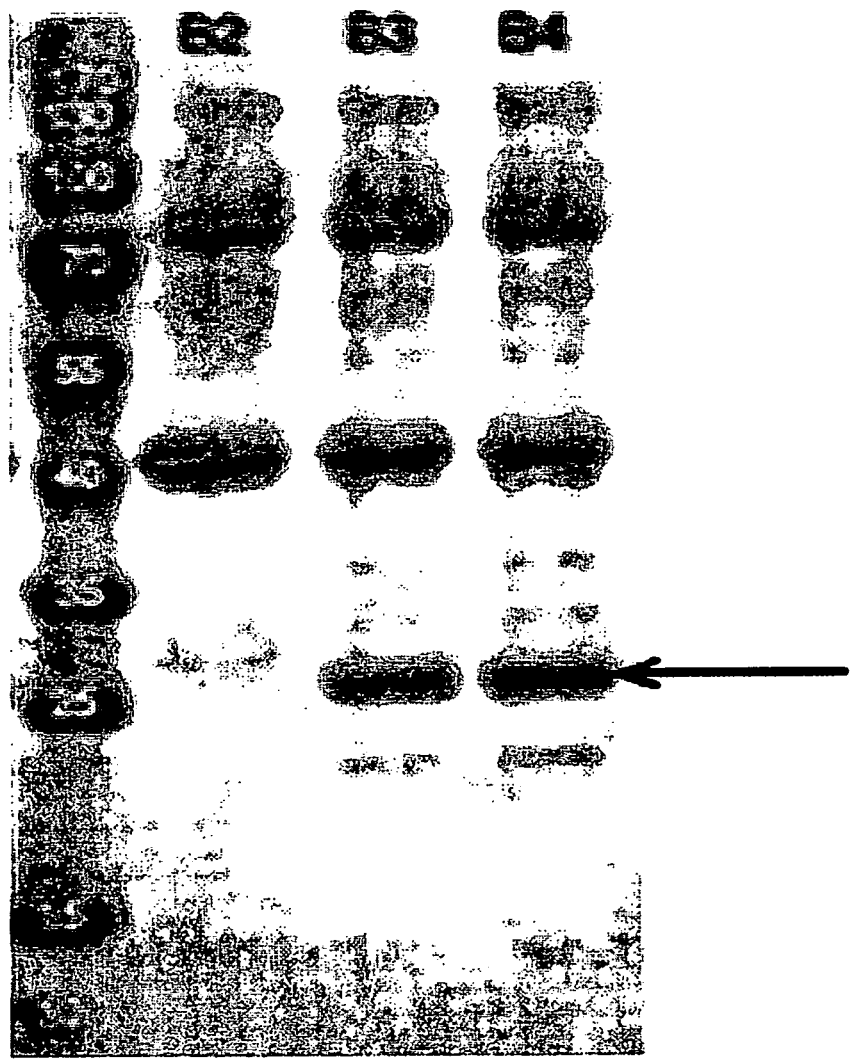

A GH61 protein-encoding gene (identifier CL10518) was overexpressed in C1 strains W1L #100.L Δalp1Δpyr5 and W1L #100.1Δalp1Δchi1Δpyr5. Culture supernatant samples were analyzed by SDS-PAGE and protein bands were stained with Coomassie brilliant blue (CBB). The CL10518 protein is .+−.26 kDa (FIG. 9). A standard fed batch fermentation was conducted, which yielded 13 g protein per liter fermentation filtrate, based on a BCA protein determination assay.

The functional analysis of this protein has been described in International patent application WO 2009/033071.

Example 14

Expression of a C1 Cellulase-Encoding Gene: Cbh2

Figure 10:
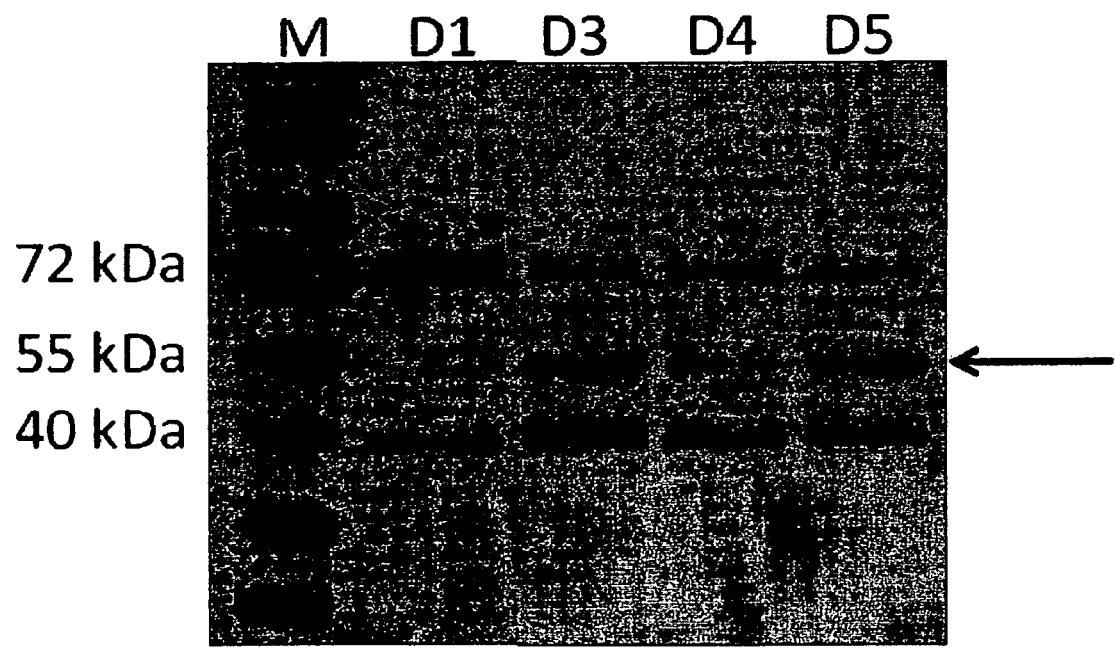

The CBH2 encoding gene (identifier CL09854) was overexpressed in C1 strain W1L #100.L Δalp1Δpyr5. Culture supernatant samples were analyzed by SDS-PAGE and protein bands were stained with coomassie brilliant blue (CBB). The CBH2 protein migrates at about 55 kDa (FIG. 10). A standard fed batch fermentation was conducted, which yielded 10 g protein per liter fermentation filtrate, based on a BCA protein determination assay.

The functional analysis of this protein has been described in International patent application WO 2009/018537.

Example 15

Expression of C1 Exo-Polygalacturonase Encoding Gene Pgx

Figure 11:
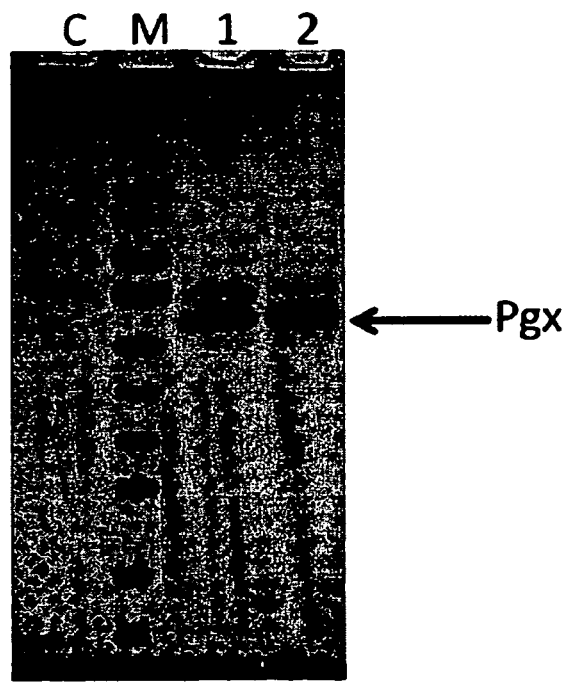

The PGX encoding gene (identifier CL10389) was overexpressed in C 1 strain W1L #100.L Δalp1Δchi1Δpyr5. Culture supernatant samples were analyzed by SDS-PAGE and protein bands were stained with coomassie brilliant blue (CBB). The PGX protein migrates at about 60 kDa (FIG. 11). A standard fed batch fermentation was conducted, which yielded 9 g protein per liter fermentation filtrate, based on a BCA protein determination assay.

The following assay was used to measure polygalacturonase activity. This assay measures the amount of reducing sugars released from polygalacturonic acid (PGA) by the action of a polygalacturonase. One unit of activity was defined as 1 μmole of reducing sugars liberated per minute under the specified reaction conditions.

Reagents

Sodium acetate buffer (0.2 M, pH 5.0) is prepared as follows. 16.4 g of anhydrous sodium acetate or 27.2 g of sodium acetate*$3H_2O$ is dissolved in distilled water so that the final volume of the solution to be 1000 mL (Solution A). In a separate flask, 12.0 g (11.44 mL) of glacial acetic acid is mixed with distilled water to make the total volume of 1000 mL (Solution B). The final 0.2 M sodium acetate buffer, pH 5.0, is prepared by mixing Solution A with Solution B until the pH of the resulting solution is equal to 5.0.

Polygalacturonic acid (PGA) was purchased from Sigma (St. Louis, USA).

Reagent A: 10 g of p-Hydroxy benzoic acid hydrazide (PAHBAH) suspended in 60 mL water. 10 mL of concentrated hydrochloric acid was added and the volume is adjusted to 200 ml. Reagent B: 24.9 g of trisodium citrate was dissolved in 500 ml of water. 2.2 g of calcium chloride was added as well as 40 g sodium hydroxide. The volume was adjusted to 2 L with water. Both reagents were stored at room temperature. Working Reagent: 10 ml of Reagent A was added to 90 ml of Reagent B. This solution was prepared freshly every day, and store on ice between uses. Using the above reagents, the assay is performed as detailed below.

Enzyme Sample

50 μL of PGA (10.0 mg/mL in 0.2 M sodium acetate buffer pH 5.0) was mixed with 30 μL 0.2 M sodium acetate buffer pH 5.0 and 20 μL of the enzyme sample and incubated at 40° C. for 75 minutes. To 25 μL of this reaction mixture, 125 μL of working solution was added. The samples were heated for 5 minutes at 99° C. After cooling down, the samples were analyzed by measuring the absorbance at 410 nm ($A_{410}$) as $A_S$ (enzyme sample).

Substrate Blank

50 μL of PGA (10.0 mg/mL in 0.2 M sodium acetate buffer pH 5.0) was mixed with 50 μL 0.2 M sodium acetate buffer pH 5.0 and incubated at 40° C. for 75 minutes. To 25 μL of this reaction mixture, 125 μL of working solution was added. The samples were heated for 5 minutes at 99° C. After cooling down, the samples were analyzed by measuring the absorbance at 410 nm ($A_{410}$) as $A_SB$ (substrate blank sample).

Calculation of Activity

Activity is calculated as follows: determine polygalacturonase activity by reference to a standard curve of galacturonic acid.

Activity (IU/ml)=$\Delta A_{410}$/SC*DF where $\Delta A_{410}$=$A_S$ (enzyme sample)—$A_SB$ (substrate blank), SC is the slope of the standard curve and DF is the enzyme dilution factor.

The $\Delta A_{410}$ of Pgx1 (CL10389) was found to be 0.78 with a DF of 1 for enzyme produced in microtiter plate cultures. No standard curve was analyzed, therefore no reliable activity can be calculated. The only conclusion to be drawn is that the enzyme was found to be active towards polygalacturonic acid, and therefore it is suggested that it is a polygalacturonase.

The functional analysis of this protein has been described in International patent application WO 2009/033071.

Example 16

Expression of a C1 Xylanase Encoding Gene with and without its Carbohydrate Binding Domain: Xyl1

Figure 12:
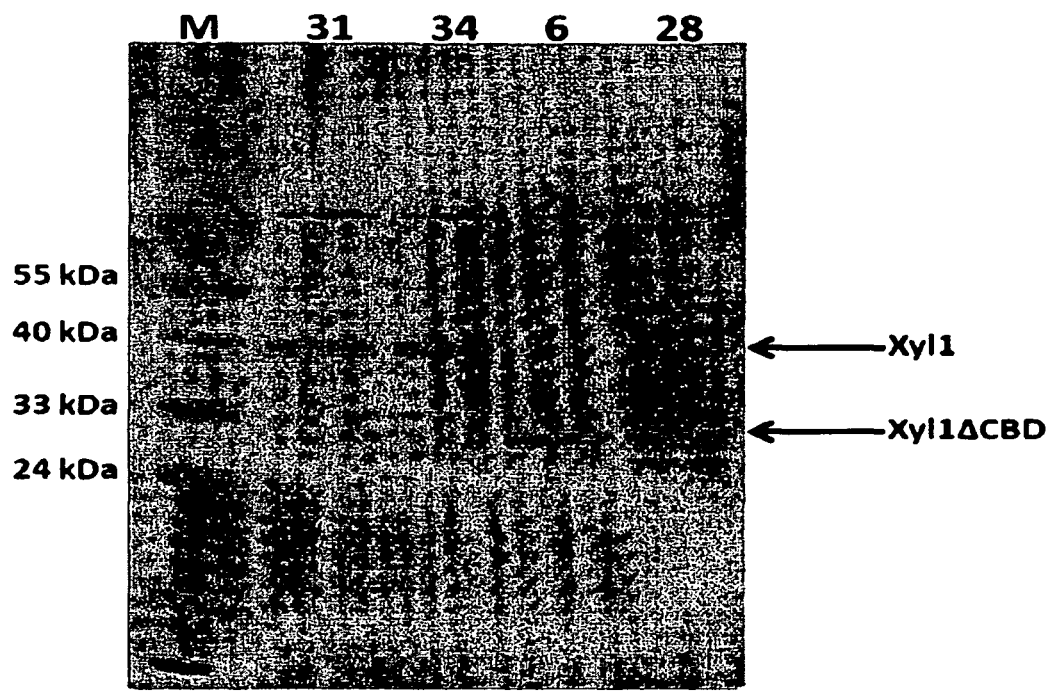

The Xyl1 encoding gene (identifier CL00649) was overexpressed in C1 strain W1L#100.L Δalp1Δchi1Δpyr5. Two Xyl1 variants were produced: either full length Xyl1 or Xyl1 without its carbohydrate binding domain (cbd). Culture supernatant samples were analyzed by SDS-PAGE and protein bands were stained with coomassie brilliant blue (CBB) (FIG. 12). The Xyl1 protein migrates at about 40 kDa, while its CBD-less counterpart migrates at about 30 kDa. Standard fed batch fermentations were conducted, which yielded up to 33 g protein per liter fermentation filtrate, based on a Bradford protein determination assay. Xylanase activities of these filtrates reached up to 3,500 U/mL.

The following assay is used to measure the xylanase activity towards AZO-wheat arabinoxylan. This substrate is insoluble in buffered solutions, but rapidly hydrates to form gel particles which are readily and rapidly hydrolysed by specific endo-xylanases releasing soluble dye-labeled fragments.

Reagents

Sodium acetate buffer (0.2 M, pH 5.0) is prepared as follows. 16.4 g of anhydrous sodium acetate or 27.2 g of sodium acetate*$3H_2O$ is dissolved in distilled water so that the final volume of the solution to be 1000 mL (Solution A). In a separate flask, 12.0 g (11.44 mL) of glacial acetic acid is mixed with distilled water to make the total volume of 1000 mL (Solution B). The final 0.2 M sodium acetate buffer, pH 5.0, is prepared by mixing Solution A with Solution B until the pH of the resulting solution is equal to 5.0.

AZO-wheat arabinoxylan (AZO-WAX) from Megazyme (Bray, Ireland, Cat. #I-AWAXP) is used as the assay substrate. 1 g of AZO-WAX is suspended in 3 mL ethanol and adjusted to 100 mL with 0.2 M sodium acetate buffer pH 5.0 using magnetic stirrer. 96% Ethanol is used to terminate the enzymatic reaction. Using the above reagents, the assay is performed as detailed below:

Enzyme Sample 0.2 mL of 10 mg/ml AZO-WAX stock solution was preheated at 40° C. for 10 minutes. This preheated stock solution was mixed with 0.2 mL of the enzyme sample (preheated at 40° C. for 10 min) and incubated at 40° C. for 10 minutes. After exactly 10 minutes of incubation, 1.0 mL of 96% ethanol was added and then the absorbance at 590 nm ($A_{590}$) was measured as $A_S$ (enzyme sample).

Substrate Blank 0.2 mL of 10 mg/ml AZO-WAX stock solution was preheated at 40° C. for 10 minutes. This preheated stock solution was mixed with 200 μl of 0.2 M sodium acetate buffer pH 5.0 (preheated at 40° C. for 10 min) and incubated at 40° C. for 10 minutes. After exactly 10 minutes of incubation, 1.0 mL of 96% ethanol is added and then the absorbance at 590 nm ($A_{590}$) is measured as $A_SB$ (substrate blank).

Calculation of Activity

Activity is calculated as follows: determine endo-xylanase activity by reference to a standard curve, produced from an endo-xylanase with known activity towards AZO-WAX.

Activity (IU/ml)=$\Delta A_{590}$/SC*DF where $\Delta A_{590}$=$A_S$ (enzyme sample)—$A_SB$ (substrate blank), SC is the slope of the standard curve and DF is the enzyme dilution factor.

The functional analysis of this protein has been described in International patent application WO 2009/018537.

Example 17

Expression of the C1 Arabinase 2 Encoding Gene Abn2

Figure 13:
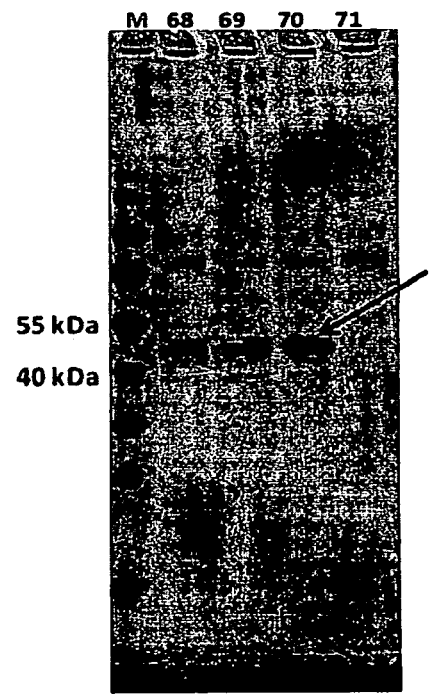

The Abn2 encoding gene (identifier CL03602) was overexpressed in C1 strain W1L #100.L Δalp1Δchi1Δpyr5. Culture supernatant samples were analyzed by SDS-PAGE and protein bands were stained with coomassie brilliant blue (CBB). The Abn2 protein migrates at about 50 kDa (FIG. 13). A standard fed batch fermentation was conducted, which yielded 7 g protein per liter fermentation filtrate, based on a BCA protein determination assay.

The functional analysis of this protein has been described in International patent application WO 2009/033071.

Example 18

Expression of the C1 Endo-Chitinase Encoding Gene Chi1

Figure 14:
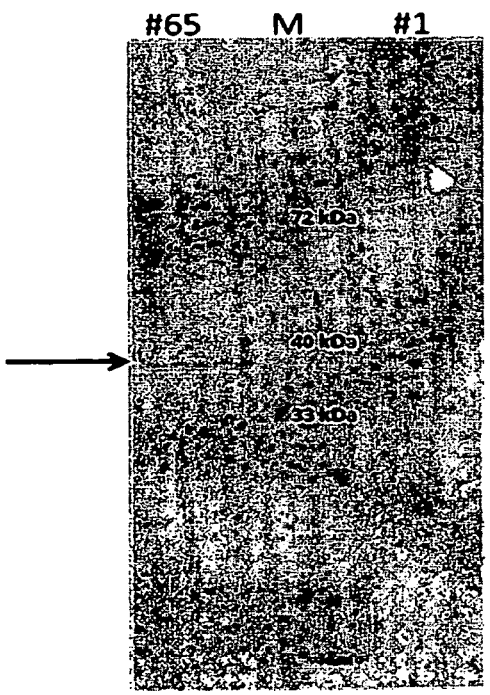

The Chi1 encoding gene (identifier CL06081) was overexpressed in C1 strain W1L #100.L Δalp1Δpyr5. Culture supernatant samples were analyzed by SDS-PAGE and protein bands were stained with coomassie brilliant blue (CBB). The Chi1 protein migrates at about 40 kDa (FIG. 14). A standard fed batch fermentation was conducted, which yielded 12 g protein per liter fermentation filtrate, based on a BCA protein determination assay.

The functional analysis of this protein has been described in International patent application WO 2009/018537.

Example 19

Expression of a Heterologous Gene: *Aspergillus Niger* Poly-Galacturonase II

Figure 15:
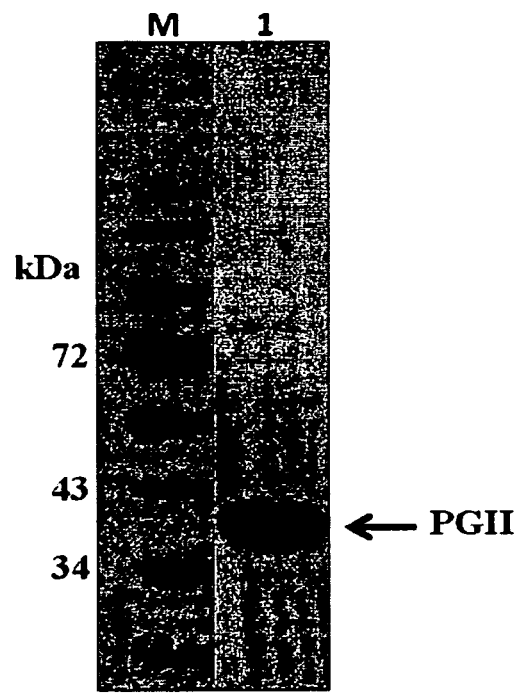

The *Aspergillus niger* poly-galacturonase II encoding-gene (accession number X58893) was expressed in C1 strain W1L #100.1Δalp1Δchi1Δpyr5. After fermentation the enzyme was purified using ion exchange chromatography and size exclusion chromatography. The purified endo-PGII migrated at about 40 kDa on SDS-PAGE gel (FIG. 15).

This heterologous enzyme was functional as was shown by activity on poly-galacturonic acid using the following assay.

Reducing Sugars Assay: PAHBAH Method
  Stock Solutions:
  Substrate: 1% (w/v) polygalacturonic acid in H$_2$O.
  Reagent A: p-Hydroxy benzoic acid hydrazide (PAHBAH) (10 grams) is added to 60 ml of water and slurried. To this is added 10 ml of concentrated HCl and the volume is made up to 200 ml. Reagent B: Dissolve trisodium citrate (24.9 g) in 500 ml of water, add calcium chloride (2.20 g) and dissolve, add sodium hydroxide (40.0 g) and dissolve. Adjust the volume to 2 liters. The solution should be clear. Store both reagents at room temperature. Working Reagent: add 10 ml of Reagent A to 90 ml of Reagent B. Prepare this solution fresh daily, and store on ice between uses.
  Assay:
  1. 50 μl substrate
  2. 30 μl 0.2M HAc/NaOH pH 5.0
  3. 20 μl sample/enzyme (microplate undiluted; fermentor>20.times. diluted)
  4. Incubate at 37° C. for 10 minutes
  5. 25 μL assay mix+125 μl Working Reagent (in PCR microplate) or 50 μL assay mix+250 μL Working reagent (in 1.5-ml tube)
  6. Heat@99° C. for 5 minutes in Thermal PCR Cycler (PCR microplate) or in boiling water (1.5-ml tube)
  7. Transfer 100 μl to NUNC microplate and measure extinction@410 nm Example 20

Generation of Artificial Enzyme Mixes for Efficient Plant Biomass Saccharification An artificial enzyme mixture was created by mixing crude protein from C1 UV18-25Δalp1 with crude protein from white strains expressing C1-β-glucosidase Bgl1, C1-arabinofuranosidase Abf3 and Abn7, C1-xylanase Xyl2 and C1-β-xylosidase Bxl1, being W1L#100.LΔalp1Δpyr5[Bgl1/pyr5], W1L#100.LΔalp1Δchi1Δpyr5[Abf3/pyr5], W1L#100.LΔalp1Δchi1Δpyr5[Abn7/pyr5], W1L#100.LΔalp1Δpyr5 [Xyl2/pyr5], and W1L#100.LΔalp1Δchi1[Bxl1/AmdS], respectively. The ratio of the different components on a protein basis was 10 (UV18-25Δalp1): 1 (white strain proteins).

The saccharification efficiency of the crude protein from UV18-25Δalp1 alone was tested on wheat bran substrate and compared to the efficiency of the artificial mixture. 10 mg protein/g dry matter wheat bran was used. Conditions were as follows: temperature 50° C., pH 5.0, time 72 hours.

It was shown that the enzyme mixture from UV18-25Δalp1 alone liberated approximately 30% of the glucose, approximately 5% of the xylose and 12% of the arabinose from the wheat bran. The artificial mixture liberated at least 60% of the glucose, 60% of the xylose and 25% of the arabinose from the wheat bran.

Example 21

Construction of Gene Libraries in White C1 Strain W1L #100.l.Δalp1Δchi1Δpyr5 and Screening of Xylanases A gene library from genomic DNA of C1 strain UV 18-25 was constructed in C1-strain W1L #100.1Δalp1Δchi1Δpyr5 by methods previously described by Verdoes et al. (2007). The library was screened for xylanase activity as described by Example 4 in chapter 4, which yielded several positive clones that expressed different xylanases. SDS-page analysis revealed the presence of extra protein bands in the positive clones. PCR analysis using different primer combinations based on the sequence of the known C1 xylanases and the vector sequence revealed the presence of 3 different C1-xylanases. This result was confirmed by Southern analysis.

APPENDIX 1 TO THE EXAMPLES: UV MUTATION PROCEDURE FOR C1 STRAINS

1. Spread parent strain onto PDA (potato dextrose agar) plates and incubate at 35° C. for 14 days to obtain spores.

2. Scrape spores into 0.9% saline and filter through cotton to remove mycelia. Dilute the resulting spore suspension to 1.times.106 spores/ml using saline. Remove a small aliquot of spore suspension, dilute in saline and spread plate to PDA to determine the initial viable spore count.

3. Add 10 ml spore suspension to a sterile glass Petri dish containing a paper clip and stir on a magnetic stir plate. Remove the glass top and irradiate with UV light to obtain 90-99.9% kill. Use a Pen-Ray lamp as the UV light source (254 nm) and warm it up for at least 10 minutes prior to irradiating the spore suspension.

4. Spread plate to ASC selective plates (Appendix 2 to the Examples) with room lights off, using a volume to obtain less than 30 colonies on each plate.

5. Invert plates, put in red plastic bags and incubate at 30° C. for 6-7 days to grow and allow clearing zones to develop.

6. Determine % kill for the mutation as the difference between the initial viable plate count and a plate count on PDA after UV irradiation.

APPENDIX 2 TO THE EXAMPLES: MEDIA

ASC Selective Agar Plates

| Component | Amount |
| --- | --- |
| Deionized water | 800 ml |
| K₂HPO₄ | 1.0 g |
| KCl | 0.1 g |
| NaCl | 0.1 g |
| MgSO₄•7H₂O | 0.3 g |
| FeCl₃•6H₂O | 0.016 g |
| (NH₄)₂SO₄ | 1.9 g |
| 20 g/l ASC | 200 ml |
| Noble Agar | 15 g |

Adjust pH to 7.5 with HCl and sterilize 30 minutes at 121° C. After sterilization add 20 ml of 25 g/l DOC (deoxycholic acid), sterile filtered. Pour about 20 ml/plate. Spread UV-mutated spores to ASC plates and incubate for 7-14 days to allow colony growth and cellulose clearing.

RM-ASP Medium

| Component | Amount |
| --- | --- |
| Bacto Peptone | 2 g |
| Bacto Yeast Extract | 1 g |
| 50x AspA (+N) | 20 mL |
| Glucose | 10 g |
| 1000x trace elements | 1 mL |
| MgSO₄•7H₂O | 0.493 g |
| Water | Bring total volume to 1 L. |

Adjust pH to 6.5 prior to autoclaving. Sterilize glucose separately as a 50% solution.

| Component | Amount |
| --- | --- |
| 50x AspA (+N) | |
| NaNO₃ (or (NH₄)₂SO₄) | 300 (or 233) g |
| KCl | 26 g |
| KH₂PO₄ | 76 g |
| KOH (10N) | 22.5 mL |
| Water | bring total volume to 1 L. |
| 1000x trace elements | |
| ZnSO₄•7H₂O | 2.2 g |
| H₃BO₄ | 1.1 g |
| MnSO₄•H₂O | 0.427 g |
| FeSO₄•7H₂O | 0.5 g |
| CoCl₂—6H₂O | 0.17 g |
| CuSO₄•5H₂O | 0.16 g |
| Na₂MoO₄•2H₂O | 0.15 g |
| EDTA | 5 g |
| Water | bring total volume to 100 mL. |

Low and High Density Cellulose Media

| Component (g/L) | Low density cellulose medium (#1) | High density cellulose medium (#2) |
| --- | --- | --- |
| BisTris | 15.7 | 15.7 |
| K₂HPO₄ | 0.22 | 0.66 |
| KH₂PO₄ | 0.08 | 0.24 |
| (NH₄)₂SO₄ | 4 | 12 |
| Na₃Citrate•H₂O | 4 | 12 |
| MgSO₄•7H₂O | 0.03 | 0.09 |
| CaCl₂ | 0.4 | 0.8 |
| Yeast Extract | 0.05 | 0.15 |
| Pharmamedia | 5 | 15 |
| Lactose•H₂O | 5 | 15 |
| Cellulose | 20 | 80 |

Adjust to pH 7.0.

chi1 sequence: see WO 2009/018537.

```
pep4 DNA sequence (SEQ ID NO: 19):
gctggctaccgttatttgctcccgcaggaagtccaggtcctcctcgcagttggacaaac    61
tctgcttcgcagcctgcaactttgactcaaggagcgcctcggcctcgtcgattgggtaag   121
acagcatgacgttggcctgccaaatgtcagcctctagaagcacactcccactctcgttgg   181
aaaggttcctaccccaagccacaagtaaacctcgtccgtcggcggtatctcggccttcgc   241
atagagagtgtcgttcaattcgaatgttgtctctatcggatcagattcgccctgccacaa   301
tcaaccgccgatcagcaccatggccgctcatcgagagtggcaacgcctcgccctaccgtc   361
ctcagcttcaaaaagcggacagcctccagcgttttccgaatgtcgggcattttgtcctt    421
agtcccgctaccctccgctgcaggttctgctccatgaactggtatttcctgcacgccgac   481
cacgtatcagccgaacgccgtccgtcaaggctggatttcaatcttaaccgggagagctca   541
cgcaatcatctcttggaaccgacgcagcgtcggctcaacatctgctcgtgacgtgacata   601
gtcctcgaccttgtcgacgaatggcgcatacggaatgccacgaggattggagggtgtggc   661
gtccctgtctcgtgcaggtggtcagtcagcaataacagccagagtgcatatgctagaatg   721
gcgcccgcggggggaggggaaagtttggttaccttgctgctgcttccttgtctgtgctcgcc   781
atcttggacaaattctcacatgttgcagtggaaggatactgcaagcgactgttaacccga   841
gccaacggagtgacgtcgggtttggtacctagtttaggtcaagccgttctcaagctgctg   901
gccaaaaattcatggcgggtcgagtgggcagcgaggtactcctcgtagggagcaaggtg    961
aagatgtgggtagcaggggtcgacgctacaaagtactttgtatccggattgctgtgtgg   1021
tacgaagcgcccgtgtgttggatgctctctgtatgtacggagtactgtacccttctccat  1081
gcgctgccccattctctatttggttgcacctgcttcgttcgtagtgtatgtacagcagta  1141
caactatctacgacacctgcactgactagtgcgtagaattctttagttttctcgagtacgg  1201
cgctaacgcttcgcgcagcaagcaccttcttctgattgtgttactgtgctcaaacctcgc  1261
cagccagctgcggtgctccacaagcccggccgtgcccaaccgccatttgcatcccggtcc  1321
catgaatctgtggacgacccatccctctctgtaccgcgtcgcggtatcagcccagaatga  1381
tagcgggaagacaaacgcagtgattcggattacgctcgcaggaaatgggggagtagctt   1441
gatagctctccacggcgagggtgtctcaggctgaggtgtcaactagttgtatgtacactc  1501
aggacgaggcattctgcgttttgaaacaccaatcttccaataccggaggtgttgatgca   1561
```

-continued chi1 sequence: see WO 2009/018537.

```
ggatcacttgaatatgtttgcacccattattactgtacctggatgattcggacagggcga  1621
gcatgattggtcgcccgttttgtcaccgcattcgcagcgtcggcgggaagcagccacgt  1681
agagcactgccaaacgtttcaagagacaccccatatggagtaaattggagtaatctgtat  1741
ccttcagagccgtcaatcaaactattgtttctcagcaggatggcccgttgctcatggggg  1801
atgtaccctggtaggtagttcgttgttgatgacttccttggatgagcctgctgcgcatga  1861
aggtgccggggcccaggttgggtgcctaaaactaactgtaaacagacgcacggtggcga  1921
cgacgtagccgaaccggtgtagcgagcttttccccggccactacgtaatcggggcgatgca  1981
ctgcaggaacacctcacacctgacctaccccttcgcctccgcatccgtcccaacccgct  2041
tccccaacctttccatcaactacttccgagactcgacatcaccttttcgcgtcgtgtctc  2101
atcgtcgttatcatcaccatcggcgatagatttgttcgcttcgatcgtcgcatcgccttg  2161
acttccattcgtccttcacgccgaccgaccggaccagacagtcgcccaaaATGAAGGATG  2221
CTTTTTTGCTGACCGCAGCTGTGCTGCTCGGCTCCGCCCAGGGAGCAGTTCACAAAATGA  2281
AGCTGCAGAAGATCCCTCTCTCTGAGCAGCTTgtacgtctgaccccgttcaagcacgcgt  2341
cagcggctactgaccttatcgcgtccagGAGGCGGTTCCCATCAACACCCAGCTCGAGCA  2401
TCTCGGCCAAAAATACATGGGGTTGCGCCCACGTGAATCTCAAGCCGATGCATCTTTAA  2461
GGGCATGGTTGCCGACGTCAAGGGCAACCATCCTATTCCCATCTCCAACTTCATGAACGC  2521
ACAGTgtatgtgacgccactgtggtggcatggatggctcgtcctcaattcggagactgac  2581
actggagcaccctagACTTCTCCGAGATCACGATTGGAACACCCCCTCAGTCATTCAAGG  2641
TGGTCCTCGATACCGGTAGCTCCAACCTGTGGGTTCCATCAGTCGAGTGCGGCTCGATTG  2701
CTTGTTACCTGCACTCGAAGTATGACTCATCTGCCTCGTCCACCTACAAGAAGAACGGAA  2761
CCTCGTTCGAGATCCGCTACGGGTCAGGCAGCCTGAGCGGGTTTGTCTCTCAGGACACAG  2821
TGTCCATCGGCGATATCACTATCCAGGGCAGGACTTTGCCGAGGCGACCAGCGAGCCCG  2881
GTCTTGCCTTTGCCTTTGGCCGTTTCGACGGTATCCTTGGCCTTGGCTACGACCGGATCT  2941
CAGTCAACGGCATCGTCCCGCCTTTTTACAAGATGGTCGAGCAGAAGCTCATCGATGAGC  3001
CCGTCTTCGCCTTCTACCTGGCCGATACCAATGGCCAGTCTGAGGTTGTCTTTGGCGGTG  3061
TTGACCACGACAAGTACAAGGGCAAGATCACCACCATTCCGTTGAGGCGCAAGGCCTACT  3121
GGGAGGTTGACTTCGATGCCATTTCTTACGGCGACGACACTGCCGAGCTTGAGAACACTG  3181
GCATCATCCTGGACACCGGTACTTCTCTGATCGCTCTGCCCAGCCAGCTCGCCGAGATGC  3241
TCAACGCTCAGATCGGCGCTAAGAAGAGCTACACTGGCCAGTACACCATCGACTGCAACA  3301
AGCGCGACTCCCTCAAGGATGTCACGTTCAACCTGGCTGGCTACAATTTCACGCTCGGCC  3361
CCTACGACTACGTTCTCGAGGTCCAGGGCAGCTGCATTTCTACCTTTATGGGCATGGATT  3421
TCCCGGCTCCTACTGGGCACTTGCGATCCTGGGCGATGCTTTCCTCCGGAGGTATTACT  3481
CCATTTATGACCTTGGCGCCGACACCGTCGGTCTGGCTGAGGCCAAGtgattgaaggatg  3541
ggcggcagggaaagacgatgggtaatacggggagtctgggaatcgggctttggactgtgg  3601
tctgtatctagttgctcaagagagttgtcgtttgattttgttataggatctgtctaggaa  3661
ccttagcaggagtgaaattttttcgtgtacgagcatcggcgggctgaagtggtttgataa  3721
caagtcctggacttgagtacgcaggcagttgcacaatctgcttcgccgaggagagcaaagg  3781
cgtcctcttttgaaaaagcctacctacgcgtcacaggggtataatttttttgagtttgacct  3841
acgccctgtcccataccaaccgcgtcccaatcccgtcaaccttgcaatgtcattccc  3901
gtggatgtatcacgtagcagaagccgacatcccacacgcttcaaccttcctatccagaca  3961
atgacatggtaagctcattttttaaaggtcgccgtcctccctccctttcacgtgattcatt  4021
ttccttgcgccttgtggcgcatcccctgacttcatgccgtacggatcaaagggtgcaaac  4081
ttgccccgcacctcttttctgccgccatcatcatcaccatcatcgccgtttgtcgcctgc  4141
gcagcatgtagcacggacgacgccttgctgtagtcaaacggctcctgctcggcatcgtca  4201
tcatggccttcctcctgttcgcccgaggtctgttcgtcggctgccgaggtcgcggcggga  4261
gcagatgtctgctgctgctgctgctgctgcttctgggctttcttggcggctcgaagt  4321
gccttcctggcttgagccttgagttccttttgctccctttatgtctccgttttgagccagt  4381
tgctctgccaagagctgagcacgcttgaactcttctcgagcagccttcttggcttgtttc  4441
tttgcctgcttggcggccttgtcatcaccaccctcaacttcctgctcgacactaggagac  4501
ttcgggtggtctttgcctgcggaactatctccacccatctcgatgtcggaaactgcttcg  4561
gcttcggatgctgactcaacatcaacatccctagacttccgctttcgaccagccttcaga  4621
gtgaaaccttcttcttcgagaacagggagaccttggtgtcttgttcagcgacacgcctg
```

Pep4 amino acid sequence (SEQ ID NO: 20):

```
MKDAFLLTAA VLLGSAQGAV HKMKLQKIPL SEQLEAVPIN TQLEHLGQKY MGLRPRESQA   61
DAIFKGMVAD VKGNHPIPIS NFMNAQYFSE ITIGTPPQSF KVVLDTGSSN LWVPSVECGS  121
IACYLHSKYD SSASSTYKKN GTSFEIRYGS GSLSGFVSQD TVSIGDITIQ GQDFAEATSE  181
PGLAFAFGRF DGILGLGYDR ISVNGIVPPF YKMVEQKLID EPVFAFYLAD TNGQSEVVFG  241
GVDHDKYKGK MTTIPLRRKA YWEVDFDAIS YGDDTAELEN TGIILDTGTS LIALPSQLAE  301
MLNAQIGAKK SYTGQYTIDC NKRDSLKDVT FNLAGYNFTL GPYDYVLEVQ GSCISTFMGM  361
DFPAPTGPLA ILGDAFLRRY YSIYDLGADT VGLAEAK
``` his2a DNA sequence (SEQ ID NO: 21):

```
cattcatggg tttgaggccc gatttgaac gtatatccta ggctatattc ggggtaagat    61
actggaagcg ctgggccgga tgactagcta tttcaagtgc ccaagagccc atcataccta   121
acttgtggcc taagatctag ccaaatcatt cattggttac cccagactcg acgaacctga   181
tattcgaatc cagggcaagt caaatcgccg agtaagactt gacaaacccg gaacccaaga   241
actgcgcaat ctgggagcag gtttccgacc agcatggaaa caccccgatg gaaacccac   301
acatacgggg atgggggacta acgccggaca aatcaaaaac cctggaggat tgggtaacga   361
tggggaagtc cgacgggcac tcaacccttc aagcgttgca ggaccttgta cagccaagca   421
gaatgacgga aaccgatgag caaacccgga atctgatgat cctggaacag aatcatctgt   481
cttgggtacc gacgttggag tgagagtgtg caaattagca ggataaagca actatactac   541
ctaaatcagg tcgatcagtt atcagcccctt gcaaaccaga cttgatggag ggaagagggtg   601
aaagctgtga ttgagggagg aagctgagaa ttggtggtgg ttgttttgct cagccagggt   661
gtaggacgag aagaacgcgt tcgagatttc ggagagcagg ctgtcctaga gcattatttt   721
cctggccttg agcaaactta agccagtttt ttttttcccg tcgggaggga agtcgctttg   781
aatttgaagc ttgcgggcgc agagctcggc tccataagca tccaatcaaa tgagcctgaa   841
```

| chi1 sequence: see WO 2009/018537. |
|---|

```
gcagtcgacc gatttttttt tatctgggtg taatcgcaac catgcacata accgttttgg  901
gactagctcc aacagctccg atcaacaacc tgagaaaggc gcgagtgatc cgtgatccca  961
caccccttacg cgaaaactac ttaactccca cctcccccac cgcgggtcaa cttcttccaa 1021
ctcccactca accaacttcc gttttcccat caatcactgc attcgcgcgt caagctcttc 1081
ctcgcccttca caccaaccac ataacttttt tatcctttga caaggaccat caatcaaaAT 1141
GACTGGCGGC GGCAAGTCCG GTGGCAAGGC GAGCGGTTCC AAGAACGCGC AATCgtaggt 1201
gccctttttcg cgtcatctac ccgcgccttc gtgcagttgg gcatggttca gccttgaacct 1261
ccagatgccc gttccggtgc tcttacagtt ggctaacttt ttgtagTCGT TCATCTAAGG 1321
CCGGTCTTGC GTTCCCTGTC GGTCGTGTCC ACCGCCTTCT CCGGAAGGGC AACTACGCCC 1381
AGCGTGTCGG TGCCGGTGCT CCCGTTTACC TGGCTGCCGT TCTCGAGTAT CTTGCCGCTG 1441
AAATTCTGGA GCTGGCTGGC AACGCCGCTC GCGACAACAA GAAGACGCGT ATCATCCCGC 1501
GTCACTTGCA ACTCGCTATC AGGAACGATG AGGAGTTGAA CAAGCTTCTC GGGCACGTCA 1561
CCATCGCCCA GGGTGGTGTC CTTCCCAACA TCCACCAGAg tacgttgcct taccagacga 1621
tctctaatgc gcaaatctaa ctttgtttcc agACCTTCTG CCGAAGAAGA CCGGCAAGAC 1681
CGGCAAGAAC TTGTCGCAGG AGCTCtgatt ttcgcggttg ggttttttg ctttattttc 1741
tggtcggcac gctgggttca tgatatcggg tcacggttt cgggtcattg gttgcttttt 1801
gcgcgtgttt gggctgtaca ttaattccat gatgggcatg gtcatggtta tgaatgagaa 1861
tatcctctga acatccaaat cctgacacag tttgctcgag ttgatgtctg cattggaagc 1921
gactcgttga cggtaccgcg tagagtcttg tcgcttacga aattcttgca tcgcacagat 1981
tacccagtag tgccatagta ctctttaaga tgataagtgc atttgagccc ggcatcgcac 2041
agactttccc atgccttgat atatgcgaat tcctatgtac aagagattcg tcgcgaaaga 2101
gcccgtcaaa acttgagcgg ggggggagct gcaaaagcct gtcagctaat tcgagtgaga 2161
cgcgcaaagc aagccaactt acgatccagg tggggcgccg ggaggtttct ctcgtatttc
```

His2A amino acid sequence (SEQ ID NO: 22):

```
MTGGGKSGGK ASGSKNAQSR SSKAGLAFPV GRVHRLLRKG NYAQRVGAGA PVYLAAVLEY  61
LAAEILELAG NAARDNKKTR IIPRHLQLAI RNDEELNKLL GHVTIAQGGV LPNIHQNLLP 121
KKTGKTGKNL SQEL
``` hex1 DNA sequence (SEQ ID NO: 23):

```
gtcaacttactccgagtctcgcatcgagttcgatactgagcaccgtactcacaactccgt     61
cattgacgttgctgagggcgagtatcgtgcccgtgtccagcccaaccaccgcaagcaagc    121
ttccgtagtcggtaccaccgtcaacggatcgcggttcagccacagccgcaaggccagcag    181
caccacctccacccacaccgacgagtacaccgtcgatcccccctagccaccgcccgtcta    241
caagaaggagtcggttgaagtcgccggtaccactgttgaccccctgctcctcgttcgac    301
ctaccacgagcaggtgaacattgttgaagagaccgttgacgctcaccgttacgctcctca    361
acccaacaacaacaacaagATGGGCTACTACGACGAGGACGgtaagcatcttccttccc    421
tttgatgttgttccttaccgtgacatccatcggtcgtatgctttcttagccacacacaa    481
gtgttgtgacaagtgccgtgctcacgccgatatcagGCCACTACCACTCTTTCCGCCATG    541
GATTGCACAAGTTGGCTGACCGTATTGCGCATCCTGAAGGCCATGACCGCGTTGAGGTGA    601
GCGAGGTTCGTGAGACCCGCCGCACCCGCGCTCCGTCTTCGGAGGCGTACACGCCGAACA    661
CGGTCACCATTCCGTGCCACCACATCCGCCTCGGCGACATCCTGATCCTCCAGGGCCGCC    721
CCTGCCAGGTCATCCGTATCTCGACCTCGGCTGCCACTGGCCAGCACCGCTATCTTGGTG    781
TCGACCTCTTCACCAAGCAGCTCCATGAGGAGTCGTCGTTCGTCTCGAACCCTGCTCCCA    841
GCGTCGTCGTCCAGACGATGCTTGGCCCTGTTTTCAAGCAGTACCGCGTCCTCGACATGC    901
AGGACGGCCACATCGTCGCCATGACCGAGACGGGCGATGTCAAGCAGAACCTGCCCGTCA    961
TCGACCAGAGCAACCTCTGGGGCCGCCTCAAGCAGGCCTTCGAGACTGGCCGCGGCAGCG   1021
TCCGTGTCCTGGTCGTTTCTGACAACGGCAACGAGATGGCTGTTGACATGAAGGTCGTCC   1081
ACGGCTCGCGCCTCTAAgtcaagccggcaggctttcatgcaagctttggggctacgagtc   1141
gggcggcattgggttgttcgtttgatgcatcttggttacggcgtatgtcatttgaagat   1201
tgaaagctgcgccttggtcgactcctggcgccggatggatatacatgttcctcgggagga   1261
tatgaaggtttcatgtcgctagtttcacgtgtatatgatgactgtaatggatggatgttt   1321
atggccaactttgcgattgatatcttgaacctttttctggtcgtgtgagtgaacagtga   1381
ttaagtgagagtgaggtatgcaccgttatcacaaggttgccttgatatcccaccttcaa   1441
cgggcgtggggaatcgaagtccctcccctacagtaagtagcctctcttgaatgatctgaa   1501
acgcaacccctccgagccactaccacacctaactacgaaacaaccactttcctgttccag   1561
gaagctccagttctcccgctacctcccctcccgccgttcaggttgtacgcttatctccc   1621
aacctcatcttcgagaggtctaatccgtacacacttaacagtgcatcctgacatagctaa   1681
ccatcatcactctagttcattagccgtcccgccatcccgtcaattacattcccggctgtt
```

Hex1 amino acid sequence (SEQ ID NO: 24):
```
MGYYDEDGHY HSFRHGLHKL ADRIAHPEGH DRVEVSEVRE TRRTRAPSSE AYTPNTVTIP  61
CHHIRLGDIL ILQGRPCQVI RISTSAATGQ HRYLGVDLFT KQLHEESSFV SNPAPSVVVQ 121
TMLGPVFKQY RVLDMQDGHI VAMTETGDVK QNLPVIDQSN LWGRLKQAFE TGRGSVRVLV 181
VSDNGNEMAV DMKVVHGSRL
``` bgl1: see WO 2009/018537. Note that bgl1=Bgl3A.
xyl6: see WO 2009/018537.
cbh1: see WO 2009/018537. Note that cbh1=CBHIa.

```
Pchi1 (0.8) (SEQ I No 25):
AGCTTGACCCTTTCAGAGCTAGGTTTCATTAGGCCTTCGAAAACAACCCAAGGCCCCGTC

GCAACCATCACAACCGGCCGATAACCAGATCTCGGTAGGTCCGATAAGGATCCAAAATGG

TGTCGGCTGACGTTGCATGTGCCCAGGCAGGAGGATGATCCCCAGGGTTGTTGCCGGCAG

CTCCCGCACGTCGGGGAGGGGGAGGGGGAGGGGAAAGCCCTAACTAACGTTCGTTCTATC

ACGGGCCGACCGGGCCATGCTTTCGGCTTGTGAGCGGTGGGGTCAAGGGCAACAAGAAAT

GCTAAGTGCGGGACGAAGACACGCGGGCATGAGGTCTCAGGGTGACCTGCGCAAAACCAA

GTCCCACTCGCCATGCCTCCAGCAGCAACGTTGCCGTAGAAGGGTCAGGGGGTTTGTTGT

AGACCCACGACCATGCTGCCGGCGAGCGGAGGGTTGGCTTGCTACAGGCGCTGAAGGGTC

AACTCGGTGCCCAAAGTGGCTACCAAGCGTGCCATCAAGGGAAATGAGATGATGGTGGCT

CGTGGGCAAAGAAAAGACAAGGGAGGTGACTCTAGAGAGATGCTCTCGAGTTCACGGGTA

TAAGAGCACTGTGATCGTTCACAAAGCCGGCGTACTCCTCTAGAGCATCTATCATCAACA

TCACCAGAAAGGTCNTAGACCAGGTGGTTGCCATATCCAGTCGCAAAAGAGCCAAAGAGC

GAAGGAGCACGAAAGCACAGCCCAATCATTCCCTGCTTTGCTACTTCTTCTCCACC

Pchi1 (1.8) (SEQ ID NO: 26):
GTCCCTTACCTATGGGCTCCTAGTCTCGTTCCTCTTTTTGATAGATTTGTATTTTGCAAC

GTTGCAAAATGAGACATTTCAATCATATGTAGCCGCCAGCTACTGTTAGCGTACTCAGCG

TTGCCCAAACGGCGGTTTTTCTGGGTAGCACTGTGCCGCGTGCCCCTGAGCCGTGCGTCG

CGGAAACCCCCTTAAGTAGCAAGTATGTTACCGCCGAGACCGACAATGCTGTTGGTTACC

TCGCTGGTCCATGATTGCAATCTAGATATCGTGCGGGCTTTTGCAATCGGTTTTCCCTA

CCCACTTTCTTCTTTTGGACACTTTCTCTTTTGGAAAATGCCGAAATGATGCGGCTCGCT

CACGCCCCGAAGTCCCGAGCTGGGGCTAGATCCGTGATTGCAACGCGGTGCGAACGCGAC

TGGGGCAGACCTCGCTCAGCCTTGGTCGTGCCGGAATGGCGGGTACCTTTACCAGGTCGG

GATCAATTACATAGGATGCCATGTGCGTGGATTTGATTGCATCGCTGTCCCTTTTGTATG

TGTCCGAGAGCGAGACATCAACGCGAAAACCGGAATGCTCCCAACGTCGCTCTCTGTTCA

TAGGGTCTTTTTTTTCTTCTGCTCCATATCATCTGTCTTGAACTAAGTGATCATCTGCT

GTCACGTCCCGCCCAATGATTGTAAAGAATGATAAGTGATGCTCGCCGGGGCCAGGCTCT

GTGAAAGTTCCCTCTTTGGTTGACGATCAGGTAGCGCCAACGTTGATTGGGCCGCCCGTA

AAATCCGACCCTGTCTCCTTTCGTTGCAAGTCTCCGCGAGACCGTGCCAAGCATGTTCTC

CGGATCCCTCAATTACATAAGGTTTGGCTCCAGGGTAGGTCTGGAAGCTACCCACCTCGG

CCAAGCAACCAATCACAACCAGACCTCGCGGCGTTTCGACCTTCCTGGTTTGTCTCAGGG

CTGGCCAACGTCCTCCCGTGGCGGGTGCCTGGTGATCGCAGGTCGCAGGCGAGTGCCGGG

CACGCGGAGCCCCCGTCAAAGCTTGACCCTTTCAGAGCTAGGTTTCATTAGGCCTTCGAA

AACAACCCAAGGCCCCGTCGCAACCATCACAACCGGCCGATAACCAGATCTCGGTAGGTC

CGATAAGGATCCAAAATGGTGTCGGCTGACGTTGCATGTGCCCAGGCAGGAGGATGATCC

CCAGGGTTGTTGCCGGCAGCTCCCGCACGTCGGGGAGGGGGAGGGGGAGGGGAAAGCCCT

AACTAACGTTCGTTCTATCACGGGCCGACCGGGCCATGCTTTCGGCTTGTGAGCGGTGGG

GTCAAGGGCAACAAGAAATGCTAAGTGCGGGACGAAGACACGCGGGCATGAGGTCTCAGG

GTGACCTGCGCAAAACCAAGTCCCACTCGCCATGCCTCCAGCAGCAACGTTGCCGTAGAA
```

-continued

GGGTCAGGGGGTTTGTTGTAGACCCACGACCATGCTGCCGGCGAGCGGAGGGTTGGCTTG

CTACAGGCGCTGAAGGGTCAACTCGGTGCCCAAAGTGGCTACCAAGCGTGCCATCAAGGG

AAATGAGATGATGGTGGCTCGTGGGCAAAGAAAAGACAAGGGAGGTGACTCTAGAGAGAT

GCTCTCGAGTTCACGGGTATAAGAGCACTGTGATCGTTCACAAAGCCGGCGTACTCCTCT

AGAGCATCTATCATCAACATCACCAGAAAGGTCNTAGACCAGGTGGTTGCCATATCCAGT

CGCAAAAGAGCCAAAGAGCGAAGGAGCACGAAAGCACAGCCCAATCATTCCCTGCTTTGC

TACTTCTTCTCCACC

Phex1 (SEQ ID NO: 27):
GATCCTAAGTAAGTAAACGAACCTCTCTGAAGGAGGTTCTGAGACACGCGCGATTCTTCT

GTATATAGTTTTATTTTTCACTCTGGAGTGCTTCGCTCCACCAGTACATAAACCTTTTTT

TTCACGTAACAAAATGGCTTCTTTTCAGACCATGTGAACCATCTTGATGCCTTGACCTCT

TCAGTTCTCACTTTAACGTANTTCGCGTTAGTCTGTATGTCCCAGTTGCATGTAGTTGAG

ATAAATACCCCTGGAAGTGGGTCTGGGCCTTTGTGGGACGGAGCCCTCTTTCTGTGGTCT

GGAGAGCCCGCTCTCTACCGCCTACCTTCTTACCACAGTACACTACTCACACATTGCTGA

ACTGACCCATCATACCGTACTTTATCCTGTTAATTCGTGGTGCTGTCGACTATTCTATTT

GCTCAAATGGAGAGCACATTCATCGGCGCAGGGATACACGGTTTATGGACCCCAAGAGTG

TAAGGACTATTATTAGTAATATTATATGCCTCTAGGCGCCTTAACTTCAACAGGCGAGCA

CTACTAATCAACTTTTGGTAGACCCAATTACAAACGACCATACGTGCCGGAAATTTTGGG

ATTCCGTCCGCTCTCCCCAACCAAGCTAGAAGAGGCAACGAACAGCCAATCCCGGTGCTA

ATTAAATTATATGGTTCATTTTTTTAAAAAAATTTTTTCTTCCCATTTTCCTCTCGCTT

TTCTTTTTCGCATCGTAGTTGATCAAAGTCCAAGTCAAGCGAGCTATTTGTGCTATAGCT

CGGTGGCTATAATCAGTACAGCTTAGAGAGGCTGTAAAGGTATGATACCACAGCAGTATT

CGCGCTATAAGCGGCACTCCTAGACTAATTGTTACGGTCTACAGAAGTAGGTAATAAAAG

CGTTAATTGTTCTAAATACTAGAGGCACTTAGAGAAGCTATCTAAATATATATTGACCCT

AGCTTATTATCCCTATTAGTAAGTTAGTTAGCTCTAACCTATAGATAGATGCATGCGGCC

GCAGGTACCAGGCAATTCGCCCTATAGTGAGTCGTATTACGCGCGCTCACTGGCCGTCGT

TTTACAACGTCGTGACTGGGAAAACCCTGGCGTTACCCAACTTAATCGCCTTGCAGCACA

TCCCCCTTTCGCCAGCTGGCGTAATAGCGAAGAGGCCCGCACCGATCGCCCTTCCCAACA

GTTGCGCAGCCTGAATGGCGAATGGGACGCGCCCTGTAGCGGCGCATTAAGCGCGGCGGG

TGTGGTGGTTACGCGCAGCGTGACCGCTACACTTGCCAGCGCCCTAGCGCCCGCTCCTTT

CGCTTTCTTCCCTTCCTTTCTCGCCACGTTCGCCGGCTTTCCCCGTCAAGCTCTAAATCG

GGGGCTCCCTTTAGGGTTCCGATTTAGTGCTTTACGGCACCTCGACCCCAAAAAACTTGA

TTAGGGTGATGGTTCACGTAGTGGGCCATCGCCCTGATAGACGGTTTTTCGCCCTTTGAC

GTTGGAGTCCACGTTCTTTAATAGTGGACTCTTGTTCCAAACTGGAACAACACTCAACCC

TATCTCGGTCTATTCTTTTGATTTATAAGGGATTTTGCCGATTTCGGCCTATTGGTTAAA

AAATGAGCTGATTTAACAAAAATTTAACGCGAATTTTAACAAAATATTAACGCTTACAAT

TTAGGTGGCACTTTTCGGGGAAATGTGCGCGGAACCCCTATTTGTTTATTTTTCTAAATA

CATTCAAATATGTATCCGCTCATGAGACAATAACCCTGATAAATGCTTCAATAATATTGA

AAAAGGAAGAGTATGAGTATTCAACATTTCCGTGTCGCCCTTATTCCCTTTTTTGCGGCA

TTTTGCCTTCCTGTTTTTGCTCACCCAGAAACGCTGGTGAAAGTAAAAGATGCTGAAGAT

CAGTTGGGTGCACGAGTGGGTTACATCGAACTGGATCTCAACAGCGGTAAGATCCTTGAG

```
AGTTTTCGCCCCGAAGAACGTTTTCCAATGATGAGCACTTTTAAAGTTCTGCTATGTGGC

GCGGTATTATCCCGTATTGACGCCGGGCAAGAGCAACTCGGTCGCCGCATACACTATTCT

CAGAATGACTTGGTTGAGTACTCACCAGTCACAGAAAAGCATCTTACGGATGGCATGACA

GTAAGAGAATTATGCAGTGCTGCCATAACCATGAGTGATAACACTGCGGCCAACTTACTT

CTGACAACGATCGGAGGACCGAAGGAGCTAACCGCTTTTTTGCACAACATGGGGGATCAT

GTAACTCGCCTTGATCGTTGGGAACCGGAGCTGAATGAAGCCATACCAAACGACGAGCGT

GACACCACGATGCCTGTAGCAATGGCAACAACGTTGCGCAAACTATTAACTGGCGAACTA

CTTACTCTAGCTTCCCGGCAACAATTAATAGACTGGATGGAGGCGGATAAAGTTGCAGGA

CCACTTCTGCGCTCGGCCCTTCCGGCTGGCTGGTTTATTGCTGATAAATCTGGAGCCGGT

GAGCGTGGGTCTCGCGGTATCATTGCAGCACTGGGGCCAGATGGTAAGCCCTCCCGTATC

GTAGTTATCTACACGACGGGGAGTCAGGCAACTATGGATGAACGAAATAGACAGATCGCT

GAGATAGGTGCCTCACTGATTAAGCATTGGTAACTGTCAGACCAAGTTTACTCATATATA

CTTTAGATTGATTTAAAACTTCATTTTTAATTTAAAAGGATCTAGGTGAAGATCCTTTTT

GATAATCTCATGACCAAAATCCCTTAACGTGAGTTTTCGTTCCACTGAGCGTCAGACCCC

GTAGAAAAGATCAAAGGATCTTCTTGAGATCCTTTTTTTCTGCGCGTAATCTGCTGCTTG

CAAACAAAAAAACCACCGCTACCAGCGGTGGTTTGTTTGCCGGATCAAGAGCTACCAACT

CTTTTTCCGAAGGTAACTGGCTTCAGCAGAGCGCAGATACCAAATACTGTCCTTCTAGTG

TAGCCGTAGTTAGGCCACCACTTCAAGAACTCTGTAGCACCGCCTACATACCTCGCTCTG

CTAATCCTGTTACCAGTGGCTGCTGCCAGTGGCGATAAGTCGTGTCTTACCGGGTTGGAC

TCAAGACGATAGTTACCGGATAAGGCGCAGCGGTCGGGCTGAACGGGGGGTTCGTGCACA

CAGCCCAGCTTGGAGCGAACGACCTACACCGAACTGAGATACCTACAGCGTGAGCTATGA

GAAAGCGCCACGCTTCCCGAAGGGAGAAAGGCGGACAGGTATCCGGTAAGCGGCAGGGTC

GGAACAGGAGAGCGCACGAGGGAGCTTCCAGGGGGAAACGCCTGGTATCTTTATAGTCCT

GTCGGGTTTCGCCACCTCTGACTTGAGCGTCGATTTTTGTGATGCTCGTCAGGGGGGCGG

AGCCTATGGAAAAACGCCAGCAACGCGGCCTTTTTACGGTTCCTGGCCTTTTGCTGGCCT

TTTGCTCACATGTTCTTTCCTGCGTTATCCCCTGATTCTGTGGATAACCGTATTACCGCC

TTTGAGTGAGCTGATACCGCTCGCCGCAGCCGAACGACCGAGCGCAGCGAGTCAGTGAGC

GAGGAAGCGGAAGAGCGCCCAATACGCAAACCGCCTCTCCCCGCGCGTTGGCCGATTCAT

TAATGCAGCTGGCACGACAGGTTTCCCGACTGGAAAGCGGGCAGTGAGCGCAACGCAATT

AATGTGAGTTAGCTCACTCATTAGGCACCCCAGGCTTTACACTTTATGCTTCCGGCTCGT

ATGTTGTGTGGAATTGTGAGCGGATAACAATTTCACACAGGAAACAGCTATGACCATGAT

TACGCCAAGCGCGCAATTAACCCTCACTAAAGGGAACAAAAGCTGGAGCTCCACCGCGGT

GGCGGCCGCTCTAGAACTAGTACGGCGTGCAAGTAGTGTCTTTCTTTGCACTCCCGCCGT

CCCAGAAGACGCCGCAACAAGCTGAGCTTGCTGGAAGCCGAACAAAGGCGTTACAGAGCA

CAAACATAGTGGCAGTGTAGGAACTCTAACTGGGACCAAAACTACGGGCCCGGCAGAAAC

GTTCCCCGCCCCGAAGCGAAGGCGAACGTCGAAAAGCAAGACCGGGACCGCTCGTCCCAG

GATTAGCCACGAAGTTCCAGACCAAGTATAGGAGTAAACGCTCGCTCGTCAAAACAATTG

TCACCAATCAGCACCACATCGGCACATAACAACCGGTTGCGGAACTCGCATGTGAACAAC

AAGCGGCTCCGGGGAGTGATCGGCTCGGCGGATGACCCGGACTCTTCCGCGCAGCAAC

TCGGCGTGTTGTTGACGGCAGTACTCCGTAGTTGCCATGACAACAGTCAATGGCGTGCTT
```

-continued

```
CACAAGGTGGAGAGCCGAGAAAGCACCTCGGCATGTACGAGTATGTAGATAGTGTATCAA

GCAGGAAGATGGGGGTTACTTTATCTCAATCAGATGCCTGTAAGCGAGAGCCGAGAGCCT

GCCCTGTTGTTGACACAATTCTGGCCTGATACGAGTGACAAGCGCTGGGACGGCGGCTGG

GGTCTTTTGCTCGCGGCTTCAGCTCAATTCCAATCCTGGGCCGGTGCCGAACGGCCCAAT

CGCGAGCGCCCACGAAATCGGAGGTCGAGGAAAGAAGGCTGGGCGAGACGCGGCGACAAG

CTGTGGCAAAATGGCCAATTGAGGTTCTGGGTCGGCTGGTGATCAACCATGCATTTCCCA

GCCCGCAGATTCTCTTTCTCTCGTGCAGCAGCGGCACCAGCAGCAGCAGCAGCCAGGG

GTTTGACCAACCTCTCCGCCCAGCCACCGATAGTAAAGATGCTGCCTGCGTATTCTGGGC

TGCAGGAGTTCCAAGATCTTTCGGTCTGGCCACCAGCTGTCACGTCACCCTCCACCTTTG

GACGACGTTGCTGGAAAATTCGAAGCCTTCACTAAGATAACTATGCCGTAGCACTTGCAG

CCCCGGAAGCTGCAAGTTGATTCTTGGAGGGCTCTCTCCACCACCAATACGGGAGATCTG

GCCCCGCACTTGAGGAGGCTGGAGTCTCGGATCGCCCACTTCGCGTCGCCCTGGGCCCTG

GGCCCTGGGGTGATGGGCCCGTTGCCGTGGTGGATGGCAGGAGCTTTTCAGCTCTCAATG

GGCGAATGCTACTCCGTAGGTCGGAGTGGCTGGAAGCGGCGGAACGGACAGGGGGAGGTT

GGGGAAAATGCTCCGCAGGAAGAGCAGGGAGTGGGGAGCTGCGGTCGGCCCTGTGGAGCC

CGTGCAGGGCCAGCTAATCCAATTCGGGCCACAATAAACAAGAGAGGGCCCCACATCATG

TAAACAGAGGCTCAGAAGCTCCTGCCACACTGGGAGGGTTTCGAAGTCTGACGACTGCCA

ATGGACCCCAGCCATCGCGAGCACACAGCAGTTCGCACGCTCCCATTGGGTTCCTCATCA

CGCAGTCGCTCTCCCCGCCAACCAGCGCCAGGTCCGGGAACAGCGGCGCAAATGCGTATT

TGAGGGCGCCTCGCTCGAGCAACCTGTGCCTGACCTTCTCCTCCTCCTTCTGCACCTTGC

ATCTCGTCGCGTCCACTCGCAGGCAACCACACATCCTCCTCCTCTCCCAAAACCCCCCCG

CTTTTTCTTTCCCTTGTTGGAATTCGATTGAAAAGAAGACGGGTCCGTCTAGAGACCGC

CTTCTCACCTTTCTCTCGACTTCTTTCTAGGAAAAGAAGCAAGAGTCATTCTTCTTGTCC

ACCTTCTGGTTCACGGAAGGTCGAGGAGAAGATTGCCTCTGCCCCCAAAGTCGCCAACCT

GGACTTTGAAGCACGTGTTCCGGTCCCTTTCAGTGTCTTCCCGTCCTCGTACAGGGAGTC

CGAGACCGCCACCCAAACCCACTCCCACGAAGAGGTTGAGATCAAGCTCCCCCAGCTCGC

CGGACGGGAAGGTCAACACTCTTCATTCCAAGCCCAAGCACATCTTCCTCCCAGCGGAGA

GGGTCGCTTCAGAGAAGAAGAGGTCCGCATCACTCGTCAAGAGGAACATCACCGCCGTCC

CGGCATCCGTGAAGAGTTCGTTCACCGCGAGGAGCGTCACCGGTAAGTTTAGTTTTTGTT

TTGATTCACCACCCATTGTCTTCCCCGCCTTTTTCTTTTTCTTCCCTTGCTCTCTTGCCC

CTGTCTAGTGTAGGGCATTGCCAAGGCCATCTTCACACACACACACCCCCCCCCCCCCC

ACCCTCAGCTGGGGGGGGGGTGGCCTGGGTTGACCAAGGGACGGTGAAGACTACTACTA

CTTGAGCCACTCAAACCCATGCATGACACAGGGTTTTCCTTTTTCTTTTCTCTTTTCCTT

TAACTAACCAACCACTCCAACATTAGCCCTCAGTCAACCTACTCCGAGTCTCGCATCGAG

TTCGATACTGAGCACCGCACTCACAACTCCGTCATTGACGTTGCTGAGAGCGAGTATCGT

GCCCGTGTCCAGCCCAACTACCGCAAGGAAGCTTCCGTAGTCGGTACCACCGTCGACGGA

TCCCGCTTCAGCCACAGCCGCAAGGCCAGCAGCACCACCTCCACCCACACCGACGAGTAC

ACCGTCGATCCCCCTAGCCACCGCCCCGTCTACAAGAAGGAGTCGGTTGAAGTCGCCGGT

ACCACTGTTGACCCCCCTGCTCCTCGTTCGACCTACCACGAGCAGGTGAACATTGTTGAA

GAGACCGTTGACGCTCACCGTTACGCTCCTCAACCCAACAACAACAACACC
```

Pxy16 (SEQ ID NO: 28):
GCGGCCGCTTCCCCATGAATGGCAACCGGGCTGATGACCTGTGTGGGAAGAAATGGGGTT

GGGTCGGGCAATGGGAAGAAAACGGAAAGAGGGAAGGAAACATGCCTGTAGTCGAGGCTG

AGAGTGTACGTACGTCCGTACATTCCAGTAACCAGGCGAGAATGAGCAATGATACCCCGC

ATTTCTTGGATAATTAACTCGTTCCAGAGCACGACTTACGCAGCACTACTCCGTACTGTT

GGAGCGCTTAGCACGCTGGAAACTTGGCAGCCGTCCGAAGCCGCTCGGCCCCATCCTCTC

GCTGGTAGCTAGTGTAGTCCCGTGCTTTACAACGCGGCTATACAGCCCGTACAGTTGTAA

AGTACCTACATACATGCACTACTATTATTATCCTTCTAGAGTGGGTTCCGAATTCCAGGG

AAGATCTTCCTATGGCTATCTGGCTGAAACTTGGGGGAGGAGTGCGGAAGGGGGAGGGG

AACGAGCCTCCACATTGCATACGACCGGGGAATGCGGGACCCTAAGCGAACCAGGAACCC

GGTTATTGCACTCGGAATTGCCGCAGATCCCTGCGTTCCACCCGCTCGAACGGTCAACAT

TAACTAATCTGTAGTGGAGTTACTGTTGACTTTCTGACTCGTGTCACTGGTCCTCGCCCA

AGTTCGAAAACAGAATTGCATTTTTGTCCTTTTGTTCGGAGCTTTCGAGGAATAATTCCA

TTGTAGGTATGGAGTAATTATGGAGTATACACGGCCCAGGGGCGCTACACACACCATCGC

CGAGAATGGGAGGTCGAGCTCGCGACGCTCAGGATCCCATCGATATTTTCCCTTATCCCT

GCTCTCACTAGCGCGCAGAGCCGCCTCCGCGCGGGGATGCCGGTTGTTGCCGGCGTGCTT

TTTATCCGCTGCCCTTGGTTGCTCATTTCCCGGTTCTTGGGTCGCTTGCCAAGCAGCTCC

GGCGGAGAAGAATACCACAGGAGGGAGCATCGGGCGCGAAGGGCATTGCACTATGCGGA

CGAGATGCTTCAACACCATCATGGACCTGTCCGGAACTCCCAAGAACAGGCGACGCCAAG

GACGGAGTAGACCTCCCCGGTCCGTCTTCTCTCTGCCTGGCAATTTAGCCAAAAATCCGA

CCCGACTTGCGACGATTCCTACCTCCTAGCGCGTGCGCGCTGAAGCAGTCGCGAGAGTCG

CAAGGCATGGGCCCGAGTCTGGCTGGCATCGTCAAACGTGATCGGCCCGTCGAGCGTGCG

TGTATAAATGCATCAAGGAGCGACTGCCCCCCCATCAATAACCACCCGGTTGCTTGAGTC

TCTCGCACTCGCGGCCCCTTCTTCTCTGCTTCGCACGCATCTCGCTGTCTCGCTGTCTCG

CTGTCTCACTGTCTCGCTGTCTCACTGTCTCGCTGTCTCACTGTCTCGCTGTCTCACTGT

CTCACTCGTCCATCAGAGCAAAACC

Pgla1 (SEQ ID NO: 29):
TAGTAGTTGTCAACCTTGGCAGCGAGAGTCCCGAGGCGGTAGATGAGAGAAAAAGGACC

GATGTTGACTTCCATGCCATCGATGGCGTCGTCTCGGCTAGACGTCGTCGGCGTTATTCT

GGGGGAGGCAATCCCGGGTGAGGAGAGAAATAGACGCGTCGCCATCTAGCAGCCATCACT

CAGTGGCATCACCTGCGCGTTGACTTGCCTTCGAAGGCTCTCCTGAGCCGAGCATGTGAT

TACGATGTATAAGACCTGCATTGAGCTCGACGTTCCCGAGCGTCGGCGCGAGCTTCCAAT

TCGGTTGAGGCTCCGGCGGCTTCCCCCGGTTTCCTGCTGGACTAGCTGCCGTGGCGGGGG

GACGGCAGAGCGACTCCGACGCGCCCCATGCGAGCAACGGCCCGATTTTCGATGAGATCT

GCGGGGCGCCGGAGTGGCAGCAGTTCGTCAGCTTGGCAGGCACGGCTCCCCACCTTCTTC

CTTCTTCCACACTAGGCCCTCCCACAAGCGACCAGATGCTTGTTAAGTACGCAGTAGTGT

CTCGGCTCGCCCAGAGAACAATGGCACGCCGATCTGTCTAATGACCAAGAGCCACGGTTC

GAGACCATCCATTGGACTGGAGGGCCTGCGAGGCATCACGCCGAACCCATGTCATGCTAC

TCTTTCTGTTCACCCCCGGAGATGGCGTGAAACTGCGCGTTTACTCGCGGCTCAGCATGT

GCTCACGTTGGGTAGGTCCCGCAAAGTCAGAGGTAGGGAGGTACTTTGTAGGCACAAATC

ATGTACACGTTCGTACCTGAGGTAGCTATCTCGCCTCAGGCACACGAGGCCCGTTCGACG

-continued

AGAGAGAGGAAGAGCAACCAAGAATAGTCAAGGATATTATTACTCTTTCCCTGGTATTTC

TGGACATTTTGTCCAGGATTTTGTTCGCCCTTTAATTTTGAACAATTATGCTCCCGTCGG

CTCCGATCCACGCCTCTTAACTCTCCTTTAGCCTTTCGCCTCTATTTCCTTGAATTTCAA

TTCTCCCAAGGGCCCTGCTTTCTACAGCAAAGAATCCGTACCCTACTCTCTTTCGCGCAC

AGAGTGAGGGAGCAACAGGGATTGCGAAATGCACAGCAGAGTTTGTGTAACTTCGGCAGC

TCTTCCCCACATTCAGATGCATGTTACTGGAGAATGCGGAGAAGTTATAGTCTGGGGTAG

TAGGTATAACGCTGGTACTCCCGAGGTAGGTAGCAACCTTGGCTGACCTTGGGAAGCGAG

GGCGCTTGTGACGCTGACGATCCAGAAGCAGCCCGCCGATAGTATACGTGGAGACGGTGC

TTCTTGCTATAAGCGCTCAACTCCGCTACCCATGTTCACCGTCTTCCCCTTGGACGACGG

CATCACTCCGATACCCATGTCTCCTGGGTAGCTCCGAGTAGTCGCCCGAGCGCCCTTCTC

CCCCCTCCCCCTTTCTCCTAATAAACGGCCGAGTCGGGCAGCCTCGACGTTGCACCGTAG

CGTCGCAGCCTGCGTAGAAGCACGCGTAGAAGCACCGAGCTCCAAGCTCCAAGACGCCAA

AAGCCGCCGCGAAGTGGCCGTCGGCCCTTCCCCGCATGCGCAGCTCCGGCACCAGGTCCG

AAACGCTCCATCACCCCATATCCCAGTCAGAACAGCGGCTGCTTTCCGGATTTGGAAGTC

TGGAGGTCGCGAATGAAGGCTCGCGTTCGACTATAATAACAGCTCCGGATGGCAGGCCTC

GTTGCCCAGCTCCAGGACCACCTCCCATCCGTAAACGGATCTGGCCTCGTCACGCCCGCC

Alp1 DNA sequence comprises (SEQ ID NO: 30):
ATGCACTTCTCCACCGCTCTCCTGGCCTTCCTGCCCGCCGCCCTCGCGGCCCCTACTGCCG

AGACCCTCGACAAGCGCGCCCCGATCCTGACTGCTCGCGCTGGCCAGGTCGTCCCGGGCAA

GTACATCATCAAGCTCCGCGACGGAGCCAGCGACGATGTCCTTGAGGCCGCCATCGGCAAG

CTCCGCTCCAAGGCCGACCACGTCTACCGCGGCAAGTTCAGGGGCTTTGCCGGCAAGCTCG

AGGATGACGTCCTTGACGCCATCCGTCTTCTCCCCGAAgtgagtccgcgtcccggaaagaa

Atagagcgagcggggagagagtgaagggcgaaaagagccgtgttttgttaaccgcttgtc ttttctttctctcttgcaatagGTCGAGTACGTCGAGGAGGAGGCCATCTTCACCATCAAC

GCGTACACCTCGCAGTCCAACGCCCCCTGGGGCCTTGCGCGCCTCTCGTCCAAGACCGCGG

GCTCCACCACCTACACCTACGACACCAGCGCCGGCGAGGGCACCTGTGCCTATGTGATCGA

CACGGGCATCTACACTAGCCACTCCgtatgtctcgcggttacctcccctttcggaagaagg ggcatccatatgctgacccctcctgatcacagGACTTCGGCGGCCGTGCCACTTTCGCCGC

CAACTTCGTCGACAGCTCTAACACCGATGGCAACGGCCACGGCACCCACGTCGCCGGCACC

ATCGGCGGCACCACGTACGGTGTTGCCAAGAAGACCAAGCTCTACGCCGTCAAGGTTCTCG

GCTCCGACGGCTCTGGCACCACgtatgcctcgcacccgcgcacccgcacacccgcccggcc gttatcttctgactgacattcctcttttctcctctctagTTCTGGTGTCATTGCTGGCATCA

ACTTCGTCGCTGACGACGCGCCCAAGCGCAGCTGCCCCAAGGGCGTCGTCGCCAACATGTC

GCTCGGCGGTAGCTACTCGGCCTCCATCAACAACGCCGCCGCCGCCCTCGTCAGGTCGGGC

GTCTTCCTGGCCGTCGCCGCCGGCAACGAGAACCAGAACGCCGCCAACTCGTCGCCCGCCT

CCGAGGCGTCCGCCTGCACCGTCGGCGCCACCGACAGGAACGACGCCAAGGCCAGCTACTC

CAACTACGGCAGCGTCGTCGATATCCAGGCCCCCGGCTCCAACATCCTGAGCACCTGGATC

GGCAGCACCTCTGCTACCgtaagccccccctcccccacccaccccagcctttggcgaca

Ttcccgccccgtatttatttctccggggtgggggagaaacaaaacaaaatagctaacatga gatgcactctcagAACACCATCTCGGGTACCTCGATGGCCTCCCCCCACATTGCCGGCCTC

GGTGCCTACCTCCTGGCCCTCGAGGGCTCCAAGACCCCTGCCGAGCTCTGCAACTACATCA

-continued

AGTCGACCGGCAACGCCGCCATCACTGGCGTTCCCAGCGGCACCACCAACCGCATCGCCTT

CAACGGCAACCCCTCTGCCtga

Alp1 amino acid sequence (SEQ ID NO: 31):

MHFSTALLAF LPAALAAPTA ETLDKRAPIL TARAGQVVPG KYIIKLRDGA SDDVLEAAIG 61

KLRSKADHVY RGKFRGFAGK LEDDVLDAIR LLPEVEYVEE EAIFTINAYT SQSNAPWGLA 121

RLSSKTAGST TYTYDTSAGE GTCAYVIDTG IYTSHSDFGG RATFAANFVD SSNTDGNGHG 181

THVAGTIGGT TYGVAKKTKL YAVKVLGSDG SGTTSGVIAG INFVADDAPK RSCPKGVVAN 241

MSLGGSYSAS INNAAAALVR SGVFLAVAAG NENQNAANSS PASEASACTV GATDRNDAKA 301

SYSNYGSVVD IQAPGSNILS TWIGSTSATN TISGTSMASP HIAGLGAYLL ALEGSKTPAE 361

LCNYIKSTGN AAITGVPSGT TNRIAFNGNP SA

LIST OF REFERENCES

Braaksma, M. and P. J. Punt. 2008. *Aspergillus* as a cell factory for protein production: controlling protease activity in fungal production, p. 441-455. In: G. H. Goldman and S. A. Osmani (eds.), The Aspergilli: Genomics, Medical Aspects, Biotechnology, and Research Methods, CRC Press, Boca Raton Verdoes, J. C., Punt, P. J., Burlingame, R., Bartels, J., van Dijk, R., Slump, E., Meens, M., Joosten, R. and Emalfarb, M., 2007. A dedicated vector for efficient library construction and high throughput screening in the hyphal fungus *Chrysosporium lucknowense. Industrial Biotechnology* 3:48-57.

What is claimed is:

1. A chimeric gene comprising:
   (i) the nucleotide sequence of SEQ ID NO:26, or
   (ii) a transcriptionally active part of the nucleotide sequence of SEQ ID NO:26 that comprises the nucleotide sequence of SEQ ID NO:25.

2. A fungal host cell comprising the chimeric gene of claim 1.

3. The host cell of claim 2, wherein said host cell is a *Chrysosporium lucknowense* C1 cell or a derivative thereof.

4. The host cell of claim 3, wherein said host cell is selected from the group consisting of:
   (a) *Chrysosporium lucknowense* C1 strain UV18-25 deposited in the All Russian Collection Microorganisms (VKM) as Deposit No. VKM F3631 D, and
   (b) a derivative of said *Chrysosporium lucknowense* C1 strain of (a).

5. The host cell of claim 4, wherein said host cell is selected from the group consisting of:
   (a) W1L, deposited at CBS under accession number 122189, and
   (b) W1L #100.1, deposited at CBS under accession number 122190.

6. A method for homologous or heterologous production of a protein comprising expressing the chimeric gene of claim 1 in a fungal host cell, thereby producing said protein.

7. The method of claim 6, wherein the said host cell is a *Chrysosporium lucknowense* C1 cell or a derivative thereof.

8. The method of claim 7, wherein the said host cell is selected from the group consisting of:
   (a) W1L, deposited at CBS under accession number 122189, and
   (b) W1L #100.1, deposited at CBS under accession number 122190.

9. The chimeric gene of claim 1, wherein said chimeric gene comprises the nucleotide sequence of SEQ ID NO:26.

* * * * *

SEQUENCE LISTING

<160> NUMBER OF SEQ ID NOS: 31

<210> SEQ ID NO 1
<211> LENGTH: 12
<212> TYPE: PRT
<213> ORGANISM: Chrysosporium lucknowense

<400> SEQUENCE: 1

```
Thr Gly Gly Trp Ser Val Val Trp Pro Val Leu Lys
1               5                   10
```

<210> SEQ ID NO 2
<211> LENGTH: 15
<212> TYPE: PRT
<213> ORGANISM: Chrysosporium lucknowense
<220> FEATURE:
<221> NAME/KEY: MISC_FEATURE
<222> LOCATION: (8)..(8)
<223> OTHER INFORMATION: Xaa = Leu or Ile

<400> SEQUENCE: 2

```
Val Val Gly Ser Ser Ser Glu Xaa Gly Asn Trp Asp Thr Gly Arg
1               5                   10                  15
```

<210> SEQ ID NO 3
<211> LENGTH: 9
<212> TYPE: PRT
<213> ORGANISM: Chrysosporium lucknowense

<400> SEQUENCE: 3

```
Thr Ile Asp Ala Met Ala Trp Ser Lys
1               5
```

<210> SEQ ID NO 4
<211> LENGTH: 10
<212> TYPE: PRT
<213> ORGANISM: Chrysosporium lucknowense

<400> SEQUENCE: 4

Asn Phe Leu Pro Val Ala Asp Ile Leu Arg
1               5                   10

<210> SEQ ID NO 5
<211> LENGTH: 16
<212> TYPE: PRT
<213> ORGANISM: Chrysosporium lucknowense

<400> SEQUENCE: 5

Gly Ala Tyr His Pro Ser Gln Thr Tyr Ser Pro Glu Asp Val Glu Lys
1               5                   10                  15

<210> SEQ ID NO 6
<211> LENGTH: 20
<212> TYPE: PRT
<213> ORGANISM: Chrysosporium lucknowense

<400> SEQUENCE: 6

Ser Trp Gln Leu Val Tyr Gln His Asp Pro Thr Ala Gly Leu Thr Ala
1               5                   10                  15

Glu Glu Ala Lys
            20

<210> SEQ ID NO 7
<211> LENGTH: 18
<212> TYPE: PRT
<213> ORGANISM: Chrysosporium lucknowense

<400> SEQUENCE: 7

Pro Gln Tyr Glu Ser Ala Gly Ser Val Val Pro Ser Ser Phe Leu Ser
1               5                   10                  15

Val Arg

<210> SEQ ID NO 8
<211> LENGTH: 17
<212> TYPE: PRT
<213> ORGANISM: Chrysosporium lucknowense

<400> SEQUENCE: 8

Val Ser Gly Gln Val Glu Leu Thr Asp Phe Leu Val Ser Thr Gln Gly
1               5                   10                  15

Arg

<210> SEQ ID NO 9
<211> LENGTH: 7
<212> TYPE: PRT
<213> ORGANISM: Chrysosporium lucknowense

<400> SEQUENCE: 9

Met Val Tyr Asp Tyr Ala Gly
1               5

<210> SEQ ID NO 10
<211> LENGTH: 20
<212> TYPE: DNA
<213> ORGANISM: Artificial
<220> FEATURE:
<223> OTHER INFORMATION: synthetic

<400> SEQUENCE: 10
atggtstacg actacgcbgg                                              20

<210> SEQ ID NO 11

-continued

<211> LENGTH: 7
<212> TYPE: PRT
<213> ORGANISM: Chrysosporium lucknowense

<400> SEQUENCE: 11

Met Pro Ile Tyr Gly Arg Ser
1 5

<210> SEQ ID NO 12
<211> LENGTH: 17
<212> TYPE: DNA
<213> ORGANISM: Artificial
<220> FEATURE:
<223> OTHER INFORMATION: synthetic

<400> SEQUENCE: 12
atgccsatct acggycg 17

<210> SEQ ID NO 13
<211> LENGTH: 17
<212> TYPE: DNA
<213> ORGANISM: Artificial
<220> FEATURE:
<223> OTHER INFORMATION: synthetic

<400> SEQUENCE: 13
cgrccgtaga tsggcat 17

<210> SEQ ID NO 14
<211> LENGTH: 7
<212> TYPE: PRT
<213> ORGANISM: Chrysosporium lucknowense
<220> FEATURE:
<221> NAME/KEY: MISC_FEATURE
<222> LOCATION: (3)..(3)
<223> OTHER INFORMATION: Xaa is any amino acid

<400> SEQUENCE: 14

Met Phe Xaa Glu Ala Ser Ala
1 5

<210> SEQ ID NO 15
<211> LENGTH: 20
<212> TYPE: DNA
<213> ORGANISM: Artificial
<220> FEATURE:
<223> OTHER INFORMATION: synthetic

<400> SEQUENCE: 15
gcsswvgcct cccagaacat 20

<210> SEQ ID NO 16
<211> LENGTH: 9
<212> TYPE: PRT
<213> ORGANISM: Chrysosporium lucknowense

<400> SEQUENCE: 16

Asp Gly Ile Asp Ile Asp Trp Glu Val
1 5

<210> SEQ ID NO 17
<211> LENGTH: 22
<212> TYPE: DNA
<213> ORGANISM: Artificial
<220> FEATURE:
<223> OTHER INFORMATION: synthetic

<400> SEQUENCE: 17
gayggyatcg ayrtsgaytg gg 22

<210> SEQ ID NO 18
<211> LENGTH: 173
<212> TYPE: DNA
<213> ORGANISM: Chrysosporium lucknowense

<400> SEQUENCE: 18
atgggctacg actacgccgg ctcgtggagc accgcggcgg gacaccaggc caacctgtac 60
ccgaccgccg acgcgggcag gacgcccttc tcgaccgaca aggccctgtc cgactacgtc 120
gccgccggcg tcgacccggc caagatcgtg ctcggcatgc ccatctacgg ccg 173

<210> SEQ ID NO 19
<211> LENGTH: 4680
<212> TYPE: DNA
<213> ORGANISM: Chrysosporium lucknowense

<400> SEQUENCE: 19
gctggctcac cgttatttgc tcccgcagga agtccaggtc ctcctcgcag ttggacaaac 60
tctgcttcgc agcctgcaac tttgactcaa ggagcgcctc ggcctcgtcg attgggtaag 120
acagcatgac gttggcctgc caaatgtcag cctctagaag cacactccca ctctcgttgg 180
aaaggttcct accccaagcc acaagtaaac ctcgtccgtc ggcggtatct cggccttcgc 240
atagagagtg tcgttcaatt cgaatgttgt ctctatcgga tcagattcgc cctgccacaa 300
tcaaccgccg atcagcacca tggccgctca tcgagagtgg caacgcctcg ccctaccgtc 360
ctcagcttca aaaagcggac agcctccagc gttttccgaa tgtcgggcat tttgtccttt 420
agtcccgcta ccctccgctg caggttctgc tccatgaact ggtatttcct gcacgccgac 480
cacgtatcag ccgaacgccg tccgtcaagg ctggatttca atcttaaccg ggagagctca 540
cgcaatcatc tcttggaacc gacgcagcgt cggctcaaca tctgctcgtg acgtgacata 600
gtcctcgacc ttgtcgacga atggcgcata cggaatgcca cgaggattgg agggtgtggc 660
gtccctgtct cgtgcaggtg gtcagtcagc aataacagcc agagtgcata tgctagaatg 720
gcgcccgcgg gggagggaaa gtttggttac cttgctgctg cttccttgtc tgtgctcgcc 780
atcttggaca aattctcaca tgttgcagtg gaaggatact gcaagcgact gttaacccga 840
gccaacggag tgacgtcggg tttggtacct agtttaggtc aagccgttct caagctgctg 900
gccaaaaatt catggcgggg tcgagtgggc agcgaggtac tcctcgtagg gagcaaggtg 960
aagatgtggg gtagcagggg tcgacgctac aaagtacttt gtatccggat tgctgtgtgg 1020
tacgaagcgc ccgtgtgttg gatgctctct gtatgtacgg agtactgtac ctttctccat 1080
gcgctgcccc attctctatt tggttgcacc tgcttcgttc gtagtgtatg tacagcagta 1140
caactatcta cgacacctgc actgactagt gcgtagaatt ctttagtttc tcgagtacgg 1200
cgctaacgct tcgcgcagca agcaccttct tctgattgtg ttactgtgct caaacctcgc 1260
cagccagctg cggtgctcca caagcccggc cgtgcccaac cgccatttgc atcccggtcc 1320
catgaatctg tggacgaccc atccctctct gtaccgcgtc gcggtatcag cccagaatga 1380
tagcgggaag acaaacgcag tgattcggat tacgctcgca ggaaatgggg ggagtagctt 1440
gatagctctc cacggcgagg gtgtctcagg ctgaggtgtc aactagttgt atgtacactc 1500
aggacgaggc attctgcgtt ttgaaacacc aatcttccaa taccggaggt gttgtatgca 1560
ggatcacttg aatatgtttg cacccattat tactgtacct ggatgattcg gacagggcga 1620

```
gcatgattgg tcgccccgtt ttgtcaccgc attcgcagcg tcggcgggaa gcagccacgt    1680
agagcactgc caaacgtttc aagagacacc ccatatggag taaattggag taatctgtat    1740
ccttcagagc cgtcaatcaa actattgttt ctcagcagga tggcccgttg ctcatggggg    1800
atgtaccctg gtaggtagtt cgttgttgat gacttccttg gatgagcctg ctgcgcatga    1860
aggtgccggg gccccaggtt gggtgcctaa aactaactgt aaacagacgc acggtggcga    1920
cgacgtagcc gaaccggtgt agcgagcttt ccccggccac tacgtaatcg gggcgatgca    1980
ctgcaggaac acctcacacc tgacctaccc ccttcgcctc cgcatccgtc caacccgct     2040 tccccaacct ttccatcaac tacttccgag actcgacatc accttttcgc gtcgtgtctc    2100
atcgtcgtta tcatcaccat cggcgataga tttgttcgct tcgatcgtcg catcgccttg    2160
acttccattc gtccttcacg ccgaccgacc ggaccagaca gtcgcccaaa atgaaggatg    2220
cttttttgct gaccgcagct gtgctgctcg gctccgccca gggagcagtt cacaaaatga    2280
agctgcagaa gatccctctc tctgagcagc ttgtacgtct gaccccgttc aagcacgcgt    2340
cagcggctac tgaccttatc gcgtccagga ggcggttccc atcaacaccc agctcgagca    2400
tctcggccaa aaatacatgg ggttgcgccc acgtgaatct caagccgatg ccatctttaa    2460
gggcatggtt gccgacgtca agggcaacca tcctattccc atctccaact tcatgaacgc    2520
acagtgtatg tgacgccact gtggtggcat ggatggctcg tcctcaattc ggagactgac    2580
actggagcac cctagacttc tccgagatca cgattggaac accccctcag tcattcaagg    2640
tggtcctcga taccggtagc tccaacctgt gggttccatc agtcgagtgc ggctcgattg    2700
cttgttacct gcactcgaag tatgactcat ctgcctcgtc cacctacaag aagaacggaa    2760
cctcgttcga gatccgctac gggtcaggca gcctgagcgg gtttgtctct caggacacag    2820
tgtccatcgg cgatatcact atccagggcc aggactttgc cgaggcgacc agcgagcccg    2880
gtcttgcctt tgcctttggc cgtttcgacg gtatccttgg ccttggctac gaccggatct    2940
cagtcaacgg catcgtcccg cctttttaca agatggtcga gcagaagctc atcgatgagc    3000
ccgtcttcgc cttctacctg gccgatacca atggccagtc tgaggttgtc tttggcggtg    3060
ttgaccacga caagtacaag ggcaagatca ccaccattcc gttgaggcgc aaggcctact    3120
gggaggttga cttcgatgcc atttcttacg gcgacgacac tgccgagctt gagaacactg    3180
gcatcatcct ggacaccggt acttctctga tcgctctgcc cagccagctc gccgagatgc    3240
tcaacgctca gatcggcgct aagaagagct acactggcca gtacaccatc gactgcaaca    3300
agcgcgactc cctcaaggat gtcacgttca acctggctgg ctacaatttc acgctcggcc    3360
cctacgacta cgttctcgag gtccagggca gctgcatttc tacctttatg ggcatggatt    3420
tcccggctcc tactgggcca cttgcgatcc tgggcgatgc cttcctccgg aggtattact    3480
ccatttatga ccttggcgcc gacaccgtcg gtctggctga ggccaagtga ttgaaggatg    3540
ggcggcaggg aaagacgatg ggtaatacgg ggagtctggg aatcgggctt tggactgtgg    3600
tctgtatcta gttgctcaag agagttgtcg tttgattttg ttataggatc tgtctaggaa    3660
ccttagcagg agtgaaattt tttcgtgtac gagcatcggc gggctgaagt ggtttgataa    3720
caagtctgga cttgagtacg caggcagttg cacaatctgc ttcgccgagg agagcaaagg    3780
cgtcctcttt gaaaaagcct acctacgcgt cacaggggta taattttttg agtttgacct    3840
acgccctgtc ccataccaac cgcgtcccaa tcccgtcaa cccttgcaat gtcattaccc     3900
gtggatgtat cacgtagcag aagccgacat cccacacgct tcaaccttcc tatccagaca    3960
```

-continued

```
atgacatggt aagctcattt tttaaaggtc gccgtcctcc ctcccttcac gtgattcatt    4020
ttccttgcgc cttgtggcgc atccctgac ttcatgccgt acggatcaaa gggtgcaaac     4080
ttgccccgca cctctttct gccgccatca tcatcaccat catcgccgtt tgtcgcctgc     4140
gcagcatgta gcacggacga cgccttgctg tagtcaaacg gctcctgctc ggcatcgtca    4200
tcatggcctt cctcctgttc gcccgaggtc tgttcgtcgg ctgccgaggt cgcggcggag   4260
gcagatgtct gctgctgctg ctgctgctgc tgcttctggg cttcttggc ggctcgaagt    4320 gccttcctgg cttgagcctt gagttccttt gctccctta tgtctccgtt ttgagccagt    4380
tgctctgcca agagctgagc acgcttgaac tcttctcgag cagccttctt ggcttgtttc    4440
tttgcctgct tggcggcctt gtcatcacca ccctcaactt cctgctcgac actaggagac   4500
ttcgggtggt ctttgcctgc ggaactatct ccacccatct cgatgtcgga aactgcttcg   4560
gcttcggatg ctgactcaac atcaacatcc ctagacttcc gctttcgacc agccttcaga   4620
gtgaaacctt cttcttcgag aacagggaga cccttggtgt cttgttcagc gacacgcctg   4680
```

<210> SEQ ID NO 20
<211> LENGTH: 397
<212> TYPE: PRT
<213> ORGANISM: Chrysosporium lucknowense

<400> SEQUENCE: 20

```
Met Lys Asp Ala Phe Leu Leu Thr Ala Ala Val Leu Leu Gly Ser Ala
1               5                   10                  15

Gln Gly Ala Val His Lys Met Lys Leu Gln Lys Ile Pro Leu Ser Glu
            20                  25                  30

Gln Leu Glu Ala Val Pro Ile Asn Thr Gln Leu Glu His Leu Gly Gln
        35                  40                  45

Lys Tyr Met Gly Leu Arg Pro Arg Glu Ser Gln Ala Asp Ala Ile Phe
    50                  55                  60

Lys Gly Met Val Ala Asp Val Lys Gly Asn His Pro Ile Pro Ile Ser
65                  70                  75                  80

Asn Phe Met Asn Ala Gln Tyr Phe Ser Glu Ile Thr Ile Gly Thr Pro
                85                  90                  95

Pro Gln Ser Phe Lys Val Val Leu Asp Thr Gly Ser Ser Asn Leu Trp
            100                 105                 110

Val Pro Ser Val Glu Cys Gly Ser Ile Ala Cys Tyr Leu His Ser Lys
        115                 120                 125

Tyr Asp Ser Ser Ala Ser Ser Thr Tyr Lys Lys Asn Gly Thr Ser Phe
    130                 135                 140

Glu Ile Arg Tyr Gly Ser Gly Ser Leu Ser Gly Phe Val Ser Gln Asp
145                 150                 155                 160

Thr Val Ser Ile Gly Asp Ile Thr Ile Gln Gly Gln Asp Phe Ala Glu
                165                 170                 175

Ala Thr Ser Glu Pro Gly Leu Ala Phe Ala Phe Gly Arg Phe Asp Gly
            180                 185                 190

Ile Leu Gly Leu Gly Tyr Asp Arg Ile Ser Val Asn Gly Ile Val Pro
        195                 200                 205

Pro Phe Tyr Lys Met Val Glu Gln Lys Leu Ile Asp Glu Pro Val Phe
    210                 215                 220

Ala Phe Tyr Leu Ala Asp Thr Asn Gly Gln Ser Glu Val Val Phe Gly
225                 230                 235                 240

Gly Val Asp His Asp Lys Tyr Lys Gly Lys Met Thr Thr Ile Pro Leu
                245                 250                 255
```

```
Arg Arg Lys Ala Tyr Trp Glu Val Asp Phe Asp Ala Ile Ser Tyr Gly
            260                 265                 270

Asp Asp Thr Ala Glu Leu Glu Asn Thr Gly Ile Ile Leu Asp Thr Gly
            275                 280                 285

Thr Ser Leu Ile Ala Leu Pro Ser Gln Leu Ala Glu Met Leu Asn Ala
        290                 295                 300

Gln Ile Gly Ala Lys Lys Ser Tyr Thr Gly Gln Tyr Thr Ile Asp Cys
305                 310                 315                 320

Asn Lys Arg Asp Ser Leu Lys Asp Val Thr Phe Asn Leu Ala Gly Tyr
                325                 330                 335

Asn Phe Thr Leu Gly Pro Tyr Asp Tyr Val Leu Glu Val Gln Gly Ser
            340                 345                 350

Cys Ile Ser Thr Phe Met Gly Met Asp Phe Pro Ala Pro Thr Gly Pro
        355                 360                 365

Leu Ala Ile Leu Gly Asp Ala Phe Leu Arg Arg Tyr Tyr Ser Ile Tyr
    370                 375                 380

Asp Leu Gly Ala Asp Thr Val Gly Leu Ala Glu Ala Lys
385                 390                 395

<210> SEQ ID NO 21
<211> LENGTH: 2220
<212> TYPE: DNA
<213> ORGANISM: Chrysosporium lucknowense

<400> SEQUENCE: 21
cattcatggg tttgaggccc gattttgaac gtatatccta ggctatattc ggggtaagat    60
actggaagcg ctgggccgga tgactagcta tttcaagtgc ccaagagccc atcataccta   120
acttgtggcc taagatctag ccaaatcatt cattggttac cccagactcg acgaacctga   180
tattcgaatc cagggcaagt caaatcgccg agtaagactt gacaaacccg aacccaaga    240 actgcgcaat ctgggagcag gtttccgacc agcatggaaa caccccgatg aaaacccac    300 acatacgggg atgggactaa cgccggacaa atcaaaaac cctggaggat tgggtaacga    360
tggggaagtg cgacgggcac tcaaccccttc aagcgttgca ggaccttgta cagccaagca    420
gaatgacgga aaccgatgag caaacccgga atctgatgat cctggaacag aatcatctgt    480
cttgggtacc gacgttggag tgagagtgtg caaattagca ggatcaagca actatactac    540
ctaaatcagg tcgatcagtt atcagcccctt gcaaaccaga cttgatggag ggaagaggtg    600
aaagctgtga ttgagggagg aagctgagaa ttggtggtgg ttgttttgct cagccagggt    660
gtaggacgag aagaacgcgt tcgagatttc ggagagcagg ctgtcctaga gcattatttt    720
cctggccttg agcaaactta agccagtttt ttttccccg tcgggaggga agtcgctttg    780
aatttgaagc ttgcgggcgc agagctcggc tccataagca tccaatcaaa tgagcctgaa    840
gcagtcgacc gattttttt tatctgggtg taatcgcaac catgcacata accgttttgg    900
gactagctcc aacagctctg atcaacaacc tgagaaaggc gcgagtgatc cgtgatccca    960 caccettacg cgaaaactac ttaactccca cctcccccac cgcgggtcaa cttcttccaa   1020
ctcccactca accaacttcc gttttcccat caatcactgc attcgcgcgt caagctcttc   1080 ctcgcccta caccaaccac ataacttttt tatcctttga caaggaccat caatcaaaat   1140
gactggcggc ggcaagtccg gtggcaaggc gagcggttcc aagaacgcgc aatcgtaggt   1200
gcccttttcg cgtcatctac ccgcgccttc gtgcagttgg gcatggttca gccttgaact   1260
ccagatgccc gttccggtgc tcttacagtt ggctaacttt ttgtagtcgt tcatctaagg   1320
```

```
ccggtcttgc gttccctgtc ggtcgtgtcc accgccttct ccggaagggc aactacgccc   1380
agcgtgtcgg tgccggtgct cccgtttacc tggctgccgt tctcgagtat cttgccgctg   1440
aaattctgga gctggctggc aacgccgctc gcgacaacaa gaagacgcgt atcatcccgc   1500
gtcacttgca actcgctatc aggaacgatg aggagttgaa caagcttctc gggcacgtca   1560
ccatcgccca gggtggtgtc cttcccaaca tccaccagag tacgttgcct taccagacga   1620
tctctaatgc gcaaatctaa cttttgtttcc agaccttctg ccgaagaaga ccggcaagac   1680
cggcaagaac ttgtcgcagg agctctgatt tcgcggttgg gttttttttg ctttattttc   1740
tggtcggcac gctgggttca tgatatcggg gtcacggttt cgggtcattg gttgcttttt   1800
gcgcgtgttt gggctgtaca ttaattccat gatgggcatg gtcatggtta tgaatgagaa   1860
tatcctctga acatccaaat cctgacacag tttgctcgag ttgatgtctg cattggaagc   1920
gactcgttga cggtaccgcg tagagtcttg tcgcttacga aattcttgca tcgcacagat   1980
tacccagtag tgccatagta ctctttaaga tgataagtgc atttgagccc ggcatcgcac   2040
agactttccc atgccttgat atatgcgaat tcctatgtac aagagattcg tcgcgaaaga   2100
gcccgtcaaa acttgagcgg ggggggagct gcaaaagcct gtcagctaat tcgagtgaga   2160
cgcgcaaagc aagccaactt acgatccagg tggggcgccg ggaggtttct ctcgtatttc   2220
```

```
<210> SEQ ID NO 22
<211> LENGTH: 134
<212> TYPE: PRT
<213> ORGANISM: Chrysosporium lucknowense

<400> SEQUENCE: 22

Met Thr Gly Gly Gly Lys Ser Gly Gly Lys Ala Ser Gly Ser Lys Asn
1               5                   10                  15

Ala Gln Ser Arg Ser Ser Lys Ala Gly Leu Ala Phe Pro Val Gly Arg
            20                  25                  30

Val His Arg Leu Leu Arg Lys Gly Asn Tyr Ala Gln Arg Val Gly Ala
        35                  40                  45

Gly Ala Pro Val Tyr Leu Ala Ala Val Leu Glu Tyr Leu Ala Ala Glu
    50                  55                  60

Ile Leu Glu Leu Ala Gly Asn Ala Ala Arg Asp Asn Lys Lys Thr Arg
65                  70                  75                  80

Ile Ile Pro Arg His Leu Gln Leu Ala Ile Arg Asn Asp Glu Glu Leu
                85                  90                  95

Asn Lys Leu Leu Gly His Val Thr Ile Ala Gln Gly Gly Val Leu Pro
            100                 105                 110

Asn Ile His Gln Asn Leu Leu Pro Lys Lys Thr Gly Lys Thr Gly Lys
        115                 120                 125

Asn Leu Ser Gln Glu Leu
    130
```

```
<210> SEQ ID NO 23
<211> LENGTH: 1740
<212> TYPE: DNA
<213> ORGANISM: Chrysosporium lucknowense

<400> SEQUENCE: 23
gtcaacttac tccgagtctc gcatcgagtt cgatactgag caccgtactc acaactccgt     60
cattgacgtt gctgagggcg agtatcgtgc ccgtgtccag cccaaccacc gcaagcaagc    120
ttccgtagtc ggtaccaccg tcaacggatc gcggttcagc cacagccgca aggccagcag    180
```

```
caccacctcc acccacaccg acgagtacac cgtcgatccc cctagccacc gccccgtcta    240
caagaaggag tcggttgaag tcgccggtac cactgttgac ccccctgctc ctcgttcgac    300
ctaccacgag caggtgaaca ttgttgaaga gaccgttgac gctcaccgtt acgctcctca    360
acccaacaac aacaacaaga tgggctacta cgacgaggac ggtaagcatc ttccttcccc    420
tttgatgttg ttccttaccc gtgacatcca tcggtcgtat gctttcttag ccacacacaa    480
gtgttgtgac aagtgccgtg ctcacgccga tatcaggcca ctaccactct ttccgccatg    540
gattgcacaa gttggctgac cgtattgcgc atcctgaagg ccatgaccgc gttgaggtga    600
gcgaggttcg tgagacccgc cgcacccgcg ctccgtcttc ggaggcgtac acgccgaaca    660
cggtcaccat tccgtgccac cacatccgcc tcggcgacat cctgatcctc cagggccgcc    720
cctgccaggt catccgtatc tcgacctcgg ctgccactgg ccagcaccgc tatcttggtg    780
tcgacctctt caccaagcag ctccatgagg agtcgtcgtt cgtctcgaac cctgctccca    840
gcgtcgtcgt ccagacgatg cttggccctg ttttcaagca gtaccgcgtc ctcgacatgc    900
aggacggcca catcgtcgcc atgaccgaga cgggcgatgt caagcagaac ctgcccgtca    960
tcgaccagag caacctctgg ggccgcctca agcaggcctt cgagactggc cgcggcagcg   1020
tccgtgtcct ggtcgtttct gacaacggca acgagatggc tgttgacatg aaggtcgtcc   1080
acggctcgcg cctctaagtc aagccggcag gctttcatgc aagctttggg gctacgagtc   1140
gggcggcatt gggtttgcgt ttgatgcatc ttggttacgg cgtgtatgtc atttgaagat   1200
tgaaagctgc gccttggtcg actcctggcg ccggatggat atacatgttc ctcgggagga   1260
tatgaaggtt tcatgtcgct agtttcacgt gtatatgatg actgtaatgg atggatgttt   1320
atggccaact ttgcgattga tatcttgaac ctttttttctg gtcgtgtgag tgaacagtga   1380
ttaagtgaga gtgaggtatg caccgtttat cacaaggttg ccttgatatc ccaccttcaa   1440
cgggcgtggg gaatcgaagt ccctccccta cagtaagtag cctctcttga atgatctgaa   1500
acgcaacccc tccgagccac taccacacct aactacgaaa caaccacttt cctgttccag   1560
gaagctccag ttctcccgct accctcccct cccgccgttc aggttgtacg cttatctccc   1620
aacctcatct tcgagaggtc taatccgtac acacttaaca gtgcatcctg acatagctaa   1680
ccatcatcac tctagttcat tagccgtccc gccatcccgt caattacatt cccggctgtt   1740
```

<210> SEQ ID NO 24
<211> LENGTH: 200
<212> TYPE: PRT
<213> ORGANISM: Chrysosporium lucknowense

<400> SEQUENCE: 24

```
Met Gly Tyr Tyr Asp Glu Asp Gly His Tyr His Ser Phe Arg His Gly
1               5                   10                  15

Leu His Lys Leu Ala Asp Arg Ile Ala His Pro Glu Gly His Asp Arg
            20                  25                  30

Val Glu Val Ser Glu Val Arg Glu Thr Arg Arg Thr Arg Ala Pro Ser
        35                  40                  45

Ser Glu Ala Tyr Thr Pro Asn Thr Val Thr Ile Pro Cys His His Ile
    50                  55                  60

Arg Leu Gly Asp Ile Leu Ile Leu Gln Gly Arg Pro Cys Gln Val Ile
65                  70                  75                  80

Arg Ile Ser Thr Ser Ala Ala Thr Gly Gln His Arg Tyr Leu Gly Val
                85                  90                  95
```

-continued

```
Asp Leu Phe Thr Lys Gln Leu His Glu Glu Ser Ser Phe Val Ser Asn
            100                 105                 110

Pro Ala Pro Ser Val Val Val Gln Thr Met Leu Gly Pro Val Phe Lys
        115                 120                 125

Gln Tyr Arg Val Leu Asp Met Gln Asp Gly His Ile Val Ala Met Thr
    130                 135                 140

Glu Thr Gly Asp Val Lys Gln Asn Leu Pro Val Ile Asp Gln Ser Asn
145                 150                 155                 160

Leu Trp Gly Arg Leu Lys Gln Ala Phe Glu Thr Gly Arg Gly Ser Val
                165                 170                 175

Arg Val Leu Val Val Ser Asp Asn Gly Asn Glu Met Ala Val Asp Met
            180                 185                 190

Lys Val Val His Gly Ser Arg Leu
        195                 200

<210> SEQ ID NO 25
<211> LENGTH: 779
<212> TYPE: DNA
<213> ORGANISM: Chrysosporium lucknowense
<220> FEATURE:
<221> NAME/KEY: misc_feature
<222> LOCATION: (675)..(675)
<223> OTHER INFORMATION: n = any nucleotide

<400> SEQUENCE: 25
agcttgaccc tttcagagct aggtttcatt aggccttcga aaacaaccca aggccccgtc      60
gcaaccatca caaccggccg ataaccagat ctcggtaggt ccgataagga tccaaaatgg     120
tgtcggctga cgttgcatgt gcccaggcag gaggatgatc cccagggttg ttgccggcag     180
ctcccgcacg tcggggaggg ggagggggag gggaaagccc taactaacgt tcgttctatc     240
acgggccgac cgggccatgc tttcggcttg tgagcggtgg ggtcaagggc aacaagaaat     300
gctaagtgcg ggacgaagac acgcgggcat gaggtctcag ggtgacctgc gcaaaaccaa     360
gtcccactcg ccatgcctcc agcagcaacg ttgccgtaga agggtcaggg ggtttgttgt     420
agacccacga ccatgctgcc ggcgagcgga gggttggctt gctacaggcg ctgaagggtc     480
aactcggtgc ccaaagtggc taccaagcgt gccatcaagg gaaatgagat gatggtggct     540
cgtgggcaaa gaaaagacaa gggaggtgac tctagagaga tgctctcgag ttcacgggta     600
taagagcact gtgatcgttc acaaagccgg cgtactcctc tagagcatct atcatcaaca     660
tcaccagaaa ggtcntagac caggtggttg ccatatccag tcgcaaaaga gccaaagagc     720
gaaggagcac gaaagcacag cccaatcatt ccctgctttg ctacttcttc tccaccatg      779

<210> SEQ ID NO 26
<211> LENGTH: 1818
<212> TYPE: DNA
<213> ORGANISM: Chrysosporium lucknowense
<220> FEATURE:
<221> NAME/KEY: misc_feature
<222> LOCATION: (1714)..(1714)
<223> OTHER INFORMATION: n = any nucleotide

<400> SEQUENCE: 26
gtcccttacc tatgggctcc tagtctcgtt cctctttttg atagatttgt attttgcaac      60
gttgcaaaat gagacatttc aatcatatgt agccgccagc tactgttagc gtactcagcg     120
ttgcccaaac ggcggttttt ctgggtagca ctgtgccgcg tgcccctgag ccgtgcgtcg     180
cggaaacccc cttaagtagc aagtatgtta ccgccgagac cgacaatgct gttggttacc     240
```

```
tcgctggtcc atgattgcaa tctagatatc gtgcggggct tttgcaatcg gttttcccta    300
cccactttct tcttttggac actttctctt ttggaaaatg ccgaaatgat gcggctcgct    360
cacgccccga agtcccgagc tggggctaga tccgtgattg caacgcggtg cgaacgcgac    420
tggggcagac ctcgctcagc cttggtcgtg ccggaatggc gggtacctt accaggtcgg     480 gatcaattac ataggatgcc atgtgcgtgg atttgattgc atcgctgtcc cttttgtatg    540
tgtccgagag cgagacatca acgcgaaaac cggaatgctc ccaacgtcgc tctctgttca    600
tagggtcttt ttttttcttc tgctccatat catctgtctt gaactaagtg atcatctgct    660
gtcacgtccc gcccaatgat tgtaaagaat gataagtgat gctcgccggg gccaggctct    720
gtgaaagttc cctctttggt tgacgatcag gtagcgccaa cgttgattgg gccgcccgta    780
aaatccgacc ctgtctcctt tcgttgcaag tctccgcgag accgtgccaa gcatgttctc    840
cggatccctc aattacataa ggtttggctc cagggtaggt ctggaagcta cccacctcgg    900
ccaagcaacc aatcacaacc agacctcgcg gcgtttcgac cttcctggtt tgtctcaggg    960
ctggccaacg tcctcccgtg gcgggtgcct ggtgatcgca ggtcgcaggc gagtgccggg   1020
cacgcggagc ccccgtcaaa gcttgaccct ttcagagcta ggtttcatta ggccttcgaa   1080
aacaacccaa ggccccgtcg caaccatcac aaccggccga taaccagatc tcggtaggtc   1140
cgataaggat ccaaaatggt gtcggctgac gttgcatgtg cccaggcagg aggatgatcc   1200
ccagggttgt tgccggcagc tcccgcacgt cggggagggg gaggggagg ggaaagccct    1260 aactaacgtt cgttctatca cgggccgacc gggccatgct ttcggcttgt gagcggtggg   1320
gtcaagggca acaagaaatg ctaagtgcgg gacgaagaca cgcgggcatg aggtctcagg   1380
gtgacctgcg caaaaccaag tcccactcgc catgcctcca gcagcaacgt tgccgtagaa   1440
gggtcagggg gtttgttgta gacccacgac catgctgccg cgcagcggag ggttggcttg   1500
ctacaggcgc tgaagggtca actcggtgcc caaagtggct accaagcgtg ccatcaaggg   1560
aaatgagatg atggtggctc gtgggcaaag aaaagacaag ggaggtgact ctagagagat   1620
gctctcgagt tcacgggtat aagagcactg tgatcgttca caaagccggc gtactcctct   1680
agagcatcta tcatcaacat caccagaaag gtcntagacc aggtggttgc catatccagt   1740
cgcaaaagag ccaaagagcg aaggagcacg aaagcacagc ccaatcattc cctgctttgc   1800
tacttcttct ccaccatg                                                  1818
```

<210> SEQ ID NO 27
<211> LENGTH: 6774
<212> TYPE: DNA
<213> ORGANISM: Chrysosporium lucknowense
<220> FEATURE:
<221> NAME/KEY: misc_feature
<222> LOCATION: (201)..(201)
<223> OTHER INFORMATION: n = any nucleotide

<400> SEQUENCE: 27

```
gatcctaagt aagtaaacga acctctctga aggaggttct gagacacgcg cgattcttct     60
gtatatagtt ttattttca ctctggagtg cttcgctcca ccagtacata aaccttttt     120 ttcacgtaac aaaatggctt cttttcagac catgtgaacc atcttgatgc cttgacctct    180
tcagttctca ctttaacgta nttcgcgtta gtctgtatgt cccagttgca tgtagttgag    240 ataaatacc ctggaagtgg gtctgggcct ttgtgggacg gagccctctt tctgtggtct     300
ggagagcccg ctctctaccg cctaccttct taccacagta cactactcac acattgctga    360
actgacccat cataccgtac tttatcctgt taattcgtgg tgctgtcgac tattctatt     420
```

| | |
|---|---|
| gctcaaatgg agagcacatt catcggcgca gggatacacg gtttatggac cccaagagtg | 480 |
| taaggactat tattagtaat attatatgcc tctaggcgcc ttaacttcaa caggcgagca | 540 |
| ctactaatca acttttggta gacccaatta caaacgacca tacgtgccgg aaattttggg | 600 |
| attccgtccg ctctccccaa ccaagctaga agaggcaacg aacagccaat cccggtgcta | 660 |
| attaaattat atggttcatt ttttttaaaa aaattttttc ttcccatttt cctctcgctt | 720 |
| ttcttttttcg catcgtagtt gatcaaagtc caagtcaagc gagctatttg tgctatagct | 780 |
| cggtggctat aatcagtaca gcttagagag gctgtaaagg tatgatacca cagcagtatt | 840 |
| cgcgctataa gcggcactcc tagactaatt gttacggtct acagaagtag gtaataaaag | 900 |
| cgttaattgt tctaaatact agaggcactt agagaagcta tctaaatata tattgaccct | 960 |
| agcttattat ccctattagt aagttagtta gctctaacct atagatagat gcatgcggcc | 1020 |
| gcaggtacca ggcaattcgc cctatagtga gtcgtattac gcgcgctcac tggccgtcgt | 1080 |
| tttacaacgt cgtgactggg aaaaccctgg cgttacccaa cttaatcgcc ttgcagcaca | 1140 |
| tccccctttc gccagctggc gtaatagcga agaggcccgc accgatcgcc ttcccaaca | 1200 |
| gttgcgcagc ctgaatggcg aatgggacgc gccctgtagc ggcgcattaa gcgcggcggg | 1260 |
| tgtggtggtt acgcgcagcg tgaccgctac acttgccagc gccctagcgc ccgctccttt | 1320 |
| cgctttcttc ccttcctttc tcgccacgtt cgccggcttt ccccgtcaag ctctaaatcg | 1380 |
| ggggctccct ttagggttcc gatttagtgc tttacggcac ctcgacccca aaaaacttga | 1440 |
| ttagggtgat ggttcacgta gtgggccatc gccctgatag acggttttc gccctttgac | 1500 |
| gttggagtcc acgttcttta atagtggact cttgttccaa actggaacaa cactcaaccc | 1560 |
| tatctcggtc tattcttttg atttataagg gattttgccg atttcggcct attggttaaa | 1620 |
| aaatgagctg atttaacaaa aatttaacgc gaattttaac aaaatattaa cgcttacaat | 1680 |
| ttaggtggca cttttcgggg aaatgtgcgc ggaaccccta tttgtttatt tttctaaata | 1740 |
| cattcaaata tgtatccgct catgagacaa taaccctgat aaatgcttca ataatattga | 1800 |
| aaaaggaaga gtatgagtat tcaacatttc cgtgtcgccc ttattccctt ttttgcggca | 1860 |
| ttttgccttc ctgtttttgc tcacccagaa acgctggtga aagtaaaaga tgctgaagat | 1920 |
| cagttgggtg cacgagtggg ttacatcgaa ctggatctca acagcggtaa gatccttgag | 1980 |
| agttttcgcc ccgaagaacg ttttccaatg atgagcactt taaagttct gctatgtggc | 2040 |
| gcggtattat cccgtattga cgccgggcaa gagcaactcg gtcgccgcat acactattct | 2100 |
| cagaatgact tggttgagta ctcaccagtc acagaaaagc atcttacgga tggcatgaca | 2160 |
| gtaagagaat tatgcagtgc tgccataacc atgagtgata acactgcggc caacttactt | 2220 |
| ctgacaacga tcgaggacc gaaggagcta accgcttttt tgcacaacat ggggatcat | 2280 |
| gtaactcgcc ttgatcgttg ggaaccggag ctgaatgaag ccataccaaa cgacgagcgt | 2340 |
| gacaccacga tgcctgtagc aatggcaaca acgttgcgca aactattaac tggcgaacta | 2400 |
| cttactctag cttcccggca acaattaata gactggatgg aggcggataa agttgcagga | 2460 |
| ccacttctgc gctcggccct tccggctggc tggtttattg ctgataaatc tggagccggt | 2520 |
| gagcgtgggt ctcgcggtat cattgcagca ctggggccag atggtaagcc ctcccgtatc | 2580 |
| gtagttatct acacgacggg gagtcaggca actatggatg aacgaaatag acagatcgct | 2640 |
| gagataggtg cctcactgat taagcattgg taactgtcag accaagttta ctcatatata | 2700 |
| ctttagattg atttaaaact tcatttttaa tttaaaagga tctaggtgaa gatccttttt | 2760 |

```
gataatctca tgaccaaaat cccttaacgt gagttttcgt tccactgagc gtcagacccc    2820
gtagaaaaga tcaaaggatc ttcttgagat cctttttttc tgcgcgtaat ctgctgcttg    2880
caaacaaaaa aaccaccgct accagcggtg ttttgtttgc cggatcaaga gctaccaact    2940
ctttttccga aggtaactgg cttcagcaga gcgcagatac caaatactgt ccttctagtg    3000
tagccgtagt taggccacca cttcaagaac tctgtagcac cgcctacata cctcgctctg    3060
ctaatcctgt taccagtggc tgctgccagt ggcgataagt cgtgtcttac cgggttggac    3120
tcaagacgat agttaccgga taaggcgcag cggtcgggct gaacggggggttcgtgcaca    3180
cagcccagct tggagcgaac gacctacacc gaactgagat acctacagcg tgagctatga    3240
gaaagcgcca cgcttcccga agggagaaag gcggacaggt atccggtaag cggcagggtc    3300
ggaacaggag agcgcacgag ggagcttcca gggggaaacg cctggtatct ttatagtcct    3360
gtcgggtttc gccacctctg acttgagcgt cgatttttgt gatgctcgtc aggggggcgg    3420
agcctatgga aaaacgccag caacgcggcc ttttttacggt tcctggcctt ttgctggcct    3480
tttgctcaca tgttctttcc tgcgttatcc cctgattctg tggataaccg tattaccgcc    3540
tttgagtgag ctgataccgc tcgccgcagc cgaacgaccg agcgcagcga gtcagtgagc    3600
gaggaagcgg aagagcgccc aatacgcaaa ccgcctctcc ccgcgcgttg gccgattcat    3660
taatgcagct ggcacgacag gtttcccgac tggaaagcgg gcagtgagcg caacgcaatt    3720
aatgtgagtt agctcactca ttaggcaccc caggctttac actttatgct tccggctcgt    3780
atgttgtgtg gaattgtgag cggataacaa tttcacacag gaaacagcta tgaccatgat    3840
tacgccaagc gcgcaattaa ccctcactaa agggaacaaa agctggagct ccaccgcggt    3900
ggcggccgct ctagaactag tacggcgtgc aagtagtgtc tttctttgca ctcccgccgt    3960
cccagaagac gccgcaacaa gctgagcttg ctggaagccg aacaaaggcg ttacagagca    4020
caaacatagt ggcagtgtag gaactctaac tgggaccaaa actacgggcc cggcagaaac    4080
gttccccgcc ccgaagcgaa ggcgaacgtc gaaaagcaag accgggaccg ctcgtcccag    4140
gattagccac gaagttccag accaagtata ggagtaaacg ctcgctcgtc aaaacaattg    4200
tcaccaatca gcaccacatc ggcacataac aaccggttgc ggaactcgca tgtgaacaac    4260
aagcggctcc gggggagtga tcggctcggg cggatgaccc ggactcttcc gcgcagcaac    4320
tcggcgtgtt gttgacggca gtactccgta gttgccatga caacagtcaa tggcgtgctt    4380
cacaaggtgg agagccgaga aagcacctcg gcatgtacga gtatgtagat agtgtatcaa    4440
gcaggaagat gggggttact ttatctcaat cagatgcctg taagcgagag ccgagagcct    4500
gccctgttgt tgacacaatt ctggcctgat acgagtgaca agcgctggga cggcggctgg    4560
ggtcttttgc tcgcggcttc agctcaattc caatcctggg ccggtgccga acggcccaat    4620
cgcgagcgcc cacgaaatcg gaggtcgagg aaagaaggct gggcgagacg cggcgacaag    4680
ctgtggcaaa atggccaatt gaggttctgg gtcggctggt gatcaaccat gcatttccca    4740
gccccgcagat tctctttctc tctcgtgcag cagcggcacc agcagcagca gcagccaggg    4800
gtttgaccaa cctctccgcc cagccaccga tagtaaagat gctgcctgcg tattctgggc    4860
tgcaggagtt ccaagatctt tcggtctggc caccagctgt cacgtcaccc tccacctttg    4920
gacgacgttg ctggaaaatt cgaagccttc actaagataa ctatgccgta gcacttgcag    4980
ccccggaagc tgcaagttga ttcttggagg gctctctcca ccaccaatac gggagatctg    5040
gccccgcact tgaggaggct ggagtctcgg atcgcccact tcgcgtcgcc ctgggcccctg    5100
ggccctgggg tgatgggccc gttgccgtgg tggatggcag gagcttttca gctctcaatg    5160
```

-continued

```
ggcgaatgct actccgtagg tcggagtggc tggaagcggc ggaacggaca gggggaggtt    5220
ggggaaaatg ctccgcagga agagcaggga gtggggagct gcggtcggcc ctgtggagcc    5280
cgtgcagggc cagctaatcc aattcgggcc acaataaaca agagagggcc ccacatcatg    5340
taaacagagg ctcagaagct cctgccacac tgggagggtt tcgaagtctg acgactgcca    5400
atggacccca gccatcgcga gcacacagca gttcgcacgc tcccattggg ttcctcatca    5460
cgcagtcgct ctccccgcca accagcgcca ggtccgggaa cagcggcgca aatgcgtatt    5520
tgagggcgcc tcgctcgagc aacctgtgcc tgaccttctc ctcctccttc tgcaccttgc    5580
atctcgtcgc gtccactcgc aggcaaccac acatcctcct cctctcccaa aaccccccg    5640 cttttctttt cccttgttgg aattcgattg aaaagaaga cgggtccgtc tagagaccgc    5700
cttctcacct ttctctcgac ttctttctag gaaaagaagc aagagtcatt cttcttgtcc    5760
accttctggt tcacggaagg tcgaggagaa gattgcctct gcccccaaag tcgccaacct    5820
ggactttgaa gcacgtgttc cggtcccttt cagtgtcttc ccgtcctcgt acagggagtc    5880
cgagaccgcc acccaaaccc actcccacga agaggttgag atcaagctcc cccagctcgc    5940
cggacgggaa ggtcaacact cttcattcca agcccaagca catcttcctc ccagcggaga    6000
gggtcgcttc agagaagaag aggtccgcat cactcgtcaa gaggaacatc accgccgtcc    6060
cggcatccgt gaagagttcg ttcaccgcga ggagcgtcac cggtaagttt agttttgtt    6120 ttgattcacc acccattgtc ttccccgcct ttttcttttt cttcccttgc tctcttgccc    6180
ctgtctagtg tagggcattg ccaaggccat cttcacacac acacaccccc cccccccc    6240 accctcagct gggggggggg gtggcctggg ttgaccaagg gacggtgaag actactacta    6300
cttgagccac tcaaacccat gcatgacaca gggttttcct tttctttttc tcttttcctt    6360
taactaacca accactccaa cattagccct cagtcaacct actccgagtc tcgcatcgag    6420
ttcgatactg agcaccgcac tcacaactcc gtcattgacg ttgctgagag cgagtatcgt    6480
gcccgtgtcc agcccaacta ccgcaaggaa gcttccgtag tcggtaccac cgtcgacgga    6540
tcccgcttca gccacagccg caaggccagc agcaccacct ccaccacac cgacgagtac    6600 accgtcgatc ccctagcca ccgccccgtc tacaagaagg agtcggttga agtcgccggt    6660
accactgttg accccctgc tcctcgttcg acctaccacg agcaggtgaa cattgttgaa    6720
gagaccgttg acgctcaccg ttacgctcct caacccaaca caacaacac catg    6774
```

<210> SEQ ID NO 28
<211> LENGTH: 1468
<212> TYPE: DNA
<213> ORGANISM: Chrysosporium lucknowense

<400> SEQUENCE: 28

```
gcggccgctt ccccatgaat ggcaaccggg ctgatgacct gtgtgggaag aaatgggtt      60 gggtcgggca atgggaagaa aacggaaaga gggaaggaaa catgcctgta gtcgaggctg     120
agagtgtacg tacgtccgta cattccagta accaggcgag aatgagcaat gatacccgc      180 atttcttgga taattaactc gttccagagc acgacttacg cagcactact ccgtactgtt     240
ggagcgctta gcacgctgga aacttggcag ccgtccgaag ccgctcggcc ccatcctctc     300
gctggtagct agtgtagtcc cgtgctttac aacgcggcta tacagcccgt acagttgtaa     360
agtacctaca tacatgcact actattatta tccttctaga gtgggttccg aattccaggg     420
aagatcttcc tatggctatc tggctgaaac ttggggagg agtgcggaag gggggaggg      480
```

-continued

```
aacgagcctc cacattgcat acgaccgggg aatgcgggac cctaagcgaa ccaggaaccc      540
ggttattgca ctcggaattg ccgcagatcc ctgcgttcca cccgctcgaa cggtcaacat      600
taactaatct gtagtggagt tactgttgac tttctgactc gtgtcactgg tcctcgccca      660
agttcgaaaa cagaattgca ttttttgtcct tttgttcgga gctttcgagg aataattcca    720
ttgtaggtat ggagtaatta tggagtatac acggcccagg ggcgctacac acaccatcgc     780
cgagaatggg aggtcgagct cgcgacgctc aggatcccat cgatattttc ccttatccct     840
gctctcacta gcgcgcagag ccgcctccgc gcggggatgc cggttgttgc cggcgtgctt     900
tttatccgct gcccttggtt gctcatttcc cggttcttgg gtcgcttgcc aagcagctcc     960
ggcggagaag aataccacag gagggagcat cggggcgcga agggcattgc actatgcgga    1020
cgagatgctt caacaccatc atggacctgt ccggaactcc caagaacagg cgacgccaag    1080
gacggagtag acctccccgg tccgtcttct ctctgcctgg caatttagcc aaaaatccga    1140
cccgacttgc gacgattcct acctcctagc gcgtgcgcgc tgaagcagtc gcgagagtcg    1200
caaggcatgg gcccgagtct ggctggcatc gtcaaacgtg atcggcccgt cgagcgtgcg    1260
tgtataaatg catcaaggag cgactgcccc cccatcaata accacccggt tgcttgagtc    1320
tctcgcactc gcggcccctt cttctctgct tcgcacgcat ctcgctgtct cgctgtctcg    1380
ctgtctcact gtctcgctgt ctcactgtct cgctgtctca ctgtctcgct gtctcactgt    1440
ctcactcgtc catcagagca aaaccatg                                       1468
```

<210> SEQ ID NO 29
<211> LENGTH: 1803
<212> TYPE: DNA
<213> ORGANISM: Chrysosporium lucknowense

<400> SEQUENCE: 29

```
tagtagttgt caaccttggc agcgagagtc ccgaggcggt agatgagaga aaaaaggacc      60
gatgttgact ccatgccat cgatggcgtc gtctcggcta gacgtcgtcg gcgttattct      120
gggggaggca atcccgggtg aggagagaaa tagacgcgtc gccatctagc agccatcact    180
cagtggcatc acctgcgcgt tgacttgcct tcgaaggctc tcctgagccg agcatgtgat     240
tacgatgtat aagacctgca ttgagctcga cgttcccgag cgtcggcgcg agcttccaat    300
tcggttgagg ctccggcggc ttccccggt ttcctgctgg actagctgcc gtggcggggg    360
gacggcagag cgactccgac gcgccccatg cgagcaacgg cccgattttc gatgagatct    420
gcggggcgcc ggagtggcag cagttcgtca gcttggcagg cacggctccc caccttcttc     480
cttcttccac actaggccct cccacaagcg accagatgct tgttaagtac gcagtagtgt    540
ctcggctcgc ccagagaaca atggcacgcc gatctgtcta atgaccaaga gccacggttc     600
gagaccatcc attggactgg agggcctgcg aggcatcacg ccgaacccat gtcatgctac     660 tcttctctgtt cacccccgga gatggcgtga aactgcgcgt ttactcgcgg ctcagcatgt    720
gctcacgttg ggtaggtccc gcaaagtcag aggtagggag gtactttgta ggcacaaatc     780
atgtacacgt tcgtacctga ggtagctatc tcgcctcagg cacacgaggc ccgttcgacg    840
agagagagga agagcaacca agaatagtca aggatattat tactctttcc ctggtatttc    900
tggacatttt gtccaggatt tgttcgccc tttaattttg aacaattatg ctcccgtcgg     960
ctccgatcca cgcctcttaa ctctccttta gcctttcgcc tctatttcct tgaatttcaa    1020
ttctcccaag ggccctgctt tctacagcaa agaatccgta ccctactctc tttcgcgcac    1080
agagtgaggg agcaacaggg attgcgaaat gcacagcaga gtttgtgtaa cttcggcagc    1140
```

```
tcttccccac attcagatgc atgttactgg agaatgcgga gaagttatag tctggggtag    1200
taggtataac gctggtactc ccgaggtagg tagcaacctt ggctgacctt gggaagcgag    1260
ggcgcttgtg acgctgacga tccagaagca gcccgccgat agtatacgtg gagacggtgc    1320
ttcttgctat aagcgctcaa ctccgctacc catgttcacc gtcttcccct tggacgacgg    1380
catcactccg atacccatgt ctcctgggta gctccgagta gtcgcccgag cgcccttctc    1440
ccccctcccc ctttctccta ataaacggcc gagtcgggca gctcgacgt tgcaccgtag     1500 cgtcgcagcc tgcgtagaag cacgcgtaga agcaccgagc tccaagctcc aagacgccaa    1560
aagccgccgc gaagtggccg tcggcccttc ccgcatgcg cagctccggc accaggtccg     1620
aaacgctcca tcaccccata tcccagtcag aacagcggct gctttccgga tttggaagtc    1680
tggaggtcgc gaatgaaggc tcgcgttcga ctataataac agctccggat ggcaggcctc    1740
gttgcccagc tccaggacca cctcccatcc gtaaacggat ctggcctcgt cacgcccgcc    1800
atg                                                                  1803

<210> SEQ ID NO 30
<211> LENGTH: 1547
<212> TYPE: DNA
<213> ORGANISM: Chrysosporium lucknowense

<400> SEQUENCE: 30
atgcacttct ccaccgctct cctggccttc ctgcccgccg ccctcgcggc ccctactgcc      60 gagacccctcg acaagcgcgc cccgatcctg actgctcgcg ctggccaggt cgtcccgggc   120
aagtacatca tcaagctccg cgacggagcc agcgacgatg tccttgaggc cgccatcggc    180
aagctccgct ccaaggccga ccacgtctac cgcggcaagt tcaggggctt tgccggcaag    240
ctcgaggatg acgtccttga cgccatccgt cttctccccg aagtgagtcc gcgtcccgga    300
aagaaataga gcgagcgggg gagagagtga agggcgaaaa gagccgtgtt ttgttaaccg    360
cttgtctttt ctttctctct tgcaataggt cgagtacgtc gaggaggagg ccatcttcac    420
catcaacgcg tacaccctcg cagtccaacg ccctgggc cttgcgcgcc tctcgtccaa      480
gaccgcgggc tccaccacct acacctacga caccagcgcc ggcgagggca cctgtgccta   540
tgtgatcgac acgggcatct acactagcca ctccgtatgt ctcgcggtta cctccccttt    600
cggaagaagg ggcatccata tgctgacccc tcctgatcac aggacttcgg cggccgtgcc    660
actttcgccg ccaacttcgt cgacagctct aacaccgatg gcaacggcca cggcacccac    720
gtcgccggca ccatcggcgg caccacgtac ggtgttgcca agaagaccaa gctctacgcc    780
gtcaaggttc tcggctccga cggctctggc accacgtatg cctcgcaccc gcgcacccgc    840
acacccgccc ggccgttatc ttctgactga cattcctctt tctcctctct agttctggtg    900
tcattgctgg catcaacttc gtcgctgacg acgcgcccaa gcgcagctgc cccaagggcg    960
tcgtcgccaa catgtcgctc ggcggtagct actcggcctc catcaacaac gccgccgccg  1020
ccctcgtcag gtcgggcgtc ttcctggccg tcgccgccgg caacgagaac cagaacgccg  1080
ccaactcgtc gcccgcctcc gaggcgtccg cctgcaccgt cggcgccacc gacaggaacg  1140
acgccaaggc cagctactcc aactacgcag cgtcgtcga tatccaggcc cccggctcca   1200
acatcctgag cacctggatc ggcagcacct ctgctaccgt aagcccccc tcccccacc    1260 caccccagc ctttgcgac attcccgccc cgtatttatt tctccgggt ggggagaaa      1320 caaaacaaaa tagctaacat gagatgcact ctcagaacac catctcgggt acctcgatgg  1380
```

```
cctcccccca cattgccggc ctcggtgcct acctcctggc cctcgagggc tccaagaccc    1440
ctgccgagct ctgcaactac atcaagtcga ccggcaacgc cgccatcact ggcgttccca    1500
gcggcaccac caaccgcatc gccttcaacg gcaacccctc tgcctga                 1547
```

<210> SEQ ID NO 31
<211> LENGTH: 392
<212> TYPE: PRT
<213> ORGANISM: Chrysosporium lucknowense

<400> SEQUENCE: 31

```
Met His Phe Ser Thr Ala Leu Leu Ala Phe Leu Pro Ala Ala Leu Ala
1               5                   10                  15

Ala Pro Thr Ala Glu Thr Leu Asp Lys Arg Ala Pro Ile Leu Thr Ala
            20                  25                  30

Arg Ala Gly Gln Val Val Pro Gly Lys Tyr Ile Ile Lys Leu Arg Asp
        35                  40                  45

Gly Ala Ser Asp Asp Val Leu Glu Ala Ala Ile Gly Lys Leu Arg Ser
    50                  55                  60

Lys Ala Asp His Val Tyr Arg Gly Lys Phe Arg Gly Phe Ala Gly Lys
65                  70                  75                  80

Leu Glu Asp Asp Val Leu Asp Ala Ile Arg Leu Leu Pro Glu Val Glu
                85                  90                  95

Tyr Val Glu Glu Glu Ala Ile Phe Thr Ile Asn Ala Tyr Thr Ser Gln
            100                 105                 110

Ser Asn Ala Pro Trp Gly Leu Ala Arg Leu Ser Ser Lys Thr Ala Gly
        115                 120                 125

Ser Thr Thr Tyr Thr Tyr Asp Thr Ser Ala Gly Glu Gly Thr Cys Ala
    130                 135                 140

Tyr Val Ile Asp Thr Gly Ile Tyr Thr Ser His Ser Asp Phe Gly Gly
145                 150                 155                 160

Arg Ala Thr Phe Ala Ala Asn Phe Val Asp Ser Ser Asn Thr Asp Gly
                165                 170                 175

Asn Gly His Gly Thr His Val Ala Gly Thr Ile Gly Gly Thr Thr Tyr
            180                 185                 190

Gly Val Ala Lys Lys Thr Lys Leu Tyr Ala Val Lys Val Leu Gly Ser
        195                 200                 205

Asp Gly Ser Gly Thr Thr Ser Gly Val Ile Ala Gly Ile Asn Phe Val
    210                 215                 220

Ala Asp Asp Ala Pro Lys Arg Ser Cys Pro Lys Gly Val Val Ala Asn
225                 230                 235                 240

Met Ser Leu Gly Gly Ser Tyr Ser Ala Ser Ile Asn Asn Ala Ala Ala
                245                 250                 255

Ala Leu Val Arg Ser Gly Val Phe Leu Ala Val Ala Ala Gly Asn Glu
            260                 265                 270

Asn Gln Asn Ala Ala Asn Ser Ser Pro Ala Ser Glu Ala Ser Ala Cys
        275                 280                 285

Thr Val Gly Ala Thr Asp Arg Asn Asp Ala Lys Ala Ser Tyr Ser Asn
    290                 295                 300

Tyr Gly Ser Val Val Asp Ile Gln Ala Pro Gly Ser Asn Ile Leu Ser
305                 310                 315                 320

Thr Trp Ile Gly Ser Thr Ser Ala Thr Asn Thr Ile Ser Gly Thr Ser
                325                 330                 335

Met Ala Ser Pro His Ile Ala Gly Leu Gly Ala Tyr Leu Leu Ala Leu
            340                 345                 350
```

```
Glu Gly Ser Lys Thr Pro Ala Glu Leu Cys Asn Tyr Ile Lys Ser Thr
        355                 360                 365
Gly Asn Ala Ala Ile Thr Gly Val Pro Ser Gly Thr Thr Asn Arg Ile
    370                 375                 380
Ala Phe Asn Gly Asn Pro Ser Ala
385                 390
```